(12) United States Patent
Roche et al.

(10) Patent No.: US 10,058,647 B2
(45) Date of Patent: Aug. 28, 2018

(54) BIOMIMETIC ACTUATION DEVICE AND SYSTEM, AND METHODS FOR CONTROLLING A BIOMIMETIC ACTUATION DEVICE AND SYSTEM

(71) Applicants: President and Fellows of Harvard College, Cambridge, MA (US); Children's Medical Center Corporation, Boston, MA (US)

(72) Inventors: Ellen T. Roche, Cambridge, MA (US); Steven Obiajulu, Westfield, NJ (US); Conor J. Walsh, Cambridge, MA (US); David J. Mooney, Sudbury, MA (US); Frank A. Pigula, Concord, MA (US)

(73) Assignees: President and Fellows of Harvard College, Cambridge, MA (US); The Children's Medical Center Corporation, Boston, MA (US)

( * ) Notice: Subject to any disclaimer, the term of this patent is extended or adjusted under 35 U.S.C. 154(b) by 122 days.

(21) Appl. No.: 15/027,246

(22) PCT Filed: Oct. 6, 2014

(86) PCT No.: PCT/US2014/059368
§ 371 (c)(1),
(2) Date: Apr. 4, 2016

(87) PCT Pub. No.: WO2015/051380
PCT Pub. Date: Apr. 9, 2015

(65) Prior Publication Data
US 2016/0346449 A1    Dec. 1, 2016

Related U.S. Application Data

(60) Provisional application No. 61/887,310, filed on Oct. 4, 2013.

(51) Int. Cl.
*A61M 1/12* (2006.01)
*F15B 15/10* (2006.01)
*A61M 1/10* (2006.01)

(52) U.S. Cl.
CPC ............ *A61M 1/122* (2014.02); *A61M 1/106* (2013.01); *F15B 15/103* (2013.01);
(Continued)

(58) Field of Classification Search
CPC . A61M 1/22; A61M 1/106; A61M 2001/1003
(Continued)

(56) References Cited

U.S. PATENT DOCUMENTS 5,098,369 A    3/1992  Heilman
5,250,167 A    10/1993 Adolf
(Continued)

FOREIGN PATENT DOCUMENTS

WO    WO 2012/059380 A2    5/2012
WO    WO 2012/103073 A2    8/2012
(Continued)

OTHER PUBLICATIONS

International Search Report, PCT/US2014/059368, dated Mar. 3, 2015 (5 pages).
(Continued)

*Primary Examiner* — Suzette J Gherbi
(74) *Attorney, Agent, or Firm* — Nixon Peabody LLP

(57) ABSTRACT

A biomimetic actuation device includes a flexible substrate, conformable for disposition about an object, defining an apex and a base, bearing at least one soft actuator configured to change state from a first state to a second state upon introduction of a pressurized fluid to an internal volume of the at least one soft actuator.

17 Claims, 36 Drawing Sheets

(52) U.S. Cl.
CPC ......... *A61M 1/1008* (2014.02); *A61M 1/1067* (2013.01); *A61M 1/1068* (2013.01); *A61M 1/12* (2013.01)

(58) Field of Classification Search
USPC ....................................................... 623/3.12
See application file for complete search history.

(56) References Cited

U.S. PATENT DOCUMENTS

| | | | | |
|---|---|---|---|---|
| 6,120,477 | A * | 9/2000 | Campbell | A61F 2/958 604/96.01 |
| 6,309,341 | B1 * | 10/2001 | Denker | A61M 1/1055 600/16 |
| 6,602,182 | B1 | 8/2003 | Milbocker | |
| 8,316,719 | B2 | 11/2012 | Majidi | |
| 2002/0007216 | A1 * | 1/2002 | Melvin | A61F 2/02 623/3.11 |
| 2002/0007316 | A1 | 1/2002 | Melvin | |
| 2004/0135473 | A1 | 7/2004 | Byers | |
| 2004/0167375 | A1 | 8/2004 | Couvillon | |
| 2004/0225177 | A1 * | 11/2004 | Coleman | A61M 1/107 600/17 |
| 2006/0142634 | A1 * | 6/2006 | Anstadt | A61M 1/1068 600/16 |
| 2008/0132749 | A1 * | 6/2008 | Hegde | A61M 1/1053 600/16 |
| 2013/0345610 | A1 * | 12/2013 | Larson | A61B 17/1325 601/134 |
| 2015/0025426 | A1 * | 1/2015 | Larson | A61B 17/1325 601/134 |
| 2015/0337874 | A1 * | 11/2015 | Park | F15B 15/103 92/5 R |
| 2016/0017899 | A1 * | 1/2016 | Yang | F15B 15/103 623/14.13 |
| 2016/0114482 | A1 * | 4/2016 | Lessing | A61B 34/30 606/130 |
| 2016/0278957 | A1 * | 9/2016 | Gaur | A61F 5/003 |
| 2017/0000935 | A1 * | 1/2017 | Vasilyev | A61M 1/106 |

FOREIGN PATENT DOCUMENTS

| | | | | |
|---|---|---|---|---|
| WO | WO 2012/148472 | A2 | 11/2012 | |
| WO | WO 2013/044226 | A2 | 3/2013 | |
| WO | WO 2012148472 | A3 * | 7/2013 | ............ B25J 9/1075 |
| WO | WO 2013/130760 | A2 | 9/2013 | |
| WO | WO 2013130760 | A3 * | 11/2013 | .............. B25J 9/142 |

OTHER PUBLICATIONS

Written Opinion of the International Searching Authority, PCT/US2014/059368, dated Mar. 3, 2015 (18 pages).

* cited by examiner

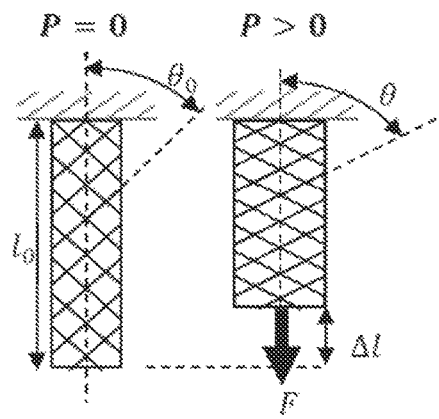
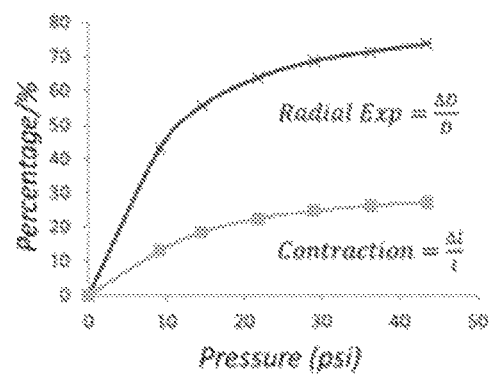
FIG. 1(a)  FIG. 1(b)
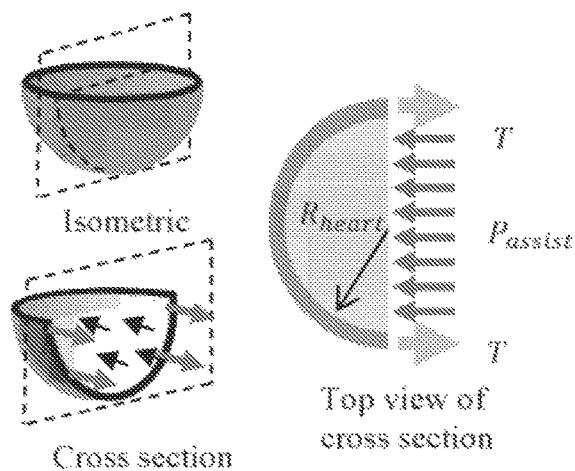
FIG. 2

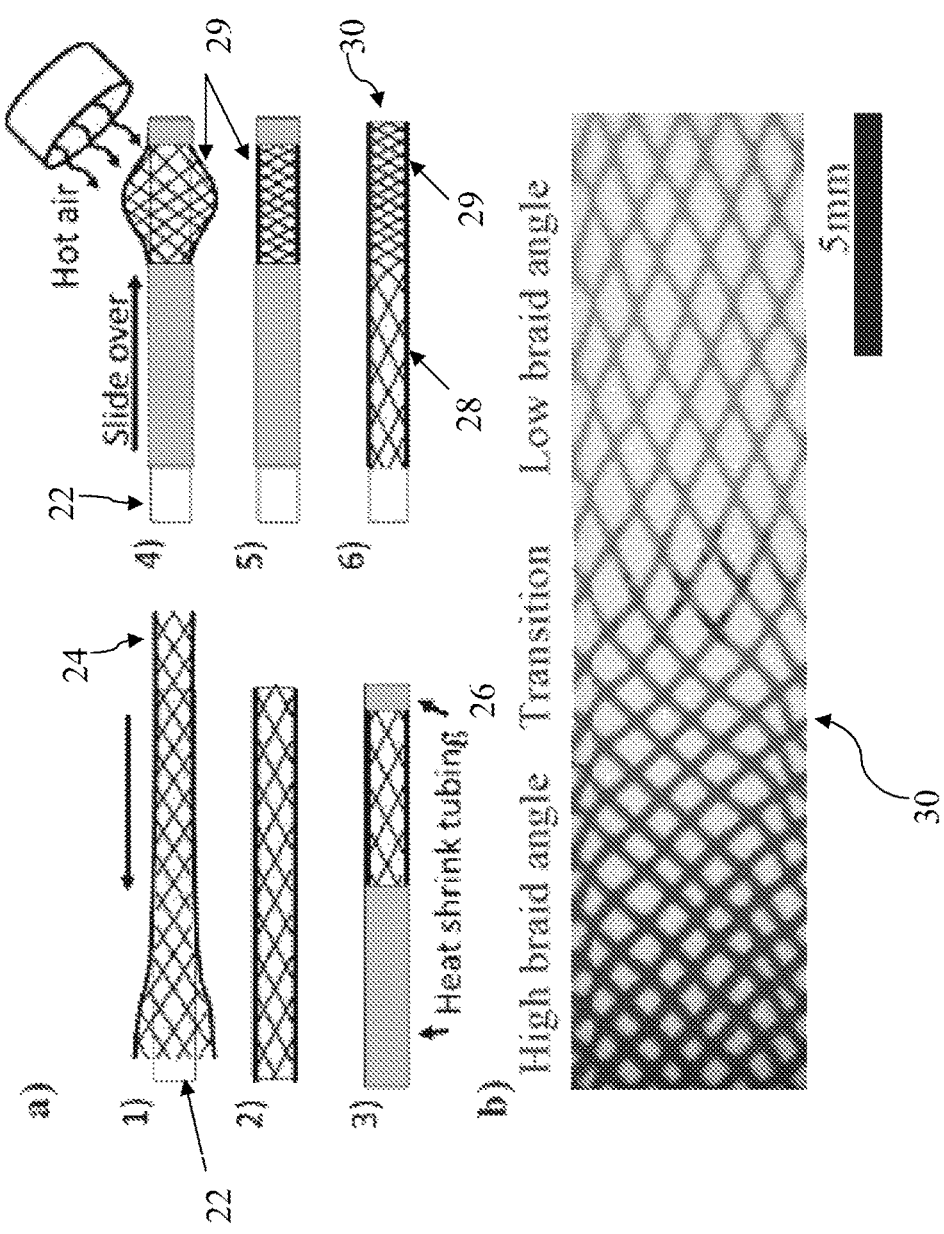

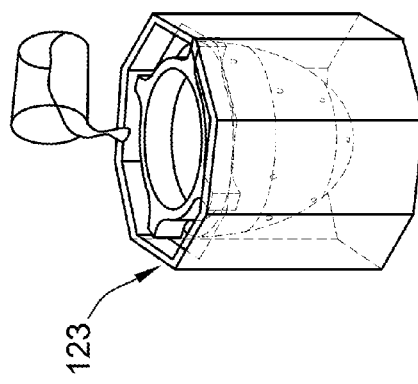
FIG. 12C
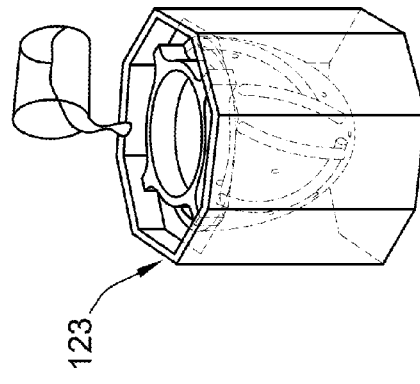
FIG. 12E
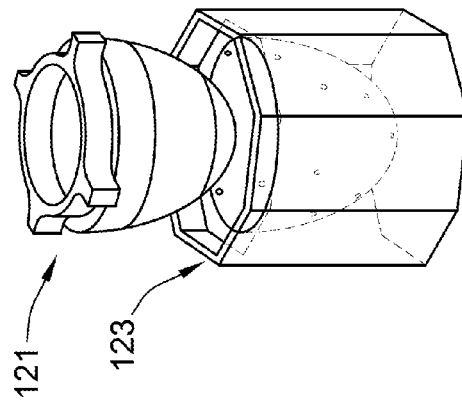
FIG. 12B
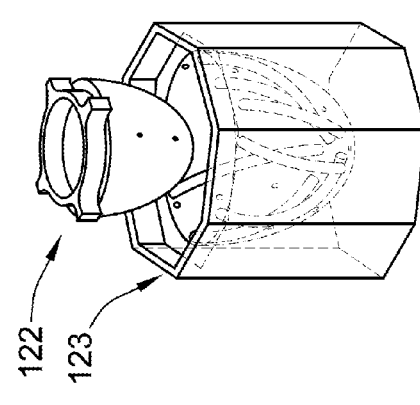
FIG. 12D
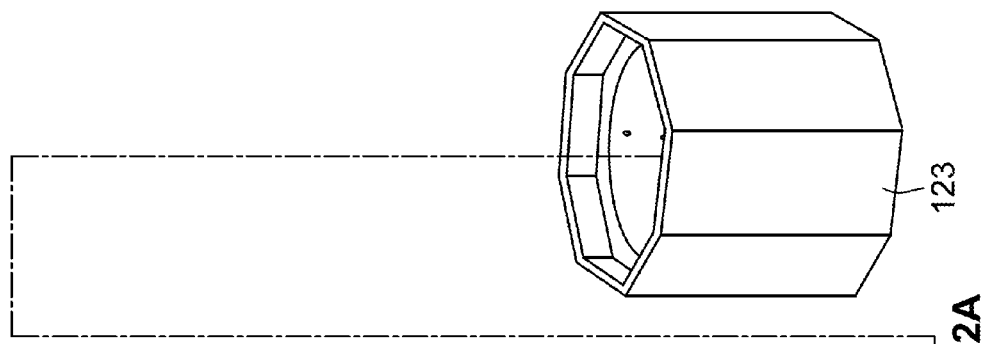
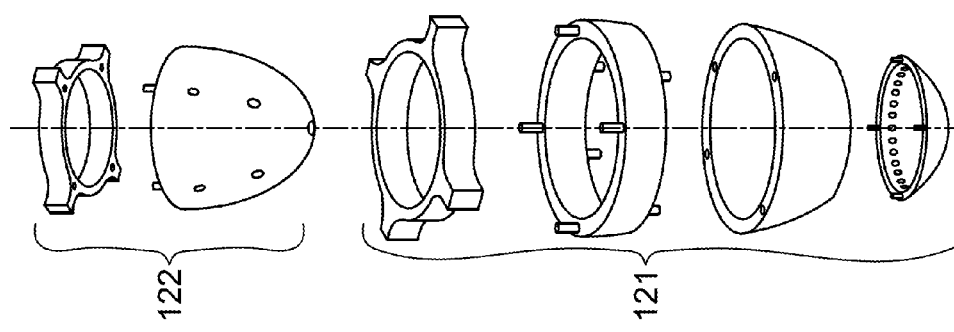
FIG. 12A

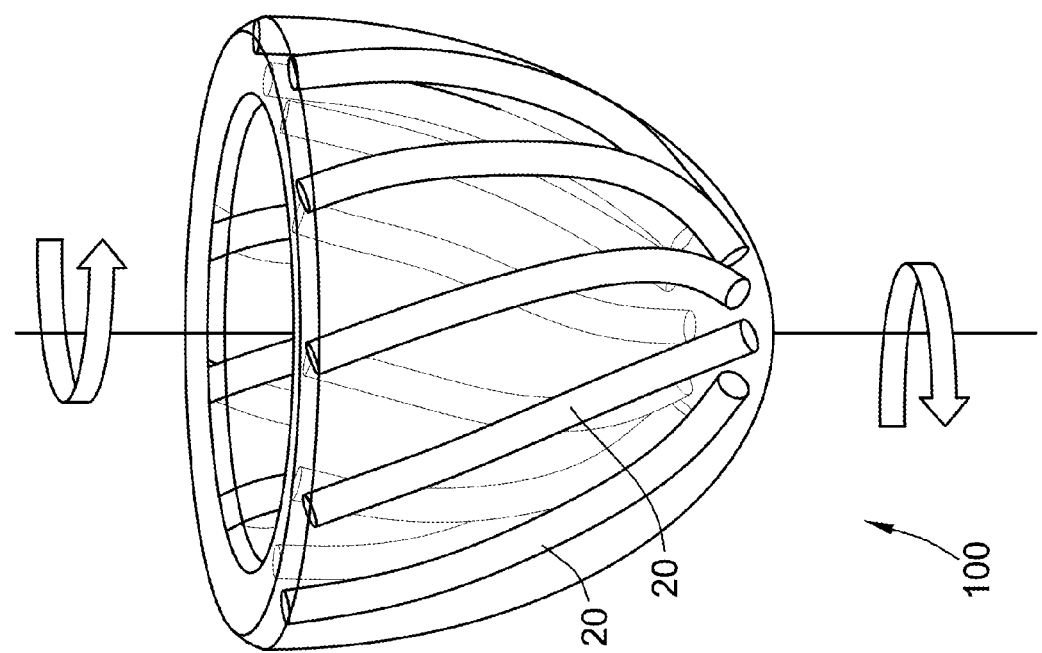
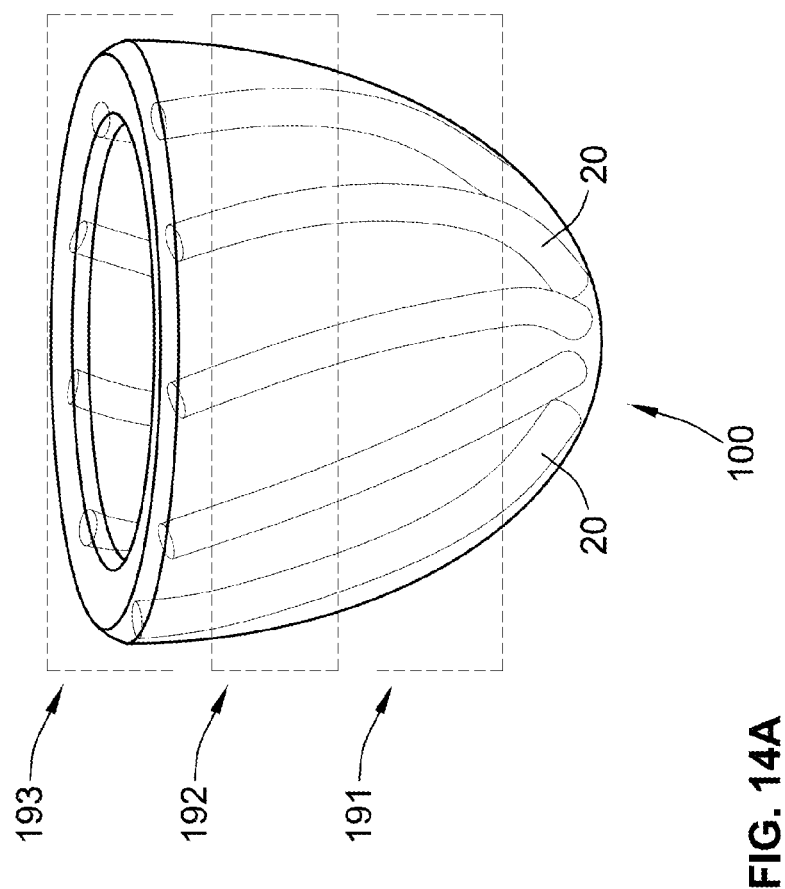
FIG. 14A

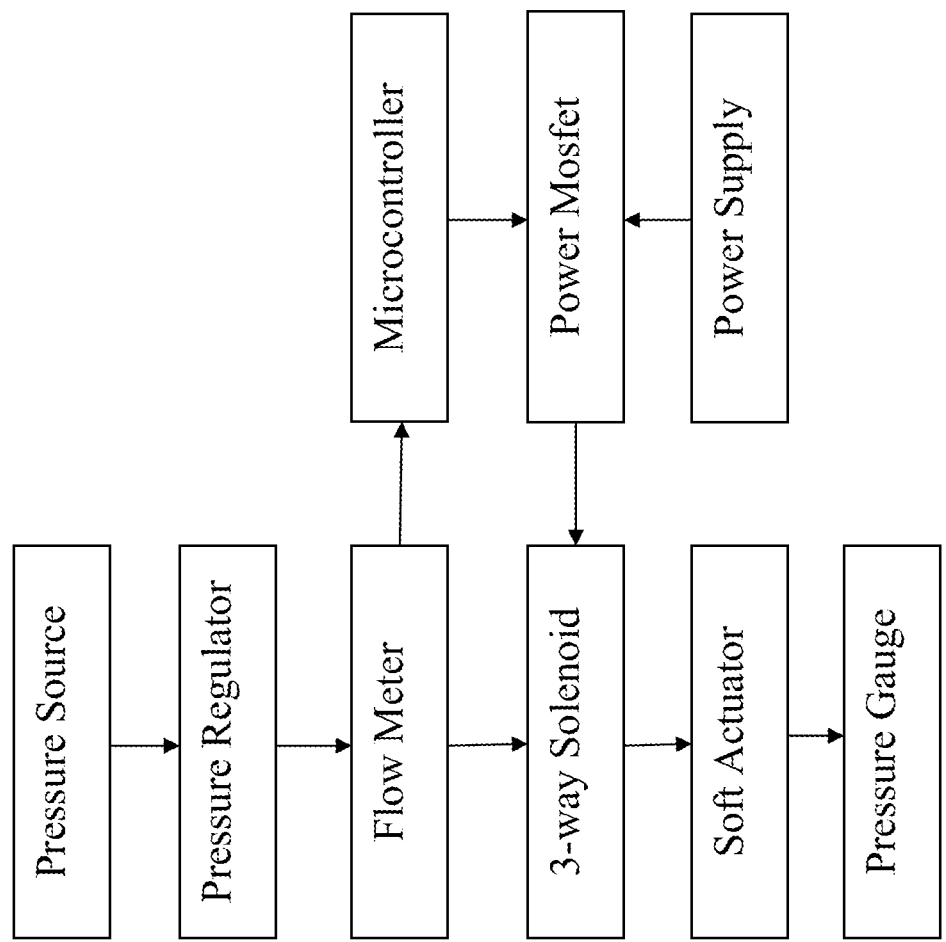

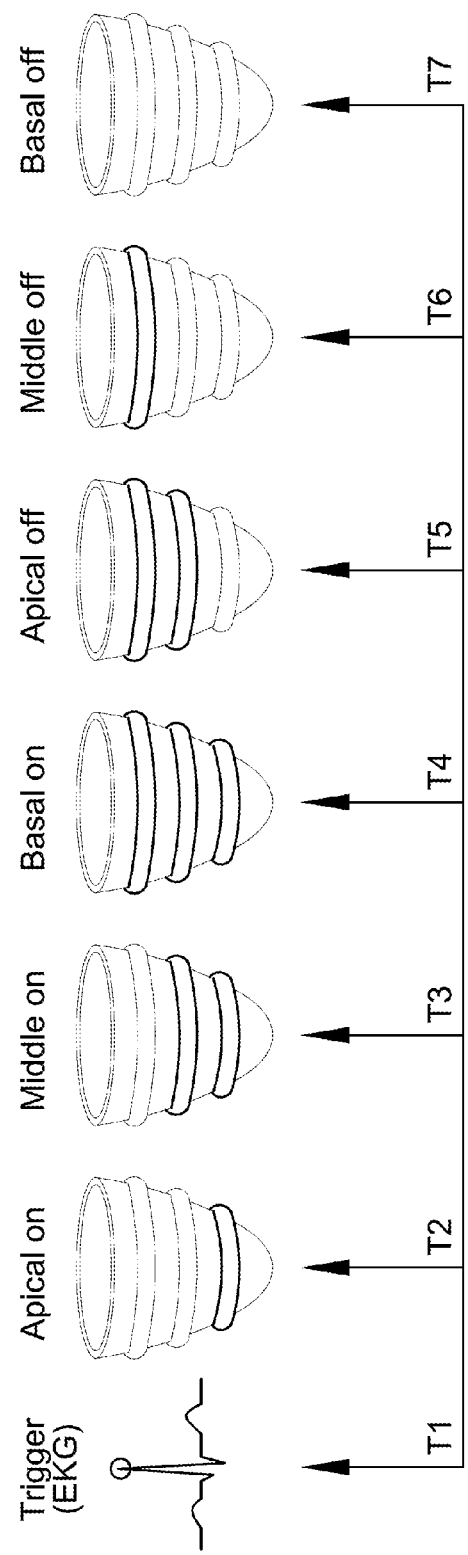
FIG. 27A
FIG. 27B

BIOMIMETIC ACTUATION DEVICE AND SYSTEM, AND METHODS FOR CONTROLLING A BIOMIMETIC ACTUATION DEVICE AND SYSTEM

CROSS-REFERENCE TO RELATED APPLICATIONS

This application is a U.S. National Phase of International Application No. PCT/US2014/059368, filed on Oct. 6, 2014, which claims the benefit and priority to U.S. Provisional Patent Application No. 61/887,310, filed on Oct. 4, 2013, both of which are incorporated herein by reference in their entireties.

STATEMENT REGARDING FEDERALLY SPONSORED RESEARCH

Some aspects of the present disclosure were made with government support, under Grant No. 5R01HL069957 awarded by the National Institutes of Health (NIH), and the government shares rights to such aspects of the present disclosure.

TECHNICAL FIELD OF THE INVENTION

The present concepts are generally directed to devices, methods and systems for providing cardiac stimulation and for cardiac simulators.

BACKGROUND OF THE INVENTION

Pneumatic artificial muscles (PAMs) are actuators that contract when pressurized with air. The most widely used PAM is the McKibben actuator, which was developed in the 1950s for actuating orthotics. McKibben actuators comprise a rubber tube enclosed in a textile mesh or braid, which contracts axially when the bladder expands it radially, acting in a manner similar to a scissor linkage and providing a load-length curve similar to that of skeletal muscle. At their ends, the bladder and mesh are crimped together to allow mechanical coupling to a load.

McKibben actuators have been used in a wide range of applications including robotics, orthotics, and industrial automation, but have not found application in direct cardiac compression (DCC), but have properties limiting the potential use of McKibben actuators inside the human body. The foremost drawback is that McKibben actuators typically have a threshold pressure of 100 kPa due to friction between the bladder and mesh coupled with an initial lack of contact between the walls of the bladder and mesh. This limitation prevents precise control of force and displacement for pressures below 100 kPa (i.e., in the operating range of cardiac compression devices). Additionally, most existing McKibben actuators have rigid, crimped attachment points at their ends that allow for easy mechanical coupling to a load. If McKibben actuators were used for DCC, such rigid end features might damage a patient's soft tissue. Further, the rigid end features have been shown to introduce local stress concentrations, causing early fatigue failure.

With regard to DCC devices, the concept of extra-cardiac assistance in the pericardial space was introduced in the 1950s, then suggested for use as a cardiac sleeve or a rubber ventricle for cardiopulmonary resuscitation in the 60s. Since then there are a number of devices are in development, both for resuscitation and chronic implant. Many have been tested in animal models, but none have FDA approval presently. The Anstadt cup has proved effective for mechanical massage of the heart to reverse cardiac arrest. The cup is elliptically shaped and covers both ventricles. By using a semi-rigid outer layer, and inflatable inner diaphragm it can deliver both diastolic extension and epicardial compression. However, the device does not synch with the native heartbeat, and therefore has potential to injure the myocardium and disturb the rhythm of the heart.

The CardioSupport system (Cardio Technologies Inc., Pine Brook, N.J.) comprises a cuff that is placed around the epicardium of the heart. The device is sealed by vacuum and contains electrodes to provide an ECG source to inflate and deflate a compressive bladder inside the cuff. Compressive force is provided by an air compressor. The Heart Booster (Abiomed, Inc., Danvers) is designed for longterm support. The compression system interfaces the heart with a cuff consisting of parallel compression tubes forming a band around the base of the heart and attached to the epicardium with surgical glue. The device uses a hydraulic drive system to fill and empty the compression tubes. The HeartPatch (Heart Assist Technologies, Australia) has non-surround cardiac assistance and independent ventricular actuation. Other strategies for DCC use electro-active polymers, ionic polymer metal nano-composites or shape memory alloys for actuation, each being limited by force generation or dynamic response. Mechanical ventricular assist devices (VADs) are also conventionally used to assist either the right (RVAD) or left (LVAD) ventricle, or both at once (BiVAD).

Passive restraint devices exist in the form of a mesh sock or girdle that surrounds the heart (e.g., CorCap Cardiac Support Device (CSD)) to provide support and reduce ventricular wall stress, such as by reducing left ventricle (LV) size and left ventricular ejection fraction (LVEF).

Regarding cardiac bench-top simulators, most existing simulators are passively actuated by external pumps or motors and do not mimic tissue material properties. One cardiac simulator that has embedded actuation in the heart wall is the Chamberlain Heart (manufactured by the Chamberlain Group, Great Barrington, Mass.). Such cardiac simulators are used, for example, in cardiothoracic training as a surgical training tool.

SUMMARY OF THE INVENTION 5.1 million Americans have heart failure (HF), a disease that costs the nation an estimated $32 billion each year. Currently, patients with end stage or medically refractory HF are often considered for heart transplantation. However, donor availability is extremely limited and many patients die awaiting transplantation. Mechanical assistance of the failing myocardium, ventricular assist devices (VADs) are utilized as a life prolonging therapy, either as a bridge to transplant, or in some cases, destination therapy. All current generation of VADs are based on pump and valve technology; the heart and great vessels are cannulated, blood is removed from the heart, and pumped through a one-way valve under pressure into the aorta. Because of the contact between blood and these artificial surfaces, anticoagulation therapy is required. Despite best efforts at appropriate anticoagulation, the risk of thromboembolic events including, stroke, may occur in up to 20% of patients. Further, although the preferred method for advanced heart failure treatment is heart transplantation, the growing demand exceeds the supply. To address these risks of blood contacting devices, such as the ventricular assist devices (VADs), a number of extra-cardiac devices, both passive and active have been developed. Active systolic assist or direct cardiac compression (DCC) is a non-blood contacting method of cardiac assistance involving implantation of a device that surrounds the heart and contracts in phase with the native heartbeat to provide direct mechanical assistance during the ejection phase (systole) of the cardiac cycle without contacting blood. Since the first proposed DCC device for resuscitation of a totally arrested heart several have been developed, such as the aforementioned CardioSupport System and Heart-Booster, but none have received FDA approval.

The present inventors have identified two deficiencies of current DCC devices. First, they do not mimic the twisting motion of the heart, but instead invert the normal curvature of the heart and cause friction at the epicardium/device interface. Second, they do not typically augment diastolic function and can restrict diastolic filling.

Because there is no contact between the blood and the DCC devices disclosed herein, the need for anticoagulation and the corresponding risk of thromboembolic complications is dramatically reduced. While others have recognized the advantage of avoiding contact between the blood and DCC devices, previous devices have suffered from two important shortcomings: (i) previous devices have provided mechanical assistance only during the systolic phase of the cardiac cycle and (ii) Previous direct cardiac compression devices, by design, have inverted the normal curvature of the heart. As to the first shortcoming, it has become increasingly apparent that diastolic dysfunction of the failing heart is a critical contributor to the mortality and morbidity of heart failure. The soft actuators disclosed herein, such as modified Pneumatic Artificial Muscles (PAMs), provide a physiological, atraumatic actuation strategy due to their self-limiting load-length curves. These actuators can extend as well as contract, enabling augmentation of both systolic and diastolic function. As to the second shortcoming, the inverting of the normal curvature of the heart by previous direct cardiac compression devices has resulted in friction and trauma at the epicardium/device interface, resulting in decreased efficacy as the device was not integrated and synchronized with native cardiac contraction mechanics and direction. In contrast, in accord with at least some aspects of the DCC disclosed herein, the soft actuators are integrated along the surface of the epicardium, adopting a biomimetic approach where individual actuators are oriented in a helical and circumferential fashion similar to epicardial and myocardial fibers of the heart respectively, thus replicating cardiac motion while providing synchronized mechanical assistance. The actuators will augment cardiac function along the force vectors of the native heart muscle.

In order to counteract the aforementioned problems, the inventors developed, and disclose herein, a biomimetic approach to DCC. In at least some aspects of this biomimetic DCC, individual actuators are oriented in a helical and circumferential fashion similar to epicardial and myocardial fibers of the heart, respectively, to replicate cardiac motion while providing mechanical assistance. Soft actuators, particularly (but not necessarily) soft elastomeric actuators, such as modified Pneumatic Artificial Muscle (PAMs)) described herein, are advantageously employed in accord with at least some aspects of the present concepts to impart a physiological, atraumatic actuation strategy. These soft actuators provide self-limiting load-length curves and can, operating at biologically safe pressures, extend as well as contract, enabling augmentation of, for example, both systolic and diastolic function.

In accord with at least some aspects of the present concepts, a design, fabrication and characterization of fully soft actuators (e.g., soft pneumatic artificial muscles (PAMs) or hydraulic artificial muscles) with low threshold pressures are utilized. The elastomeric actuators provided in accord with the present concepts may be used, for example, in applications including, but not limited to, direct cardiac compression (DCC), such as a treatment for end-stage heart failure. These new elastomeric actuators, a variant of the McKibben actuator, integrate the braid with the elastomeric tube (e.g., embedding the nylon mesh in the elastomeric tube, etc.) and are designed with a low threshold pressure and soft ends (i.e., closure of the end of the tube without rigid ends), so as to be compatible with DCC. In some aspects, these elastomeric actuators are embedded in one or more continuous or discontinuous substrates (e.g., one or more sleeve(s), one or more cup(s), one or more band(s), one or more patch(es), etc.), such as but not limited to an elastomeric structure, a textile interface or a composite material. The substrate(s) is/are then attached (e.g., via suture, medical glue, vacuum or negative pressure, biointegration, etc.) to one or more external surface of the heart to assist with the cardiac function. Thus, in at least some aspects, the direct cardiac compression (DCC) device comprises a plurality of fully soft actuators, embedded in an elastomeric substrate, configured to contract and relax in synchronization with the native electrical wave propagation of the heart, such as by using existing pacemaker technology in order to achieve synchronous motion. For example, the ECG wave serves as a trigger, and the output ECG signal (whether obtained internally through existing pacemaker technology (implantable) or externally from a plurality of electrodes/leads) is used by the DCC device control system to selectively actuate individual actuators (e.g., PAMs), groups of actuators and further, to selectively control the actuation force/displacement of such actuated actuator(s) to tailor the assistance provided by the DCC device in real time. In accord with this capability, the DCC device is configurable to, in real time, activate right and left ventricle separately (e.g., independent ventricular actuation), or actuate atria, to perform sequential actuation from apex to base, or any other sequence of actuation.

Elastomeric actuators in accord with at least some aspects of the present concepts were tested to assess whether they provided suitable force, contraction, and rise times for DCC applications and to evaluate how output force and contraction were affected by changes to variations in elastomeric material and braid angle.

Regarding use of the elastomeric actuators disclosed herein in direct cardiac compression (DCC), such as a treatment for end-stage heart failure, such treatment option does not require contact of the device(s) with the patient's circulating blood, unlike other treatment options (e.g., ventricular-assist devices (VADs)). This is advantageous because blood-contacting devices, such as VADs, are associated with thromboembolic events, hemolysis, immune reactions and infections.

The elastomeric actuators designed in accord with the present concepts can provide an atraumatic actuation strategy and provide load-length curves similar to human muscle. These elastomeric actuators were tested to investigate the effects of mesh geometry and elastomer material on force output, contraction, and rise time. The testing indicated that lower initial braid angles and softer elastomer materials provided the best force, contraction, and rise times (e.g., up to 50N of force, 24% contraction, and response times of 0.05s were achieved at 100 kPa). The tested elastomeric actuators exhibited low threshold pressures (<5 kPa) and high rupture pressures (138 kPa-720 kPa), which suggest safe operation for the DCC application. These results demonstrate that elastomeric actuators in accord with at least some of the present concepts can achieve forces, displacements, and rise times suitable to assist with cardiac function.

The disclosed devices, methods and systems relate generally to soft actuated materials adapted in view of, but not limited to, medical applications. This platform provides potential for simulation, rehabilitation, mechanical assistance or complete replacement of muscles or muscular organs. Specific, non-limiting, applications explored herein have focused on simulating the motion of the heart and developing an implantable direct cardiac compression device to assist with pumping in the failing heart.

The fully soft actuators described by way of example herein are premised on traditional McKibben actuators, but are significantly modified to exclude any rigid end fittings, to make them one monolithic structure, and to enable actuation with very low threshold pressures, making them safer for medical device applications. These actuators can then be disposed in or embedded in suitable elastomeric structure(s) (2-D and/or 3-D). For example, using a numerical simulation (e.g., ABAQUS finite element software), 3D structures can be designed to match the geometry and to replicate both physiological and pathological motion of an underlying biological component. By way of example, in one case study application of such actuators and active materials formed therefrom, an active left ventricle simulator was created and incorporated into a passive cardiac bench-top simulator, resulting in an active simulator which was still anatomically accurate with representative tissue material properties.

In at least some aspects of the present concepts, there is provided a biomimetic actuation system comprising a biomimetic actuation device comprising a flexible substrate, defining an apex and a base, bearing at least one soft actuator configured to change state from a first state to a second state upon introduction of a pressurized fluid to an internal volume of the at least one soft actuator. The biomimetic actuation system also includes a pressurized fluid source and a control system configured to selectively introduce pressurized fluid from the pressurized fluid source to the internal volume of the at least one soft actuator to cause the at least one soft actuator to change state from the first state to the second state and to selectively exhaust the pressurized fluid from the internal volume of the at least one soft actuator to cause the at least one soft actuator to change state from the second state at least to the first state. The at least one soft actuator comprises at least one soft actuator disposed curvilinearly along the substrate from the apex of the substrate toward the base of the substrate, at least one soft actuator disposed laterally or circumferentially along the substrate, or a combination of the at least one soft actuator disposed curvilinearly along the substrate and the at least one soft actuator disposed laterally or circumferentially along the substrate. The substrate is conformable for disposition about an object. Where provided, the at least one soft actuator disposed curvilinearly along the substrate is arranged about the object to deliver torsional forces to the object and where provided, the at least one soft actuator disposed laterally or circumferentially along the substrate is arranged about the object to deliver compressive forces or extensive forces to an object about which the substrate is disposed.

In at least some other aspects of the present concepts, a biomimetic actuation device comprises a flexible substrate, conformable for disposition about an object, defining an apex and a base, bearing at least one soft actuator configured to change state from a first state to a second state upon introduction of a pressurized fluid to an internal volume of the at least one soft actuator. The at least one soft actuator comprises at least one soft actuator disposed curvilinearly along the substrate from the apex of the substrate toward the base of the substrate, at least one soft actuator disposed laterally or circumferentially along the substrate, or a combination of the at least one soft actuator disposed curvilinearly along the substrate and the at least one soft actuator disposed laterally or circumferentially along the substrate. The at least one soft actuator disposed curvilinearly along the substrate, where provided, is arranged about the object to deliver torsional forces to the object and the at least one soft actuator disposed laterally or circumferentially along the substrate, where provided, is arranged about the object to deliver compressive forces or extensive forces to an object about which the substrate is disposed.

In at least some aspects, there is provided a biomimetic actuation device comprising a matrix of a first plurality of soft actuators disposed along a first direction and a second plurality of soft actuators disposed along a plurality of second directions, each of the soft actuators being configured to change state from a first state to a second state upon introduction of a pressurized fluid to an internal volume of the soft actuator, wherein the first direction and at least some of the plurality of second directions form one of an acute or oblique angle with respect to one another, and wherein the matrix is conformable for disposition about a curved-object and, so disposed, the first plurality of soft actuators are disposed to deliver compressive forces or extensive forces to the curved-object upon actuation and the second plurality of soft actuators are disposed to deliver at least torsional forces to the curved-object upon actuation. In such configuration, the matrix of actuators is self-supporting and does not require substrates.

In at least some aspects of the present concepts, a soft actuator comprises an elongated flexible bladder defining an expandable chamber along an axial direction between a first end and a second end, the elongated flexible bladder being adapted to substantially axially displace between a deflated state and an inflated state, displacing the first end toward the second end in the inflated state and a braided sheath member adapted to constrain radial expansion of the expandable chamber during inflation of the expandable chamber from the deflated state to the inflated state, the braided sheath member comprising a first braid angle at the first end, a second braid angle at the second end, and at least a third braid angle between the first end and the second end. A tube is attached to one of the first end or the second end and extending to communicate with an interior volume of the elongated flexible bladder. The braided sheath member is bonded to the elongated flexible bladder and at least one of the first braid angle or the second braid angle neutral braid angle comprises a neutral braid angle or a braid angle close to the neutral braid angle, wherein the third braid angle is different from at least one of the first braid angle and the second braid angle.

In another aspect of the above soft actuator, a soft plug seals one or, or both of, the first end and/or the second end.

In another aspect of the above soft actuator, the first braid angle and the second braid angle are substantially equal.

In another aspect of the above soft actuator, the first braid angle, the second braid angle, and the third braid angle are all different from one another.

In another aspect of the above soft actuator, the third braid angle itself comprises a plurality of regions of different braid angles.

In another aspect of the above soft actuator, the third braid angle is varied along a length of the braided sheath member so as to impart to the soft actuator a bending motion, a twisting motion, or a combination of a bending motion and a twisting motion, upon displacement of the first end toward the second end in the inflated state.

In another aspect of the above soft actuator, the braided sheath member is bonded to the elongated flexible bladder using elastomer.

In another aspect of the above soft actuator, the elongated flexible bladder is formed from a low stiffness elastomer.

In another aspect of the above soft actuator, the soft actuator is actuated by a control system configured to introduce fluid into the interior volume of the elongated flexible bladder to generate a predetermined contractile force for a predetermined period of time and to exhaust the fluid from the interior volume of the elongated flexible bladder to enable extension of the elongated flexible bladder to an initial position.

In another aspect of the above soft actuator, the fluid comprises one of air, nitrogen, helium, carbon dioxide, saline, contrast, or water.

A process for forming a soft actuator comprises the acts of disposing a mesh having a proximal end and a distal end over an elongated flexible tube or elongated flexible bladder having a proximal end and a distal end, covering a distal first portion of the mesh to maintain an orientation of the mesh, leaving a second portion of the mesh exposed, and securing a proximal portion of the exposed second portion of the mesh relative to the elongated flexible tube or elongated flexible bladder, leaving a distal portion of the exposed second portion of the mesh free to move relative to the elongated flexible tube or elongated flexible bladder. The process further includes the acts of compressing the exposed second portion of the mesh by translating the distal portion thereof toward the proximal portion thereof to deform the exposed mesh and heating the exposed mesh to cause the mesh to alter a braid angle of the exposed mesh relative to the covered first portion of the mesh.

In another aspect of the above process for forming a soft actuator, the act of covering a distal first portion of the mesh to maintain an orientation of the mesh comprises covering the distal first portion of the mesh with a heat shrink material.

In another aspect of the above process for forming a soft actuator, the act of securing the proximal portion of the exposed second portion of the mesh relative to the elongated flexible tube or elongated flexible bladder comprises covering the proximal portion of the exposed second portion of the mesh with a heat shrink material.

In another aspect of the above process for forming a soft actuator, the process further comprises the act of bonding the mesh to the elongated flexible tube or elongated flexible bladder using an elastomer.

In another aspect of the above process for forming a soft actuator, the elastomer bonding the mesh to the elongated flexible tube or elongated flexible bladder fully encapsulates the mesh.

In another aspect of the above process for forming a soft actuator, the mesh is disposed over an elongated flexible tube.

In another aspect of the above process for forming a soft actuator, the process further comprises the act of closing the proximal end and the distal end of the elongated flexible tube by molding elastomer over the proximal end and the distal end of the elongated flexible tube.

In some aspects of the present concepts, a cardiac simulator comprises a substrate, formed to at least generally simulate a topography of at least a portion of a heart, comprising a plurality of soft actuators configured to change state from a first state to a second state upon introduction of a pressurized fluid to an internal volume of each of the plurality of soft actuators, a pressurized fluid source and a control system configured to selectively introduce pressurized fluid from the pressurized fluid source to the internal volume of the plurality of soft actuators to cause the plurality of soft actuators to change state from the first state to the second state and to selectively exhaust the pressurized fluid from the internal volume of the plurality of soft actuators to cause the plurality of soft actuators to change state from the second state at least to the first state.

In at least some aspects of the cardiac simulator, above, the pressurized fluid source comprises a pump or compressor and a fluid reservoir and the pressurized fluid may comprise a liquid (e.g., saline) or a gas (e.g., air, helium, etc.).

In at least some aspects of the cardiac simulator, above, the plurality of soft actuators each comprise an elongated flexible bladder defining an expandable chamber along an axial direction between a first end and a second end, the elongated flexible bladder being adapted to substantially axially displace between a deflated state and an inflated state, displacing the first end toward the second end in the inflated state.

In at least some aspects of the cardiac simulator, above, at least some of the plurality of soft actuators are different from one another in at least one of size, internal volume, force output, and contractile distance between the first state and second state.

In at least some aspects of the cardiac simulator, above, the substrate is formed to at least generally simulate a topography of one or more of a left ventricle, right ventricle, left atrium, right atrium.

In at least some aspects of the cardiac simulator, above, the substrate is in the form of a sleeve, a band, or a cup.

In at least some aspects of the cardiac simulator, above, at least some of the plurality of soft actuators are configured to impart a rotational force upon actuation.

In at least some aspects of the cardiac simulator, above, at least some of the plurality of soft actuators are configured to impart a contractile force upon actuation.

BRIEF DESCRIPTION OF THE FIGURES

FIGS. 1(a)-1(b) depict, respectively, a pneumatic artificial muscle and parameters relevant thereto wherein an input pressure is zero (left) and positive (right) (wherein the actuator shortens and expands radially), as well as a plot of radial expansion and longitudinal shortening or contraction percentages with respect to pressure.

FIG. 2 shows a free body diagram of half of a direct cardiac compression device portion in accord with at least some aspects of the present concepts.

FIGS. 4(a)-4(b) show, respectively, a process diagram for varying the mesh braid angle in accord with at least some aspects of the present concepts and a magnified image of a modified braid in accord with at least some aspects of the present concepts.

FIGS. 12(a)-12(e) show, in accord with at least some aspects of the present concepts, fabrication steps for a left ventricle prototype or DCC device in accord with at least some aspects of the present concepts.

FIGS. 14(a)-14(c) show, in accord with at least some aspects of the present concepts, (a) (left) heart with opposing rotation at apex (counter-clockwise) and base (clockwise) and (right) sub-epicardial and sub-endocardial fibers arranged in opposing helices with the sub-epicardial fibers dominating overall motion due to a larger radius and greater moment arm; (b) physical prototype at various pressure increments juxtaposed with mesh showing deformation at corresponding pressures and displacement contour plot in isometric view showing the displacement (U) of the ventricle at corresponding pressures; (c) (left) apical rotation (average of 4 markers in apical plane) for FE and physical model when LV is supported at the base compared to clinical values and (right) apical and basal rotation (average of 4 markers) when LV is supported by flexible band between base and apex compared to clinical values.

FIGS. 26(a)-26(c) depicts aspects of a control system suitable for the DCC devices and actuator-based devices disclosed herein.

FIGS. 27(a)-27(b) show aspects of control schemes for at least some embodiments of DCC devices in accord with at least some aspects of the present concepts.

Figure 3A:
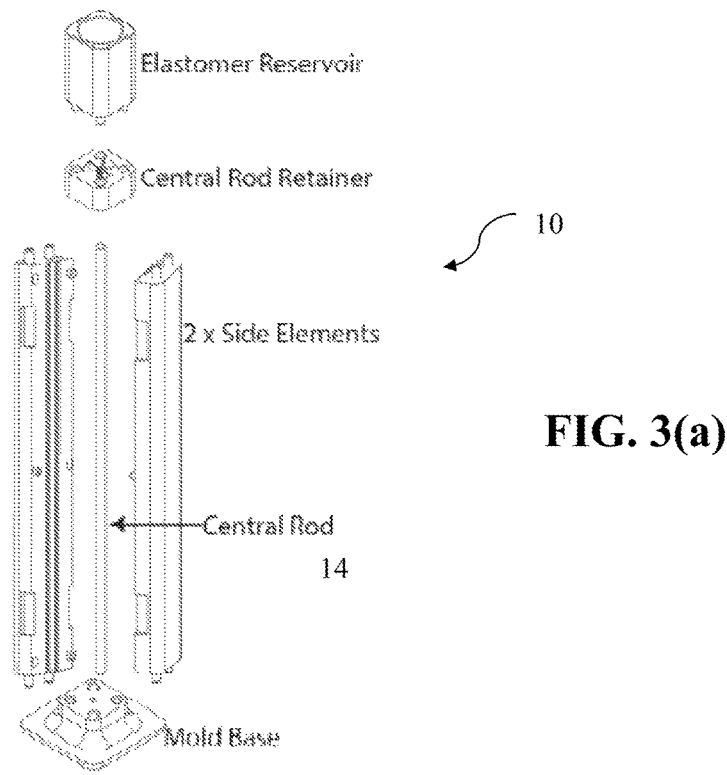
FIGS. 3(a)-3(b) respectively show a device for fabrication of pneumatic artificial muscles in accord with at least some aspects of the present concepts and steps in a fabrication processes for pneumatic artificial muscles in accord with at least some aspects of the present concepts.

While the invention is susceptible to various modifications and alternative forms, specific embodiments are shown by way of example in the drawings and will be described in detail herein. It should be understood, however, that the invention is not intended to be limited to the particular forms disclosed.

DETAILED DESCRIPTION OF THE ILLUSTRATED EMBODIMENT

The force produced by a pneumatic artificial muscle (PAM) depends on its internal pressure and its contraction, but not its initial length. Force increases linearly with increasing internal pressure and decreases with increasing contraction, thus at least two sets of tests are required to characterize the force output of the muscle. Using energy conservation, an expression for the force output of a PAM can be derived:

$$F = -P \, dV/dl \quad (1)$$

where F is output force, P is input pressure, dV is change in the actuator's internal volume and dl is the change in the actuator length.

For a McKibben PAM, assuming a thin wall and neglecting friction and effects of bladder elasticity, the output force relation is as follows:

$$F = P \cdot \frac{\pi D_0^2}{4}(3\cos^2\theta - 1) \quad (2)$$

where $\theta$ is the braid angle (see FIG. 1(a)) and $D_O$ is the diameter of the mesh at a braid angle of 90 degrees.

Change in the length, $\Delta l$, of the actuator shown in FIG. 1(a) is given by:

$$\Delta l = l_O \cdot \epsilon \quad (3)$$

where $l_O$ is initial length and $\epsilon$ is contraction. Contraction depends on internal pressure and output force and increases with increasing pressure and decreases with increasing force. Unlike force, contraction has a theoretical maximum which occurs when the braid angle $\theta$ is so large that the expression for force output in Eq. (4) equals zero. This angle, $\theta_{MAX}$ is called the neutral braid angle or the "magic angle" and is equal to 54.7°. When the mesh reaches this braid angle, no more axial contraction or radial expansion can occur, as is known to hose manufacturers, and the neutral angle is used in most fiber reinforced hose for this reason. In the elastomeric actuators (e.g., PAMs) developed in accord with the concepts disclosed herein, the braid angle of the ends were set close to the neutral braid angle (e.g., within 3° of the neutral braid angle, and still more preferably within 2° of the neutral braid angle, and still more preferably within 1° of the neutral braid angle) or at the neutral braid angle to prevent expansion of the ends.

In view of the principle of operation of the elastomeric actuators, described above with respect to FIG. 1(a), the longitudinal contraction and radial expansion of a PAM in accord with at least some aspects of the present concepts were characterized and plotted as a function of input pressure (FIG. 1(b)). As shown in FIG. 1(b), the majority of the contraction/expansion desirably occurs at low pressures (e.g., below about 10 psi) due to the low durometer of the inner elastomeric tube.

The force requirements of the elastomeric actuators in accord with at least some aspects of the present concepts can be estimated using a simple model of a hemispherical direct cardiac compression (DCC) device (see, e.g., reference numeral 100 in FIGS. 16(a)-(e)) cupped around the bottom of a spherical heart. The free body diagram of a cross section passing through the center of the model DCC device is shown in FIG. 2. If the DCC device 100 and the heart are in equilibrium, the tension, T, required to apply the pressure $P_{assist}$ to the heart is $$T = \frac{P_{assist} \cdot A_x}{2} \quad (4)$$

where $A_x$ is the projected cross-sectional area of the device. In a study using a cup-shaped pneumatic DCC device 100 around a totally arrested canine heart, assistance pressure of 140 mmHg (18.7 kPa) was needed to restore pumping function. Using the above hemispherical cup model and assuming a diameter equal to a typical transverse heart diameter in adult males (13 cm), this pressure would correspond to a tensile force of roughly 60N. At lower pressures, cardiac function can be augmented instead of replaced. An assistance pressure of 20 mmHg (2.7 kPa) applied using a cup-shaped assist device has been shown to significantly increase the ejection fraction of failing hearts in live sheep. This assistance pressure roughly corresponds to a tension of only 10N using Equation (4). These first order estimates suggest that a tension roughly in the range of 10N to 60N is suitable for DCC. In a DCC device 100 in accord with at least some aspects of the present disclosure, the total wall tension would be produced by multiple elastomeric actuators placed in the wall of the device in a transverse orientation. Actuation with more elastomeric actuators in parallel allows the force to be more distributed and is believed to be gentler on the heart. To enable the use of more actuators in parallel, the diameter of the actuators was designed to be as small as was feasible with the available fabrication techniques.

Required contraction can be estimated using the measure of cardiac function called fractional shortening (FS), a measure of the percent change in the length of a cardiac dimension between diastole (expansion) and systole (contraction). In cases of left ventricular dysfunction, FS is less than or equal to 25%. The actuators developed here must provide similar or better percent contraction to be useful in DCC.

In accord with at least some aspects of the present concepts, the response time of a direct cardiac compression device is desired to be similar to the contraction time of the human heart. Systole occurs in about 0.3 seconds in humans, so rise times much less than 0.3s are desired in order to keep pace with the heart. If the contraction time of a DCC device 100 (see, e.g., FIGS. 16(a)-16(e)) were much longer than systole, filling of the heart's ventricles, which occurs after systole, could be impeded.

Figure 3B:
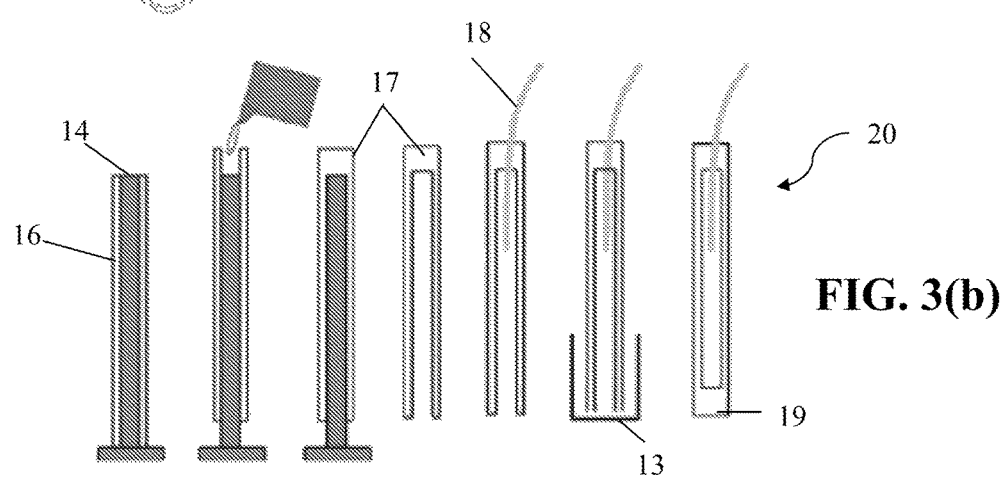

FIGS. 3(a)-3(b) respectively show a device 10 for fabrication of pneumatic artificial muscles 20 in accord with at least some aspects of the present concepts and steps in a fabrication processes for pneumatic artificial muscles in accord with at least some aspects of the present concepts. In accord with one aspect of the present concepts, as shown in steps (a)-(b) of FIG. 3(b), the elastomeric actuators 20 (e.g., pneumatic artificial muscles (PAMs)) are formed by first placing formed tubing 16 of a suitable diameter around a rod 14 of substantially similar diameter and extending the tubing past the end of the rod by about 2 cm, following which a mixed prepolymer is poured into the exposed end of the tubing (step (b) in FIG. 3(b)). The 2 cm plug 17 is cured (e.g., at 60° C. for one hour). Next, in step (c) of FIG. 3(b), an air supply line 18 is inserted into the plugged end 17 (e.g., using a metal stylet). The remaining open end of the tube 16 is dipped into a basin 13 of mixed prepolymer to a depth of 2 cm and cured (e.g., at 60° C. for 1 hour) to form the second plug 19 and thereby the elastomeric actuator 20. During the dipping, the outer wall of the elastomer tubing 16 is covered with PTFE tape to prevent the outer walls from bonding to the prepolymer in the basin 13. In one aspect, the finished elastomeric actuators 20 were 14 cm long with a 10 cm active length, outer diameter of about 8 mm-14 mm, and wall thickness of about 1 mm-2 mm.

In at least some aspects of the present concepts, ends of the actuators 20 are optionally reinforced with plugs of a stiffer elastomer (e.g., Elastosil M4601) to help mitigate air leakage and/or to assist with retention of the air supply line. In one aspect, this reinforcement is accomplished by injecting the reinforcing elastomer into the bottom end of the actuator 20 and curing the reinforcing elastomer while maintaining the actuator in an upright position (e.g., cured for one hour at 60° C.). Following curing, the actuator 20 is flipped and the procedure repeated by injecting the reinforcing elastomer into the bottom end of the actuator and curing the reinforcing elastomer while the actuator it is positioned in an upright position. The air supply line 18 is then inserted through one of the reinforced ends. Alternatively, the reinforcing elastomer is injected into the bottom end of the actuator 20 (the end not having the air supply line 18) and the actuator is cured in an upright position (e.g., cured for one hour at 60° C.). Following curing, the actuator is flipped and the procedure repeated by injecting the reinforcing elastomer into the bottom end of the actuator 20 having the air supply line 18, being careful not to inject the reinforcing elastomer at or above the level of the air supply line opening, and curing the actuator while it is positioned in an upright position.

A mold 10, such as that depicted in FIG. 3(*a*), may be used to form the tubing 16 and may further be used to complete at least some of the acts depicted in FIG. 3(*c*) (e.g., acts (a)-(c)). The mold 10 may comprise any mold suitable for forming tubes from an elastomer. In one aspect, the mold 10 is a 3D printed mold (Objet Connex 500, Stratasys)) and the tubes are formed from an elastomer (Ecoflex 00-30, Smooth-on Inc.). In at least some aspects of the present concepts, the tubing 16 used to form the actuator 20 is itself formed by injecting a mixed prepolymer (e.g., Ecoflex 00-30 (Smooth-on Inc.)) through a hole (e.g., 4 mm) in a wall of the mold 10 into a cylindrical cavity defined by the assembled mold, the cavity of the mold in turn defining the outer diameter and length of the formed actuator (e.g., outer diameter of 3.5 mm). Although the example relates to a low stiffness elastomer, a higher stiffness elastomer (e.g., Shore A-28, Elastosil M4601, Wacker Chemie AG) may optionally be utilized. In some aspects of the present concepts, the material(s) used for the actuators 20 and substrate in which the actuators are disposed are selected to present similar properties to that of the biological tissue to which the actuators are to be applied. For example, in a DCC application, Ecoflex has a reported modulus of 125 kPa, which is within the range of reported values for myocardial tissue (203.3±55.6 kPa for healthy myocardium and 117.3±37.0 kPa for infarcted myocardium).

In accord with the actuators 20 fabricated in accord with aspects of the present concepts, the diameter of the elastomeric tubing 16 was made as small as possible to enable the use of more actuators (e.g., closer spacing of actuators) disposed at an angle relative to one another). A minimum outer diameter of 8 mm and a wall thickness of 2 mm was selected for the tested actuators 20, which were fabricated in-house, for the reason that molds for narrower tubing were difficult to fill using gravity alone, but these dimensions are not limitations on the concepts herein and were, instead, selected merely for fabrication convenience.

Once the cavity in the mold had been completely filled, a central rod 14 (e.g., a 1.6 mm diameter stainless steel rod) is slowly inserted through an upper central rod retainer and into the mold base to form an inner diameter of 1.6 mm in the actuator tubing. The mold 10 is then degassed and cured under pressure, temperature and time constraints appropriate for the elastomer (e.g., degassing in a vacuum chamber at 10 kPa absolute pressure for 10 minutes, followed by curing for 1 hour in a pressure chamber heated to 60° C.). The elastomeric tubing 16 is then demolded and advanced along the central rod 14 to permit closure of the open end of the tubing 16 and curing thereof, as indicated, for example, in FIG. 3(*b*).

Advantageously, but optionally, a mesh is integrated with the tubing 16 or actuator 20 to enhance tensile strength and a force generation capability of the actuator. To fabricate actuators 20 utilizing mesh in accord with at least some aspects of the present concepts, one fabrication method comprises acts of molding elastomeric tubing, preparing a mesh, bonding the mesh to the tubing, and then sealing the ends. For example, in one aspect, a section of mesh was cut to a length of 75 mm and its ends were heated with a flame and brass forming tool to prevent fraying at one end and to close the mesh at the other end. The mesh was placed over the molded tube. The uncapped end was advanced over a length of air supply tube (McMaster Carr Silicone tubing ⅛" tubing 5236K502) until it extended 10 mm inside the molded tube. Nylon thread or suture material was used to secure mesh and molded tube onto the air supply tube. The assembly was roll-coated with a thin layer of Ecoflex excess material was removed. Finally, the assembled actuator was cured with a heat gun and left for two hours for full curing of the polymer. The mesh and inner tube are then advantageously covered with an additional layer of elastomer.

In at least some aspects of the present concepts, before molding mesh over the elastomeric tubing 16, the mesh was locally modified to resist expansion at its ends and to prevent fraying. This was achieved by locally heating the mesh (expandable sleeving, Techflex, Inc.) and increasing the braid angle. FIG. 4(*a*) shows acts that could be performed to form an actuator 20 integrating mesh in accord with at least some aspects of the present concepts. The mesh 24 was placed over a steel rod 22 for support and the region of the mesh that was not being modified was covered with heat shrink tubing 26 to maintain the orientation of the fibers underneath. The end of the mesh sleeve was held to the rod with a ring of heat shrink tubing to prevent fraying when the ends were heated and compressed.

In at least some aspects, a plurality of soft actuators are comolded.

As shown in FIG. 4(*a*)(4), the exposed mesh sleeve was compressed by sliding the two heat shrink protected areas together. When the exposed mesh 29 was compressed, it bulged to a larger diameter, but collapsed back to the diameter of the rod when heated to form mesh having a second general braid angle different than the mesh 28 having a first braid angle. After the new configuration was achieved, the fibers were allowed to cool to lock the new shape into place. To verify that the braid angle was close to the neutral angle, manual expansion of the mesh was attempted and the resistance to expansion was assessed qualitatively. A mesh 30 that was modified using the above procedure is shown in FIG. 4(*b*). It is to be noted that, in lieu of or in addition to the mesh, other meshes, fibers, paper, etc. can be incorporated into the actuators 20 to constrain movement of the actuators in one or more states.

Different global braid angles were achieved by using different meshes between actuators or by using the same mesh and slightly changing the diameter of the actuator because diameter and braid angle are coupled. Since the braids for the fabricated and tested actuators 20 were not made in-house, differences in mesh construction besides braid angle, like weave density, could not be controlled. The braid angle of each actuator was estimated using a microscope and the measurements for the actuators are given in Table 1.

TABLE 1

BRAID MEASUREMENTS.

| Mean $\theta_1$ (deg) | St Dev. (deg) | Initial diameter (mm) |
|---|---|---|
| 22.6 | 0.8 | 8 |
| 28.6 | 0.7 | 8 |
| 31.7 | 1.1 | 8 |
| 39.5 | 1.6 | 10 |
| 45.1 | 0.5 | 12 |

Once the mesh was prepared, it was bonded to the outer wall of the elastomeric tube with another layer of elastomer. This was done by putting the mesh 30 over the tubing 16 and dipping both into a basin of mixed prepolymer (e.g., rotating the tubing 16 having the mesh 30 disposed thereover in a cylindrical basin having the mixed prepolymer therein). When the tube was removed from the basin, the tube was blown with hot air while being rotated to evenly spread and cure the elastomer. If the ends of the actuator 20 were not previously closed, they could then be closed by molding 2 cm long elastomer plugs.

Figures 5A, 5B:
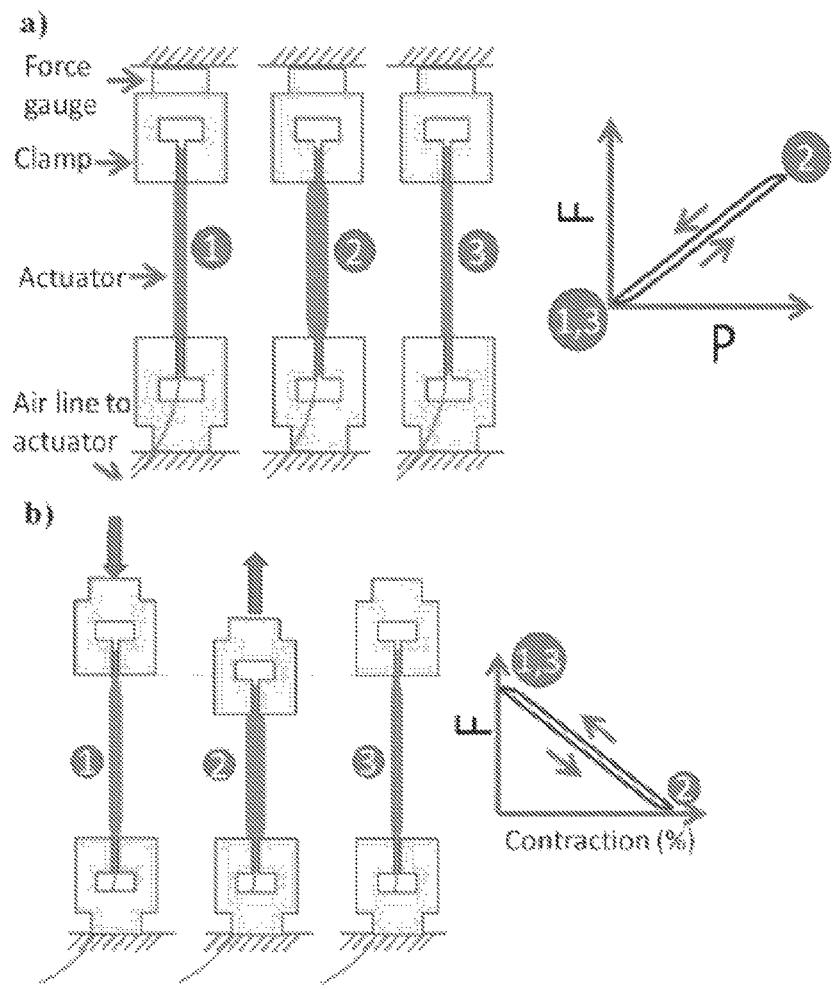
FIGS. 5(a)-5(b) show, respectively, a schematic of a test procedure used for isometric contraction and constant pressure contraction of pneumatic artificial muscles in accord with at least some aspects of the present concepts.

The actuators were characterized to determine whether they provided the appropriate force, contraction, and rise time for use in a DCC application. Isometric contraction tests were conducted to determine output force as a function of internal pressure while actuator length was held constant, and constant pressure contraction tests were conducted to measure force as a function of contraction while pressure was held constant. The isometric contraction test was conducted quasistatically and dynamically. Additionally, failure testing was conducted to determine the failure mode and pressure of the actuators For the isometric contraction test, the force output was measured using a 2 kN load cell (±4N accuracy) and pressure was measured using a pressure transducer (±5 kPa accuracy) attached to the air supply line for the actuators 20. From these measurements, a force-pressure curve was generated. FIG. 5(a) shows the test procedure. The pressure input was different in the quasistatic and dynamic testing. For the quasistatic response, the input pressure was slowly (T≅60s) ramped from 0 to 103 kPa and back to 0 kPa using a pressure regulator. For the dynamic response a solenoid valve (2.4 mm orifice, 4-16 milliseconds response time) was used to quickly deliver air at 103 kPa from an accumulator (4.16 L) to the actuators through about 1 m of tubing (ID=3.2 mm). A regulator was used to fill and continuously regulate the pressure in the accumulator. For the constant pressure contraction test, the force and contraction were measured using a method previously used to characterize elastomeric actuators. FIG. 5(b) shows the experimental procedure. Tests were run at pressures of 34 kPa, 69 kPa, and 103 kPa and an accumulator (4.16 L) was again used to maintain constant pressure. The contraction was varied by moving the actuator ends while the reaction force at the supports was measured using a 2 kN load cell (±4N accuracy). The actuator was allowed to contract until no load was measured at the supports (the "maximum contraction") and was then stretched back to the original length. Percent contraction was calculated by dividing displacement by the initial active length (10 cm). The contraction frequency was near physiological rates. A normal resting heart rate ranges from about 0.7 Hz-1.3 Hz, whereas the actuators were tested at ram speeds consistent with about 0.5 Hz contraction frequency.

Failure testing was also performed on the actuators 20. Pressure was delivered to each actuator 20 using its air supply line 18 and was slowly increased until failure. The tests were conducted with no load attached to the actuator 20. A pressure sensor (accuracy: ±5 kPa) was used to measure the pressure during the test. The tests were filmed with a pressure sensor next to the muscle to enable confirmation of the pressure at the onset of failure.

Figure 6:
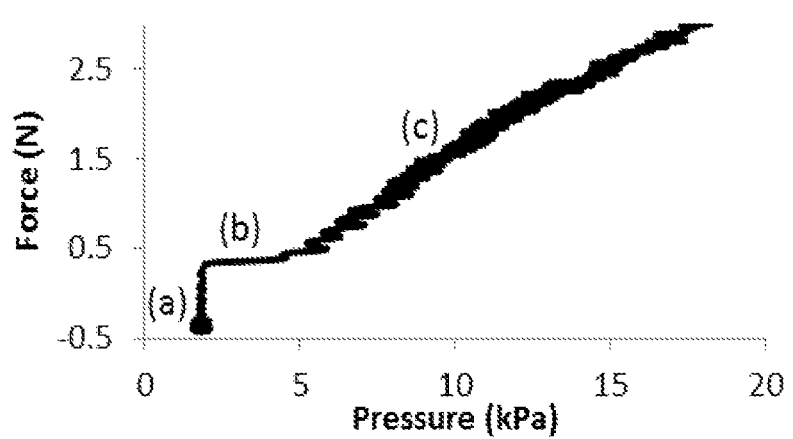
FIG. 6 shows a force vs. pressure curve for pneumatic artificial muscles, in accord with at least some aspects of the present concepts, at low pressure.

The force-pressure curves from the quasistatic isometric contraction test were used to measure the threshold pressure of the actuators and to examine the effects of initial braid angle and elastomeric material on the force output as a function of pressure. The low pressure region of the force-pressure curves was used to attempt to identify a threshold pressure. A typical force-pressure curve at low pressures is shown in FIG. 6. As the figure shows, the force-pressure curve is vertical in region (a) because an increase in force was measured before an increase in pressure was measured. In region (b), the pressure increase is detected and the pressure appears to increase without much change in force. After a pressure of about 5-7 kPa, the measured force increases linearly with measured pressure (region (c)). This pattern was nearly identical across all actuators 20. Region (a) is clearly an artifact because force cannot be developed by the actuators 20 without pressure. Since the force increase was detected before any pressure, no pressure threshold could be detected for any of the actuators 20, but factoring in the accuracy of the sensor (±5 kPa), the threshold pressure of the actuators can be said to be below 5 kPa. This threshold pressure is an order of magnitude lower than those of McKibben air muscles tested in the literature.

Figures 7A, 7B:
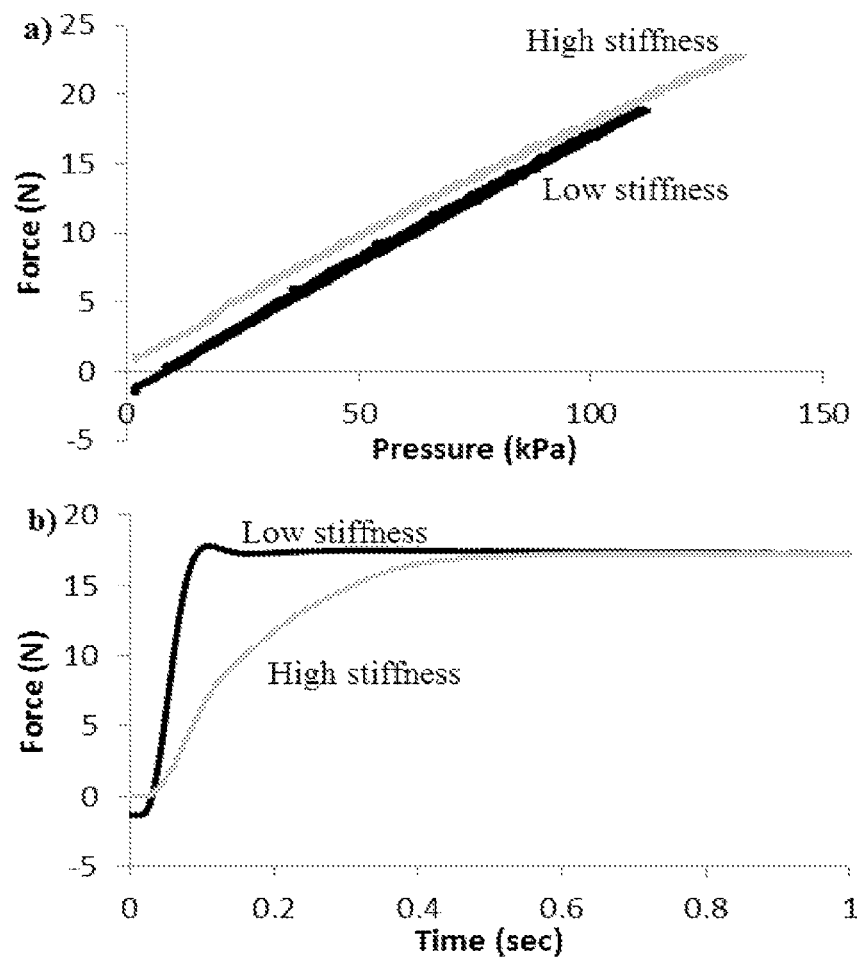
FIGS. 7(a)-7(b) show isometric contraction curves, quasistatic test results and dynamic test results, respectively, for pneumatic artificial muscles comprising elastomers of different stiffness in accord with at least some aspects of the present concepts.

In addition to identifying the threshold pressure, the effect of the elastomeric material on force output was assessed by comparing the force-pressure curves of two actuators that differed only in elastomeric material. The curves of the actuators 20 made from low stiffness (Ecoflex 00-30) and high stiffness (Elastosil M4601) elastomer are shown in FIG. 7(a). The slopes of the curves were similar between the muscles; the low stiffness actuator has a slope only 4% greater than the high stiffness actuator. The similarity between the curves was expected because deformation was prevented in this test, so almost no energy went to deforming the elastomer and therefore the different elasticities had little effect.

The dynamic responses of the two actuators 20 are compared in FIG. 7(b). The actuator 20 of the stiffer elastomer had a much longer rise time (0.28s vs. 0.05s). Based on the imposed requirement of a rise time much less than 0.3 seconds, the actuator 20 made of the softer elastomer contracted at a rate suitable for direct cardiac compression, but the actuator made of the stiffer elastomer did not.

Figures 8A, 8B:
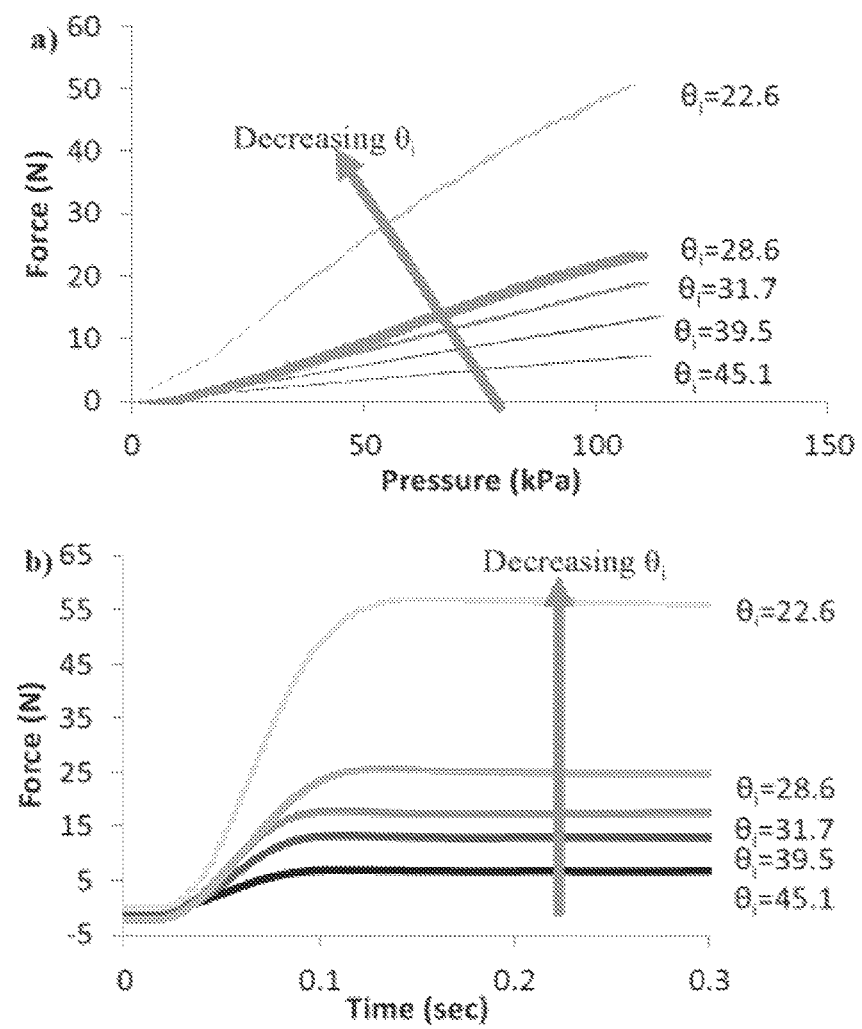
FIGS. 8(a)-8(b) show isometric contraction curves, quasistatic test results and dynamic test results, respectively, for pneumatic artificial muscles in accord with at least some aspects of the present concepts comprising elastomers of different braid angles.

The force-pressure curves from the isometric contraction test were also used to investigate the effects of initial braid angle on force output. The force-pressure curves of five artificial muscles that differ in initial braid angle are shown in FIG. 8(a). All of the actuators 20 were made of the low stiffness elastomer. For the actuators with an increased initial diameter, the effect of an increased braid angle, which is decreasing force, dominated the effect of the increased diameter, which is increasing force. The slope of the force-pressure curve increased with decreasing initial braid angle, $\theta_i$. All the actuators except the one with the highest $\theta_i$ were able to develop at least 10N of force at 100 kPa. This is suitable for DCC because even a single actuator could deliver force in the desired 10-60N range at pressures of 100 kPa.

The dynamic responses of the actuators 20 are also compared in FIG. 8(b). All the actuators had a rise time of approximately 0.05s. This suggests that initial braid angle does not have much effect on rise time and that the contraction times are suitable for utilization in DCC applications in accord with the present concepts.

Figure 9A:
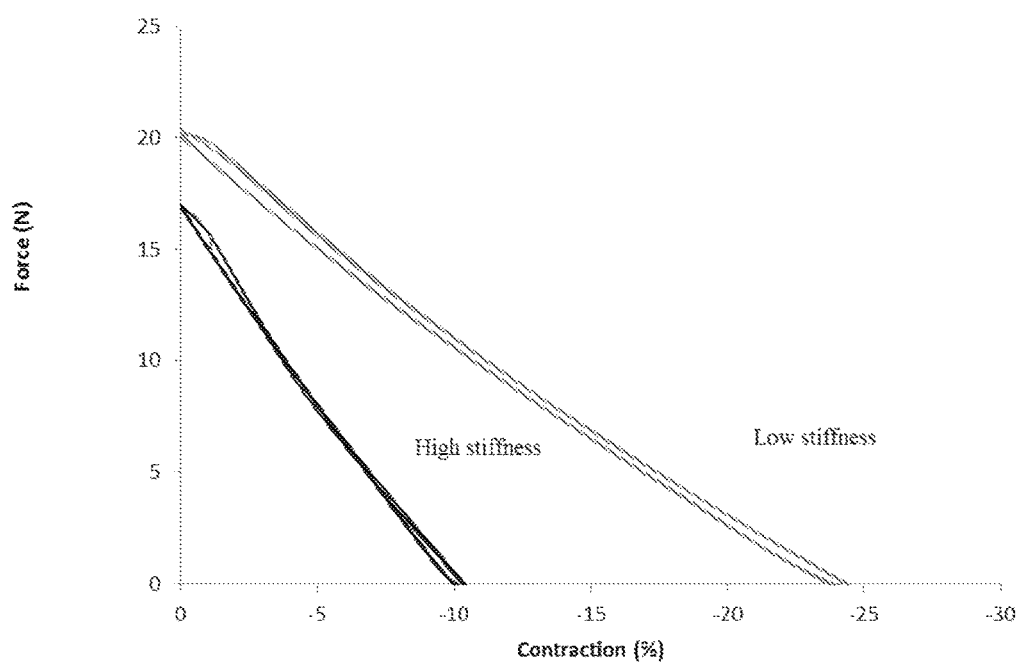
FIGS. 9(a)-9(b) show, respectively, the effect of elastomeric material on the force-contraction curve and the effect of initial braid angle on the force-contraction curve in accord with at least some aspects of the present concepts.

The constant pressure test results were used to assess whether the actuators produced suitable contraction for DCC and to evaluate the effect of elastomeric material and initial braid angle on contraction. The effect of different elastomeric materials was measured by testing two actuators that differed in elastomer stiffness. Force-displacement curves of the actuators 20 made of the low stiffness (Shore OO-30) and high stiffness (Shore A-28) elastomers are shown in FIG. 9(a). As predicted, the force decreased monotonically as contraction increased for both actuators. Also, the curves exhibited low hysteresis (~1N high, and 1% wide) compared to other McKibben PAMs, possibly due to lower friction. The use of the stiffer elastomer reduced maximum force and contraction, but the maximum contraction was reduced much more than maximum force. Based on the imposed requirement of roughly 25% contraction, the contraction of the low stiffness actuator 20 appears suitable for DCC in accord with aspects of the present concepts, but the contraction of the high stiffness actuator does not appeared to suitable for DCC, but potentially could be suitable for other applications.

Figure 9B:
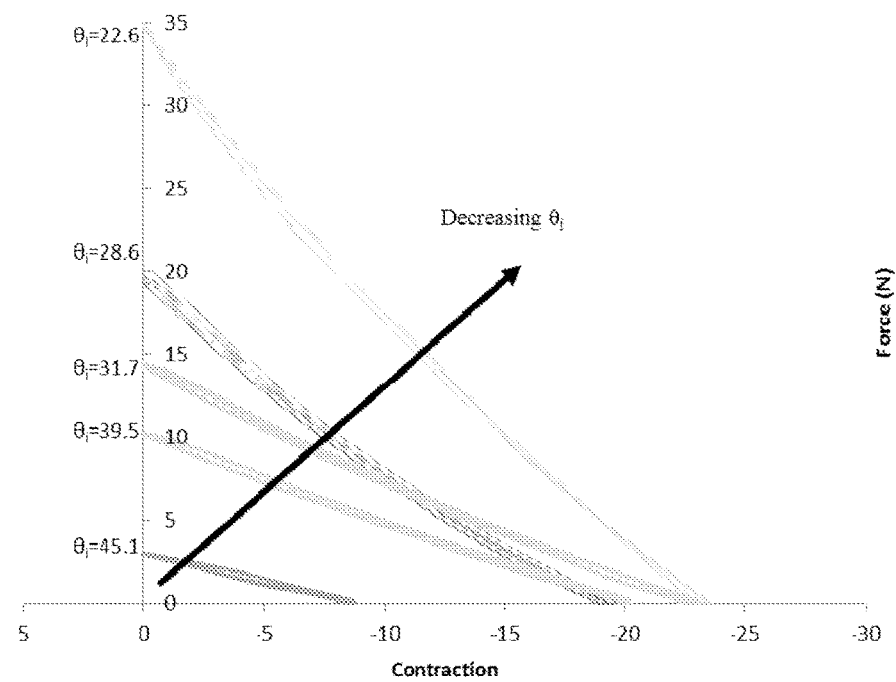

The force-displacement curves of five artificial muscles that differed in braid angle are shown in FIG. 9(b). All of the curves shown in the figure were taken at a pressure of 69 kPa. Each of the curves is monotonically decreasing and roughly linear. Again, there was small hysteresis (~1N high and 1% wide). The maximum contraction and maximum force tended to increase with a decreasing initial braid angle, but it seems that the effect on maximum contraction was diminishing after $\theta_i$=39.5°.

The actuator 20 with $\theta_i$=28.6° was an outlier because it had a lower maximum contraction than two actuators with a higher braid angle. This may be explained by the difference in mesh properties besides the braid angle, namely the weave density. Davis showed that higher fiber density caused a lower maximum contraction. The two actuators with the lowest braid angle ($\theta_i$=28.6°, $\theta_i$=22.6°) had a higher weave density than the rest of the actuators, which had the same weave density.

In all of the actuators 20, a trade-off between force and contraction is apparent. It is difficult for the actuators 20 to produce both high force and high contraction at once because force decreases with increasing contraction. However, force can be increased by adding more actuators in parallel which might enable more force to be sacrificed for contraction.

The actuators 20 with lower initial braid angles were able to deliver greater force and contraction, so the best design seems to be one with the lowest possible initial braid angle. Because radial expansion increases with decreasing initial braid angle and space in the pleural cavity is limited, the maximum allowable radial expansion should be determined to define the lowest feasible initial braid angle.

The first failure mode of the actuators 20 made of the less stiff elastomer was that the air supply line slipped out. The line was ejected at 138 kPa-228 kPa for three specimens made of the softer elastomer (Ecoflex 00-30). The air supply line was not ejected for the four actuators made of high stiffness elastomer (Wacker M4601), but the plug opposite the air supply line failed. Failure occurred at 270 kPa, 600 kPa, and 720 kPa. All of these ruptures pressures are significantly higher than the operating pressure of 100 kPa. Accordingly, in at least some aspects, a hybrid actuator would advantageously comprise a combination of soft elastomer in at least a middle portion of the actuator 20, with a stiffer elastomer being utilized or added to a portion of the actuator adjacent the air supply line 18 to prevent the disconnection of the line and raise the failure pressure of the soft actuators. The variation in rupture pressure was high, especially for the stiffer actuators, so testing of a larger sample size is needed to identify the factors that cause this variation.

The experimental data validated that the tested actuators 20 (pneumatic artificial muscles (PAMs)) have the ability to deliver suitable forces, contractions, and rise times for direct cardiac compression (DCC) in the pressure range of 0-100 kPa. These actuators 20 also have threshold pressures significantly lower than traditional McKibben PAMs, which enables successful operation in a pressure range similar to existing direct cardiac compression devices.

The experimental results indicate that elastomeric material and initial braid angle greatly affect actuator 20 performance. A softer elastomer enabled greater contraction and a much faster response time while a lower initial braid angle increased force output and maximum contraction.

Thus, actuators 20 in accord with at least some of the present concepts are made out of a soft elastomer comprising a mesh having a low initial braid angle. These elastomeric actuators have been shown to provide suitable force, contraction, and rise times for DCC applications.

Accordingly, in accord with at least some aspects of the present concepts, a DCC device comprises a plurality of soft elastomer actuators 20 (e.g., PAMs), comprising a mesh having a low initial braid angle, integrating into a soft, compliant substrate (e.g., elastomer, textile, polymer, tissue, etc.) that can be placed against or around the heart. The soft, compliant substrate of such a DCC device 100 (see, e.g., FIGS. 16(a)-(e)) may assume any form including, but not limited to one or more continuous or discontinuous sleeve(s), cup(s), band(s), or patch(es) of any suitable shape or size. By way of example, a DCC device 100 having the general form of a cup (e.g., a generally spheroidal shape, a generally ellipsoidal shape, a generally elliptic parabolic shape, etc.) and may comprise an opening at an apex or may comprise one or more openings. The DCC device comprising soft actuators 20 in accord with at least some aspects of the present concepts (e.g., soft actuators without rigid end fittings, soft actuators without rigid end fittings and with a mesh having a low initial braid angle, etc.) is advantageously arranged (e.g., in one or more discrete arrays acting along one or more lines of action) to enable the soft actuators 20 to act in a biomimetic manner to achieve a wide variety of motions, which can be achieved and predicted ahead of time—both in 2D and 3D. The arrangement of the soft actuators 20 within the substrate may advantageously be assisted by using finite element modeling to orient the actuators spatially in the substrate (e.g., a 3D matrix). Thus, the shape of the actuator matrix or matrices, and the orientation of the actuators, matrix, or matrices, can be customized to suit a particular application (e.g., a cardiac simulator, a DCC device, etc.).

The substrate in which the soft actuators 20 are incorporated, and/or the soft actuators themselves, can comprise one or more sensing elements. By way of example, the soft actuators 20 and/or substrate(s) may comprise (or be operatively associated with) sensors such as, but not limited to elastic strain sensors (e.g., as disclosed in WO 2013/044226 A2, which is hereby incorporated by reference in its entirety, etc.), elastic sensors configured to measure bending curvature (e.g., as disclosed in WO 2012/103073 A2, which is hereby incorporated by reference in its entirety, etc.), and/or pressure sensors (e.g., as disclosed in WO 2012/0509380 A2 or U.S. Pat. No. 8,316,719 B2, each of which is hereby incorporated by reference in its entirety, etc.), or implantable three-axis accelerometer.

Whether incorporated into a cardiac simulator or a direct compression device, in accord with the present disclosure, such sensors may be advantageously integrated with the actuator 20 (e.g., PAMs) control system (e.g., to form a closed-loop system) and/or a communication port and/or a communication device to facilitate transmission of data and/or instructions to or from the sensor(s) to the control system and/or an external system. By way of example, such sensor(s) could be used to detect the electrical wave propagation of the heart in order to actuate the actuators accordingly. As another example, sensors disposed at the device/heart interface would enable complete conformance to the heart, and enable dynamic actuation (number of active actuators and degree of actuation) of the heart as it remodels. Using sensors, such as described above (soft sensors to measure force/pressure/electrical signal embedded in a silicone electrode patch in the substrate and/or under the mesh of the PAMs, etc.), the DCC device 100 can be tailored (e.g., programmed) to provide actuation that is patient-specific.

Existing cardiac simulators for device evaluation are typically computer-based, biological or mechanical, and have the respective inherent limitations of not allowing physical testing, difficulty in obtaining and preparing specimens, or not mimicking bulk inhomogeneous tissue material properties.

Figure 10:
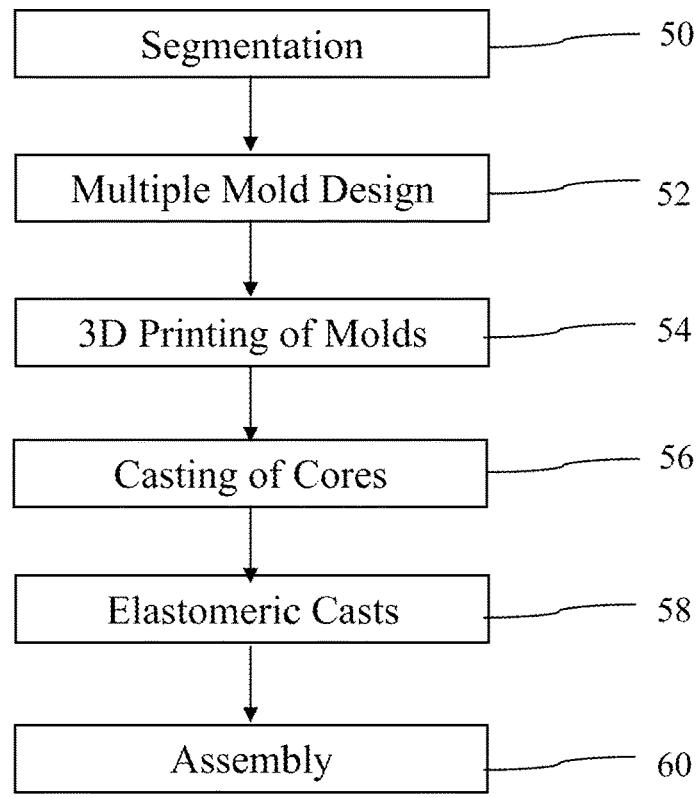
FIG. 10 shows general process steps for the design and fabrication of a soft cardiac simulator in accord with at least some aspects of the present concepts.

FIG. 10 shows an example of the design, development and fabrication of an anatomically accurate, inhomogeneous, elastomeric cardiac model for in vitro testing of cardiac devices in accord with at least some aspects of the present concepts. Segmentation of clinical data was performed with Mimics software (Materialise). Mold creation and optimization was performed in 3-Matics (Materialise) using the tooling module. A total of twenty-one molds for chambers/vessels and structural components of the heart were designed in 3-matics (Materialise), including sixteen two-part molds (cardiac chamber internal volumes and endocardial walls, main vessel internal volumes and outer walls), four one-part molds for the valve annuli and one two-part mold for final myocardium cast. Molds were optimized for alignment and degassing in 3-matics and then 3-D printed (Connex 500, Objet). Internal volumes were cast with paraffin wax. Endocardial and vessel walls and annuli were then cast in elastomeric materials that resembled material properties of corresponding native tissue. Internal volumes were subsequently melted out and elastomeric chambers and internal structures were sutured together, separated by functioning valves created using an involuted tube surgical technique. Other means of connecting the elastomeric chambers could also be utilized such as, but not limited to, medical grade adhesives (e.g., Bioglue, UV light activated adhesives, etc.) or ultrasonic welding.

The connected elastomeric chambers and vessels were aligned in an outer mold and a final elastomeric layer was cast to represent the myocardium. This synthetic model was subsequently attached to a commercially available pump, and the pump was modified using a microcontroller to allow user-control of heart rate, systolic and diastolic volumes and incorporation of sensing capabilities (pressure and flowrate on inflow and outflow). Parameters were controlled and sensing data was acquired and plotted via a Matlab general user interface. The final simulator is a patient specific, easily modifiable, inhomogeneous bench-top model that can be used to provide rapid meaningful data on design iterations of cardiac devices before pre-clinical testing.

As shown in FIG. 10, in act 50, segmentation of CT data for each chamber is performed using FE material assignment module in Mimics. Mimics was used to segment the following chambers: internal geometries and endocardial walls of the left atrium, right atrium, right ventricle, left ventricle, trunk and outer vessel walls of the pulmonary artery, aorta, vena cava and pulmonary vein, an outer mold for the overall myocardium and annuli of the mitral, tricuspid, aortic and pulmonary valves. The finite element module was used to aid with segmentation of the different anatomical structures (endocardial layers, vessels, valve annuli and myocardium).

In act 52 of FIG. 10, molds were created for each subcomponent using the 3-Matic tooling module. A total of 21 masks were exported as stl files to 3-matics (Materialise). A box was fitted around the internal volume, and a boolean subtraction of the internal volume was performed. Molds were split along the most convenient split-line for demolding using the tooling module. Cylinders were created using the design tools within 3-matics to help with alignment of the internal positives in the outer molds, and subtracted from the mold. Funnel-shaped reservoirs were added to the molds to help with subsequent degassing. Alignment pins were also created in the 2-part molds to ensure both halves were aligned correctly. Finally features were added along the split-lines to aid with demolding.

In act 54 of FIG. 10, 3D printing of molds (inner positive and outer wall) for subcomponents was performed. Twenty one molds (17 2-part molds and 4 1-part molds) were then printed on a Connex 500 printer (Objet) using vero blue material (printed with internal side facing up in glossy surface finish mode). Molds were then cleaned with a water blaster to remove any support material and placed in an oven at 60° C. for four hours.

FIG. 10 shows, in act 56, casting of internal volume positives with paraffin wax, wherein the internal volumes were cast using paraffin wax (generalwox.com). These internal positives were demolded and aligned in outer molds. In act 58, casting of endocardial walls and annuli was performed following matching of synthetic material properties to literature values for the valve annuli, endocardial, and myocardial tissue. Dragon Skin, Ecoflex 0050 and Ecoflex 00-30 (Smooth-on Inc.), respectively, were used for these components. Once poured, the elastomer-filled molds were degassed in a vacuum chamber at −100 KPa for five minutes, and placed in a pressure oven at 100 psi at 100° F. to cure. Paraffin wax was then melted out of chamber and vessel casts by heating to 140° F. Endocardial layers and vessels were sutured to valve annuli in the correct orientation. Functioning tri-leaflet valves were then created from tubes of Ecoflex 00-30 for each of the four valves using a published surgical technique where the tube is cut in three areas and involuted. These were sutured into the corresponding molded valve annuli before final assembly of the internal structures.

In act 60, the components are aligned in a final outer mold and the myocardium was cast with Ecoflex 00-30. Degassing, and curing was carried out, as previously described, and the final heart was de-molded.

Following assembly and production of the final heart, the final elastomeric casting is then able to be advantageously connected to a pump for actuation and sensors utilized to measure, inter alia, flow and pressure. For testing purposes, a commercially available pump was acquired (Harvard Apparatus piston pump model 1423—Harvard Apparatus, Holliston, Mass., USA). A rig was designed to attach the heart so that the free wall was unsupported to get realistic motion for device testing. Pulmonary artery and aorta were connected to the outflow and vena cava and pulmonary vein were connected to the inflow of the pump using off-the-shelf tubing (secured with zip-ties) and connectors (McMaster Carr). Plexiglass was laser cut to provide a four wall enclosure for the heart with adjustable plates for attaching tube connectors. To compensate errors in the connector slot position and make the overall process of connecting the heart model to the holding frame easier, the acrylic plates incorporating the connector slots were separated from the four plates building the main frame and could be moved linearly on the main plates. The plates holding the connector slots and the main plates were affixed to each other. The pump was modified for the intended cardiac simulator and electrical circuits wired to accommodate the new controls. A control box was integrated into the pump housing, the control box being connected to sensors, the pump and the computer. The microcontroller and the motor driver contained in the control box control the pump speed, using the encoder switch signals for a closed loop control. This motion control manages not only the simulated heart rate, but also the heart models systole to diastole speed ratio. Additionally, the microcontroller manages the computation of incoming and outgoing signals (e.g. sensor signals). The connection between the control box and the computer is used to transmit the sampled sensor data and the heart model's current state (systole or diastole) from the microcontroller to the computer.

An Arduino Mega development board was used. The board features an AT Mega 256 microcontroller, a preinstalled boot loader, a USB and a power jack and offers pin-and-socket connectors to the microcontroller's general purpose in-put/output pins. The microcontroller runs with a frequency of 16 MHz and provides 16 analog to digital converter pins. The Harvard pump was originally controlled in an open loop, regulated by two potentiometers connected to the motor's driver. To use the Arduino board for a closed loop control, the potentiometers are detached from the motor driver and a connection to the Arduino is established. Aside from the user interface provided by the computer, the control box also offers a standalone user interface, which may be used in test scenarios that do not need constant sensor surveillance. This standalone user interface is comprised of navigational buttons, a keypad and an LCD screen, but could comprise any user interface.

As the motor driver expects analog control signals, the digital to analog converter (DAC) MPC4921 (Microchip Technology Incorporated, Chandler, Ariz.) is used to convert a 10 bit digital SPI based signal to an analog voltage signal. A process control module 4 (PCM4) (Minarik Corporation, Glendale, Calif.) is used to convert the DAC's signal to the floating voltage difference output expected by the motor driver. As the Harvard Pump is already calibrated to simulate human physiological cardiac conditions, the calibration potentiometers of the pump's motor driver were not changed. Hence, the pump's maximum heart rate is equal to its original maximum speed of 100 beats per minute.

Two pressure sensors (HSCMAND030PGAA5, Honeywell S&C) and two flowmeters (SeedStudio POW 110D3B G, Electronic Inventory Online) were connected in-line using off the shelf fittings (McMaster-Carr). A graphical user interface supplied by the computer was implemented in Matlab using the GUIDE tool for user interface creation. The platform was chosen, as it offers powerful and easily implemented data storage, plotting and data manipulation capabilities. In the user interface, the user has an advanced and a basic control window where the user can change the sensors and peripheries and control data output or simply vary beats per minute and time in diastole. A separate data acquisition window allows the user to measure flow and pressure at the inlet and outlet, and calculate ejection fraction.

The testing revealed that the cardiac simulator is anatomically accurate and reflects the inhomogeneous nature of cardiac tissue properties. The synthetic model can easily be switched for patient-specific and pathological anatomies and system, as a whole, can be used for testing of cardiac devices such as, but not limited to, trans-apical valve delivery devices, intracardiac delivery devices, ventricular assist devices and extra-cardiac compression devices. The synthetic model demonstrated inhomogeneous properties simulating the material properties of different structures and layers of the cardiac tissue, which can be easily individualized and modified for patient-specific and pathological cardiac anatomies. This is hugely beneficial for rapid design iterations for cardiac devices before moving to pre-clinical testing. It is noted that prior art synthetic cardiac models that exist as clinical training tools to simulate heart sounds, artery palpations and the like do not simulate cardiac wall motion, a property that is key for testing of cardiac devices used during beating heart surgery. While beating heart simulators do exist for training on off-pump procedures, they are not readily modified for patient-specific anatomies. Likewise, while mechanical simulators also exist that simulate the motion of the ventricles, they do not mimic the bulk tissue properties and internal surface friction of the heart.

In accord with the soft actuators 20 disclosed herein, the soft actuators can be oriented to achieve both physiological and pathological motion that matches reported clinical values well, such as to simulate both compression and rotational movements of the heart. In contrast, the Chamberlain heart simulator comprises actuators that cannot be individually actuated, thereby making simulation of the pathological condition difficult. Like other cardiac simulators, the Chamberlain heart is intended as a surgical training tool, not as a medical device evaluation platform. The cardiac simulator described herein would, instead, provide a much more realistic teaching tool and training environment for trainee surgeons, provide a portable demonstration environment (e.g., for medical device manufacturers, for conferences, for exhibitions and trade shows, etc.) and/or testing of new medical devices.

The cardiac simulator can provide, for example, valuable data on the effect of 3D motion on implantable devices such as ventricular/atrial septal defect repair devices and stented/stentless heart valves. The fatigue fracture of these devices, and their potential to perforate or erode tissue is a problem and potential risk that until now has not had an accurate in vitro test-bed. The cardiac simulator is echo and MRI compatible and can be fitted with endoscopic cameras allowing visualization of these devices and how they move in an accurate mechanical environment, which does not currently exist.

As one advantage of the presently disclosed DCC devices 100, arrangement of the soft actuators 20 along lines of action of the muscle fibers of the heart allows this DCC to generate outputs that follow the natural movement of the heart. Further, in at least some aspects, unlike competing technologies, the curvature of the heart is not inverted, which is believed to attenuate adverse remodeling of the heart and to help reduce friction and injury to the myocardium (contusion, conduction block etc.). Passive restraint devices have limitations of affecting diastolic filling. Ventricular assist devices (VADs) are blood contacting, and therefore require the patient to be on anti-coagulation therapy (e.g., direct prothrombin inhibitors, warfarin, dabigatran, rivaroxaban, apixaban, etc.) following implantation, which introduces attendant systemic risks (hemorrhage). In contrast, the presently disclosed DCC devices 100 are non-blood contacting. Additionally, DCC devices 100 are easier to apply than VADs and offer bi-ventricular support. Studies show that the heart can undergo reverse remodeling from prolonged ventricular unloading with conventional LVADs. However, conventional methods of ventricular support provide mechanical unloading they do not assist with actual muscle shortening as epi-cardial compression does. This may offer an advantage for ventricular recovery. VADs can be pulseless, leading to problems including valve leaflet fusion as the function of the heart is completely taken over by the device. The presently disclosed DCC devices 100 would be actuated with the heart to promote native healing as well as assisting with heart functioning.

As noted above, the presently disclosed DCC devices 100 are capable of transmitting twisting and untwisting mechanics (rotation) to the heart, which has shown to be effective in increasing cardiac output. Conventional devices that transmit twist are very invasive, requiring removal of the apex of the ventricles with a weak mechanism of actuation or they use the sternum as an attachment. Further, such conventional devices push in on the heart, disadvantageously inverting the curvature of the heart.

The presently disclosed DCC devices 100 are adaptable so as to be patient-specific. Using the processes developed to make the simulator, described herein, patient-specific "cardiac sleeves" that conform to the epi-cardial surface of that patient, whether a human patient or an animal patient, can be fabricated with actuators (e.g., PAMs as disclosed) could be selectively actuated at the injured tissue. These actuators and/or a substrate bearing such actuators may comprise one or more sensors to monitor one or more variables (e.g., pressure, tensile force, etc.) relevant to biological functions (e.g., a local state of the heart), operation of the device as a whole, or operation of a component of the device (e.g., a single actuator).

Yet further, unlike most existing direct cardiac compression devices, the presently disclosed DCC device can assist with diastolic heart failure as well as systolic heart failure, due to the fact that soft actuators 20 (e.g., elastomeric PAMs) can lengthen with a vacuum and contract when pressurized. In this sense, the DCC device can help the heart to fill as well as to pump. Diastolic restriction has been an obstacle for previous direct compression devices. Further, soft actuators 20 can be provided to lengthen under pressure and contract with a vacuum. Moreover, a first set of actuators may be provided and arranged to perform a first function (e.g., filling) and a second set of actuators may be provided and arranged to perform a second function (e.g., ejection).

As noted above, the soft actuators 20 (e.g., PAMs) can be individually actuated, so the DCC device can be used as a biventricular device, as a left/right ventricular assist devices or as a right/left atrial assist device.

Figure 11A:
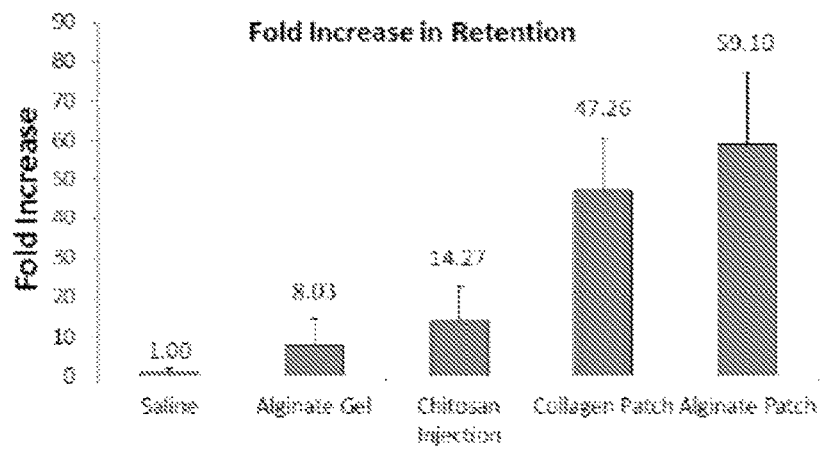
FIG. 11(a) shows the fold increase in cell retention when using biomaterials to deliver cells to a myocardial infarct rat model after 24 hours (compared to a saline control).
Figure 11B:
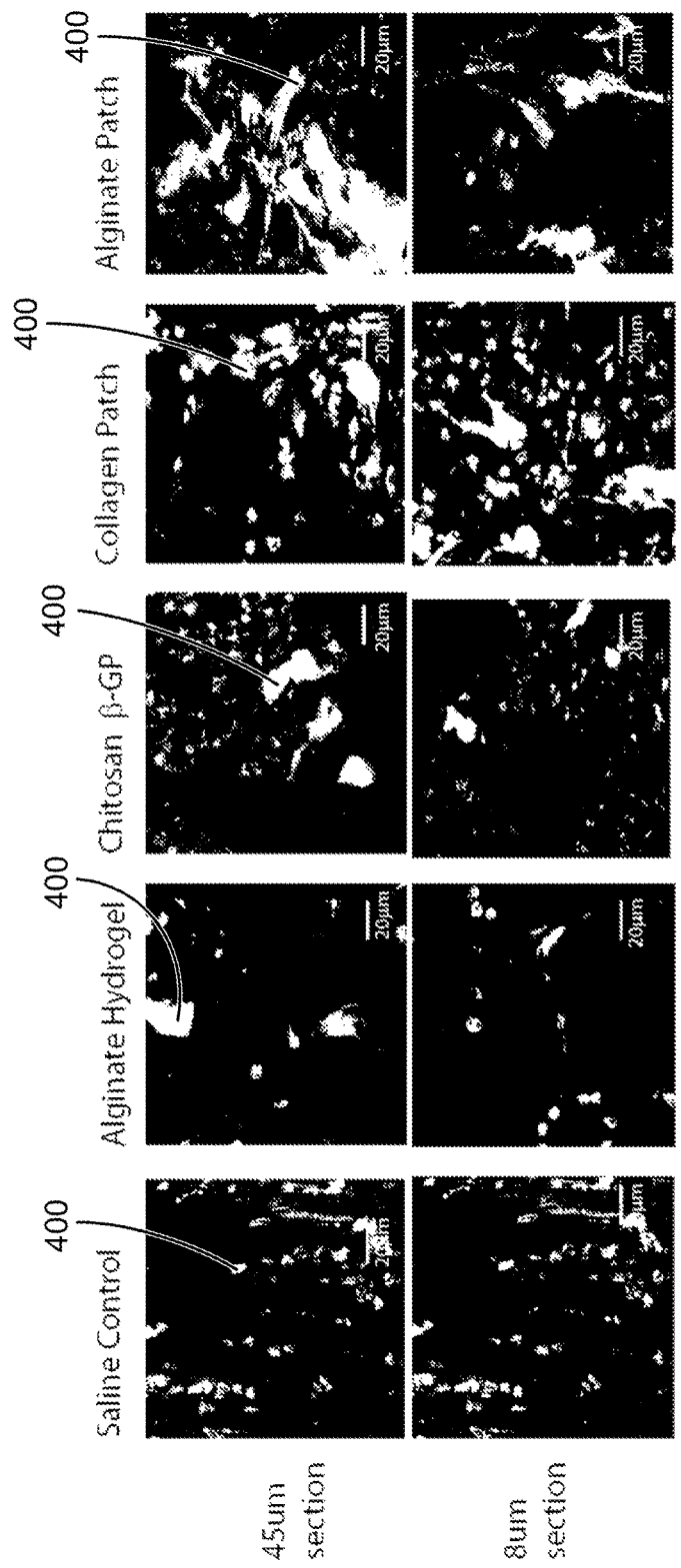
FIG. 11(b) shows biomaterial delivery (e.g., cell delivery) to an infarcted heart with cell retention after 24 hours showing DAPI and implanted cells with GFP antibody for each group, utilizable in accord with at least some aspects of the present concepts.

It yet other implementations of the present concepts, the DCC device disclosed herein can be used for delivery of bioagents, biomaterials, or therapeutic agents (e.g., injectable hydrogel, cells, etc.). Cell delivery to the infarcted heart appears to be a promising therapy, but is currently limited by very low acute retention and engraftment of cells. It was hypothesized that acute retention could be improved with a biomaterial carrier, and a study was performed to compare several biomaterial carriers. In this study, represented in FIGS. 11(a)-11(b), cells were quantified 24 hours post-implantation in a rat myocardial infarct model in five groups (n=8 per group); saline injection (current clinical standard), two injectable gels (alginate, chitosan) and two epicardial patches (alginate, collagen) in order to assess whether biomaterial carriers increased cell retention. For injectable groups 60 ul of saline or gel containing 400,000 human mesenchymal stem cells 400 was injected intramyocardially in the infarct border zone. 400,000 cells were seeded on alginate or collagen patches, and implanted on the epicardial surface at infarct border zone. At 24 hours, retained cells 400 were quantified with an in vivo imaging system. Hearts were perfused and sectioned to stain for retained cells 400. All biomaterials significantly improved retention compared to a saline control, with 8-fold and 14-fold increases for alginate and chitosan injectables, and 47-fold and 59-fold increases achieved with collagen and alginate patches, respectively. Immunohistochemical analysis, shown in FIG. 11(b), qualitatively confirmed these findings. Encapsulated/seeded cell 400 survival was assessed in hypoxia/ischemia to further compare biomaterials. Thus, injectable gels and epicardial patches were demonstrated to improve acute retention of cells when compared to a saline control. Injectable gels enable immediate myocardial delivery while epicardial patches facilitate superior retention and could potentially sustain cell delivery over extended periods.

The devices disclosed herein (e.g., PAMs, DCC device(s), cardiac simulator(s), etc.) can be advantageously manufactured using one or more biocompatible, resorbable (e.g., Phasix™ Mesh, TIGR® Matrix, Vicryl™ Mesh, etc.) or biodegradable materials (e.g., poly(lactide-co-glyoclide), polyurethanes, etc). Further, the DCC device(s) and/or constituent parts (e.g., PAMs) may comprise a coating (e.g., polymeric, non-polymeric, biodegradable, etc.) that can be optionally drug-eluting (e.g., drugs such as immunosuppressants, anti-inflammatory drugs, beta-blockers, aldosterone antagonists, inotropes, etc.) to facilitate localized delivery of a therapeutic agent.

Further, the devices disclosed herein, particularly the DCC device(s), can advantageously be configured to facilitate retention or and/or distribution of (e.g., sustained delivery) bioagents, biomaterials (e.g., cell therapy), or therapeutic agents. By way of example, the substrate into which the soft actuators 20 (e.g., PAMs) are disposed can comprise one or more ports into which one or more bioagent(s), biomaterial(s), or therapeutic agent(s)(e.g., a drug) can be introduced (e.g., via syringe, catheter, etc.) and retained for sustained or controlled delivery (e.g., via channels, tracks, etc.). As one example, an imaging or contrast agent could be injected into the port of the DCC device for distribution throughout channels formed in the substrate (e.g., in a matrix) to facilitate imaging of the movement of the DCC device (and underlying heart under fluoroscopy or x-ray). In another example, the substrate into which the actuators (e.g., PAMs) are disposed can comprise one or more channels or scaffolds filled with a bioagent(s), biomaterial(s), or therapeutic agent(s)(e.g., a drug) retained for sustained or controlled delivery (e.g., via channels, tracks, etc.). The channels or scaffolds may be optionally refillable. In at least some aspects, the channels or tracks noted above may comprise openings formed at locations adjacent an interface between the device and the heart (or other tissue to which the device is attached) and the channel or tracks can output from the openings a gel or other substance to help reduce friction between the device and the heart (or other tissue) and/or to help reduce inflammation.

Mechanical assistance can potentially be combined with the delivery of therapeutics. For example, a parallel lumen or dual lumen track or separate line can be used to deliver both a therapeutic agent (e.g., in an inner lumen) and pressurized air for actuation of the soft actuators 20 (e.g., in an outer lumen).

In accord with at least some aspects of the present concepts, not only is a soft direct cardiac compressive (DCC) device used to partially encapsulate a heart (e.g., a failing heart), but such DCC is used to facilitate cell delivery from a liner at the device/epicardial interface that allows multiple minimally invasive replenishments with cells or bioagents. DCC's in accord with any aspect of the present concepts can serve as carriers for cells or bioagents (e.g., cells can be delivered via an integrated biomaterial liner in the DCC device 100 that allows percutaneous replenishment through conduits formed therein or attached thereto). This combined mechano-biological approach offers the potential to provide both acute assistance by augmenting cardiac output and longer term benefit by unloading of tissue to reverse remodeling, in addition to improving retention of biological therapeutics to promote endogenous repair.

The motive force for the actuators of the DCC device 100 may comprise an external pressure source (e.g., a pulsed pressure source) and fluid supply (e.g., a bed-side unit or wearable unit comprising a portable pump, a compressed air source and regulator/valve system, etc.). Alternatively, the motive force for the actuators of the DCC device 100 may comprise a closed-system bladder or bladders and actuation system(s) (e.g., pump, etc.) configured to selectively compress the bladder(s) or to draw fluid from the bladder to force the fluid (e.g., air, helium, saline, etc.) to the soft actuators 20 (e.g., PAMs). Again, although the examples herein have generally been described in relation to pneumatic systems (e.g., pneumatic artificial muscles), all of the embodiments and concepts disclosed herein are equally amenable to utilization of hydraulic fluids (e.g., saline, water, contrast, etc.) as an actuating fluid and may comprise soft actuators utilizing hydraulic fluids, or other types of soft actuators.

In alternative configurations of the DCC device 100, the actuators may comprise, in whole or in part (e.g., in combination with soft actuators 20 as disclosed herein), actuatable shape memory alloys, electroactive polymers or ionic metallic polymer composites.

It is believed that the DCC devices 100 disclosed herein, where adapted to provide actuation along the natural lines of force of the heart musculature (biomimetically), an infarcted region of the heart (that is under high stress, according to Eq. (4)) can be "unloaded" and, in so doing, can promote healing, attenuate adverse remodeling, ventricular dilation, infarct aneurysm and rupture. Further, it is believed that, by mechanically unloading such affected region of the heart, or replicating natural motion of the heart, cell therapy to independent ventricular can be potentially promoted. Actuation of the materials containing cells may encourage them to secrete therapeutic factors, or differentiate.

In the methods of forming a soft actuator, a DCC device 100, or a cardiac simulator, other conventional processing techniques (e.g., 3-D printing) can be employed to form one or more components thereof, without limitation.

Further, other potential applications for the soft actuators or direct cardiac compression device (which could be used in other, non-cardiac applications) can include, by way of example, maxillofacial applications. After a patient receives a full or partial face transplant, the patient can wear a soft actuated protect mask, with embedded artificial muscles such as those disclosed herein, that match the orientation of the muscles in the face so that the mask can stimulate normal types of facial expressions (e.g. facial expressions) and therapy delivery can be optionally combined with the soft actuated protect mask. In general, the concepts disclosed herein can be used to stimulate and facilitate nerve regeneration or re-innervation. In another potential application, soft actuators or a DCC device or system as disclosed herein can be implanted on a patients bladder as an assistive device or but also for rehabilitation and/or therapy for a patient with bladder issues. In yet other aspects, soft actuators or a DCC device or system as disclosed herein may be used to massage various internal and external organs and tissues where certain types (maybe multiple types) of motions can be programmed for stimulating blood flood or removing unwanted fluid build-up.

In general, the soft actuators or a DCC device 100 or system as disclosed herein can be used to aid any type of physical therapy or rehabilitation inside of or outside of the body. The soft actuators can be arranged in a matrix that is in a 2-D or 3-D in shape, and can be adapted to provide any type of motion including twisting, bending, extension, contraction, expansion, or combinations thereof. Stiffness of the matrix can be tailored to a desired application and a stiffness of the material(s) used in the matrix may be selected so that it can be pre-stretched or pre-tensioned to passively provide forces (e.g., tensile forces) in addition to actively applying force upon actuation.

The soft actuators described herein may alternatively be integrated into devices, such as surgical devices (e.g., retractors, graspers, etc.).

The present concepts further expressly include compliance matching between the soft actuators or DCC device 100 or system disclosed herein and herewith (all materials attached hereto and submitted herewith are an integral part of the present disclosure) and any tissue or material to which such soft actuators or DCC device or system are applied. Thus, the soft actuators or DCC device or system can be adapted, based on application, such that that contacting materials share similar mechanical rigidity in order to evenly distribute internal load and minimize interfacial stress concentrations (e.g., the soft actuators or DCC device 100 or system can be matched to optimize a compliance with an internal organs and/or tissue to which the soft actuators or DCC device or system is applied).

In yet other aspects, the soft actuators or DCC device 100 or system may be utilized in a diaphragm replacement, or replacement (or mechanical assistance) to any soft musculature.

In still other aspects, the soft actuators or DCC device 100 or system may be utilized in vivo in a cuff disposed around a vessel (e.g., abdominal aorta) to prevent aneurysm dilation.

In still other aspects, the soft actuators or DCC device 100 or system may be utilized in a sleeve that goes around leg and, in combination with a control system and optionally feedback from one or more sensors, is configured to pulse to increase venous return in patients with heart failure.

Further applications for the soft actuators or DCC device 100 or system may comprise rehabilitation after surgery (e.g., to assist movement of arms/legs/wrist/fingers, etc.), aiding peristalsis in the esophagus, or compression outside chest after trauma.

FIGS. 12(*a*)-12(*e*) show, in accord with at least some aspects of the present concepts, fabrication of a left ventricle prototype in accord with at least some aspects of the present concepts. Following modeling of a left ventricle of the heart, a prototype was fabricated with a multi-step molding process that included optional features (EM tracker alignment features) to aid, for testing purposes, measurements of movement in three dimensions. This class of programmable, soft actuated material with multiple degrees of freedom has potential for a huge range of applications including simulating normal physiological and pathological motion, in addition to replacing or restoring the function of failing organs.

FIG. 12(*a*) shows an exploded isometric of Core 1 and Core 2 relative to a base or mold used to form a composite member of Core 1 and Core 2. Alignment tabs or mating (e.g., male/female) attachment members are advantageously provided to ensure accurate alignment of the components relative to one another. FIG. 12(*b*) shows the assembled Core 1, comprising elastomeric actuator alignment features, being inserted into the mold, followed by a first casting of Ecoflex 00-30 to create an outer shell with alignment tabs for soft actuators 20 in FIG. 12(*c*). Soft actuators 20 (e.g., PAMS) were inserted and aligned with the alignment features and a small amount of prepolymer was used with optional local heating (e.g., a heat gun) to secure the actuators in place. As shown in FIG. 12(*e*), with the outer Ecoflex shell remaining in the mold and Core 2 positioned in Core 1, a second casting (e.g., a second pour of Ecoflex 00-30 or a different elastomer than that used for the outer shell) fully embeds the actuators. In the prototype, the inner diameter of the mold was 84 mm.

Figure 13A:
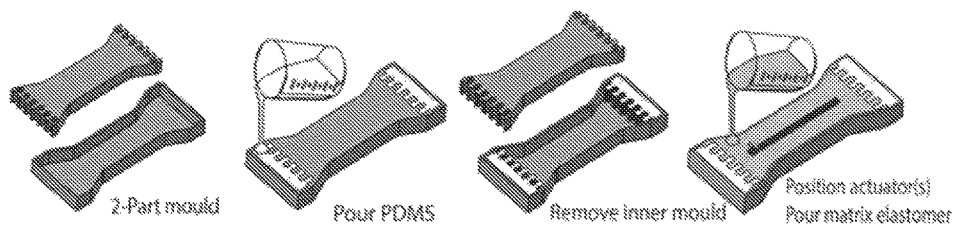
FIGS. 13(a)-13(c) show, in accord with at least some aspects of the present concepts, a fabrication process for test specimens, test specimens showing optical marker placement for horizontal and vertical strain calculations and dimensions, experimental and FE strain for various matrix widths; experimental and FE force prediction for various matrix widths for various actuator spacing (S) in terms of resting diameter of actuator (D=5 mm).
Figure 13B:
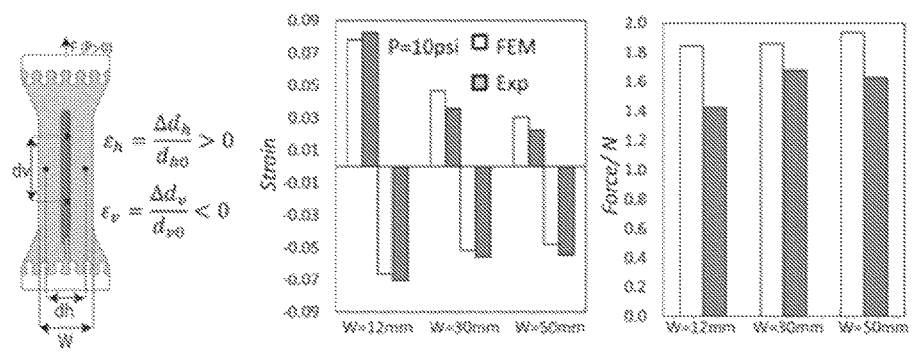
Figure 13C:
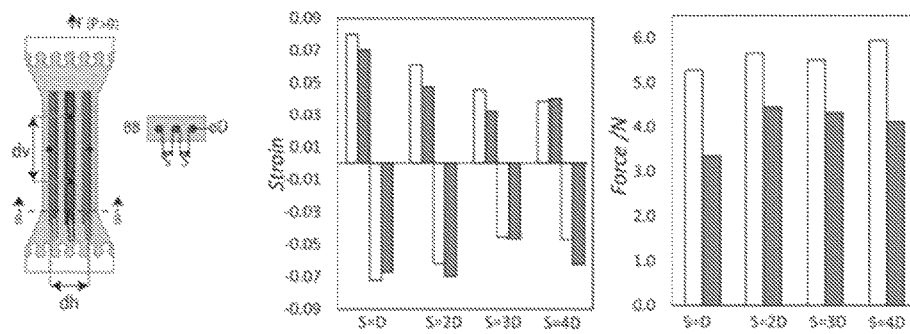

In order to understand the behavior of a composite material consisting of soft actuators 20 embedded in an elastomeric matrix, a number of two dimensional test specimens were manufactured with varying material properties and actuator number and spacing. FIG. 13(*a*) shows the process for fabrication of "dog-bone" shaped test specimens with embedded actuators (one or three) with two different elastomeric matrices (Ecoflex 00-30, Smooth-on Inc. and Elastosil M4601, Wacker Chemie AG). Two-part molds were 3D printed that included interdigitating features to provide increased tensile strength at the material interface between the specimen and its ends that were clamped in the tensile testing machine. Before casting the specimens, the actuator and supply lines were placed in the mold and PDMS and Ecoflex elastomer were poured into the ends and main cavity respectively and the two materials bonded at the interdigitating interface. The soft actuators 20 were fixed in place until a final pour of Ecoflex 00-30 or Elastosil M4601 to top off the mold and the air supply tube separated from the mold during curing to ensure the air supply tube would not be inadvertently embedded in the test specimen.

Optical markers were added to test specimens with a template (e.g., markers were placed in a plurality of rows vertically spaced apart from one another) and a Matlab (Mathworks Inc.) interface was used to track them and strain measurements were made according to the equations in FIG. 13(*b*). Testing for force and strain at various input pressures was carried out, the results of which are represented in FIGS. 13(*b*)-13(*c*). Ecoflex 00-30 (Smooth-on Inc.) was selected as the matrix for fabrication of the soft actuated material due to the ability to generate larger strains, and because its reported modulus 125 kPa was within the range of reported values for myocardial tissue (203.3±55.6 kPa for healthy myocardium and 117.3±37.0 kPa for infarcted myocardium).

Having ascertained the properties of the individual actuator 20 and composite actuator-matrix specimens, a methodology was developed for creating numerical simulations for the soft actuated materials. The simulations were performed using the nonlinear finite element code ABAQUS/Explicit and provided a means to predict the performance of different design iterations of the soft active materials. To model the response of the actuators to an increase in pressure, without the need for a detailed model of the braided mesh, temperature and orthotropic coefficients of thermal expansion were used to model their anisotropic strain response. Soft actuators 20 were assigned an experimentally derived modulus of 1.78 MPa, as shown below.

$$E = \frac{\sigma}{\varepsilon} = \frac{F/A_0}{\Delta d/d_0} = \frac{F}{d} * \frac{d_0}{A_0} = 0.70 * \frac{50}{\pi(2.5)^2} = 1.78 \frac{N}{mm^2} = 1.78 \text{ MPa}$$

Actuators 20 were also assigned orthotropic thermal expansion coefficients according to experimentally derived strains that were negative in the longitudinal direction and positive in the radial direction for a positive change in pressure. The host elastomeric matrix was modeled as an elastic material as strains were in the linear elastic range. It was assigned a thermal expansion coefficient of zero. Matrix and actuators 20 were merged (see FIGS. 13(*b*), 13(*e*)) before applying a uniform temperature (corresponding to actuation pressure) to the entire assembly. The output for each specimen was the reaction force at fixed ends and displacement for selected nodes corresponding to the optically tracked markers on the physical specimens.

In FIGS. 13(*b*)-13(*c*), numerical and experimental strain and force results were compared for single and multiple actuators, respectively. Very good agreement for strain was observed, with discrepancies likely due to quality and consistency of optical markers. As expected, a trend towards decreasing strain as matrix width or actuator spacing was observed to increase. Force produced by the specimens is less affected by matrix width and actuator spacing (FIGS. 13(*b*) and 13(*c*), right graph). Discrepancies between the experimental and numerically predicted force were observed (FIG. 13(*c*), right graph) with the experimental force being less than the numerical prediction. This may be attributed to some slippage of the test specimens from the grips of the tensile testing machine, or some slight delamination at the actuator/matrix or matrix/PDMS interface, although measures were taken to minimize these experimental artifacts. A limitation of the numerical modeling approach is that it is not as accurate for higher pressures and higher modulus matrices.

As the above prototype was particularly adapted with EM tracker alignment features to facilitate data acquisition, a customized stand having an opening of 82 mm in diameter was provided to support the left ventricle at the base, so that the apex was free to rotate. Metal fixtures were avoided to avoid interference with the electromagnetic sensors (Trak-STAR 3D Guidance system (Ascension Technologies)

Model 90 6-DOF freedom sensors (0.9 mm)). One sensor was fixed in the center of the base to act as the origin and the position of the sensors relative to the origin were measured. The transmitter and the origin were fixed. A needle was used to make a small hole in the center of the alignment features and sensors were embedded in the wall. Four sensors were placed symmetrically in the outer left ventricle wall at each of the basal and apical planes. Two sensors were placed in the mid-plane, and an additional sensor at the apex. Information from the initial sensor readings was used to select the appropriate nodes in the finite element simulation in order to have a direct comparison. Actuation pressure was controlled with a pressure regulator (Campbell Hausfeld) and a sensor (Balluff BSP000W) in line with the air supply.

Cubes software (Ascension Technology) reported the three dimensional positions of each sensors (x,y,z coordinates relative to the fixed origin) at each pressure increment, and a matrix of sensor coordinates was output to a matlab file. Sensor co-ordinates were recorded five times at each measured pressure. Apical rotation was calculated from these positional coordinates and the rotation of each node was averaged for each pressure, and all four nodes in the plane were averaged for apical rotation. In order to measure apical and basal rotation, the left ventricle was supported with a flexible band at the mid plane, and the readings of sensors in the apical and basal planes were used to calculate apical and basal rotation. Reported values (see FIG. 14(c)) are averages of the four nodes in each plane.

McKibben-based elastomer actuators 20, such as is disclosed above comprising an inflatable bladder surrounded by a braided mesh, were selected to act as the preferred contractile elements for the present concepts, but the present concepts are not limited thereto. Desirably, the disclosed soft actuators 20 (i) can be fabricated to be fully soft, (ii) can be actuated to achieve significant contraction with low pressures (demonstrating a load-length behavior similar to muscle), (ii) can be actuated quickly (0.05 seconds dynamic response time) and (iv) can be easily integrated into the manufacture of three dimensional soft actuated materials through a multi-step co-molding process. Such soft actuators 20 are limited, however, in that they can only have one mode of actuation; axial contraction with an accompanied radial expansion in response to a change in pressure. However, if arranged spatially in a matrix according to a desired function, in accord with the present concepts, they may be analogous to individual contractile elements such as muscle fibrils and more complex three dimensional resultant motions can be achieved. For preliminary testing, soft low-threshold pressure actuators were fabricated as described above in relation to FIGS. 4(a)-4(b), but were scaled down in size to a nominal length and diameter of 75 mm and 5 mm respectively.

Once the contractile elements for the soft actuated material was optimized and characterized, arrays of actuators in 2D test specimens were created. By varying matrix material, width, number of actuators and actuator spacing, the inventors characterized effects on horizontal and vertical strain distribution, and total force generation for each test specimen. The inventors also subsequently introduced a finite element (FE) simulation of the actuator-matrix structure, and validated this simulation by comparing the results to experimental data, as is shown in FIGS. 14(b)-14(c) and 15(a)-15(e). The inventors looked to the left ventricle of the heart, as a specific three-dimensional (3D) case study, to demonstrate the modeling approach and manufacturing capabilities of this new platform of materials. By varying the spatial arrangement of these linear actuators and embedding them in a soft matrix, they achieved 3D motion that can be tailored to achieve physiological and pathological motion.

Upon establishing the fabrication method, completing the experimental characterization, and developing and validating a numerical simulation approach, the inventors then took inspiration from nature to create a three dimensional soft active material. The left ventricle of the heart is a muscular structure capable of achieving complex motion through oriented active contractile elements. During the contraction phase of the cardiac cycle the apex of the left ventricle twists anti-clockwise approximately 6-10° when viewed from the apex while the base of the heart has a net clockwise rotation of 2-4°. The resultant left ventricular (LV) twisting motion is complex, with the apex and base rotating in opposite directions. Twist is governed by parameters including orientation of the heart muscle (myocardial) fibres and the balance between the contraction of the outer (sub-epicardial) and inner (sub-endocardial) fibres which are arranged in opposing helices (FIG. 14(a)). Also represented in FIG. 14(a), for general reference, are the apical region or plane 191, mid-region or mid-plane 192 and basal region or plane 193.

Figure 14B:
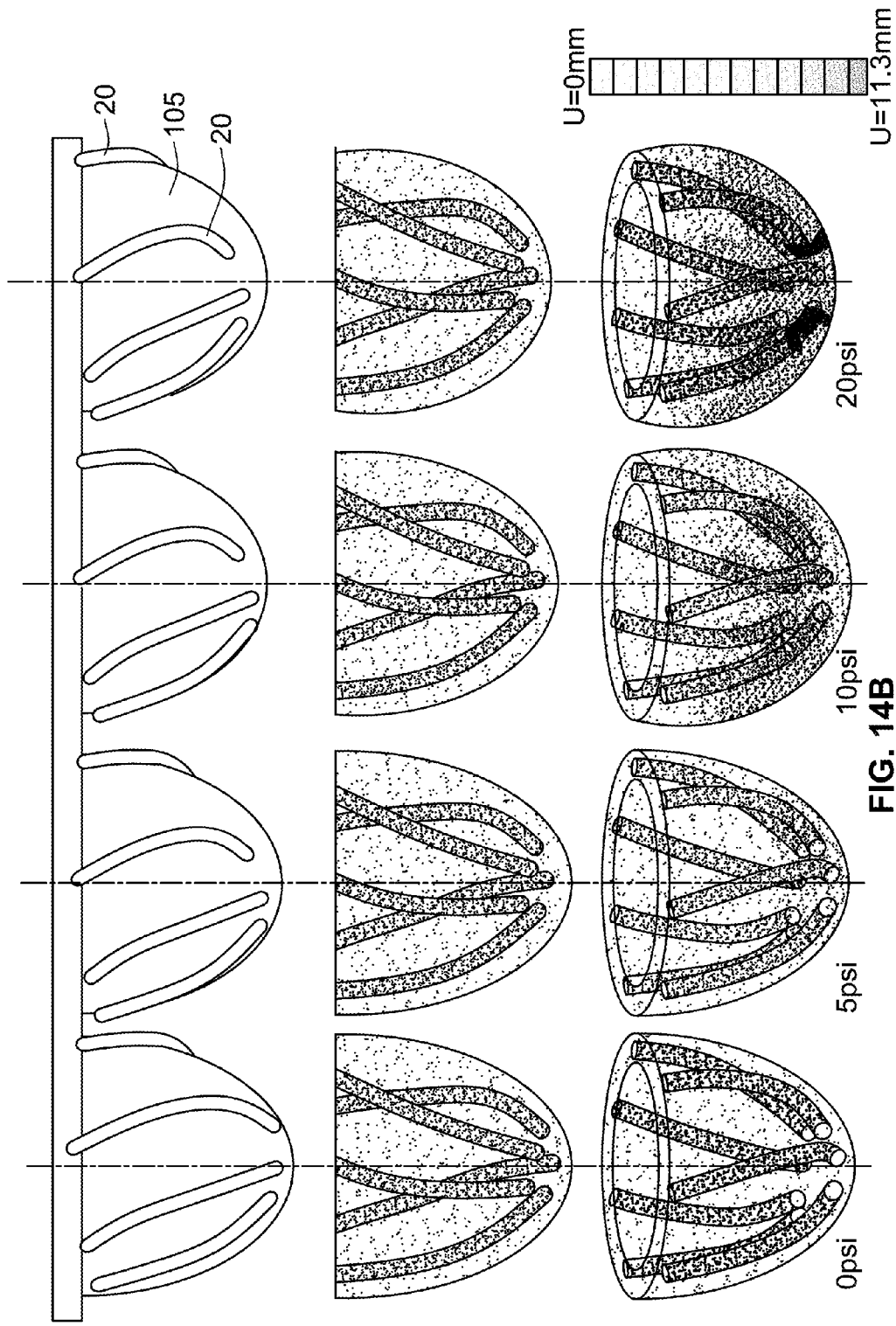
Figure 14C:
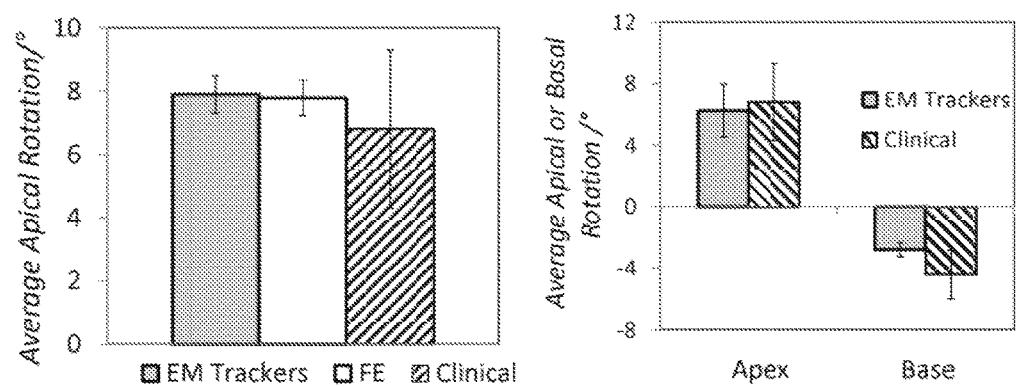

Once the modeling approach was validated, a three-dimensional finite element model that represented a simplified version of the left ventricular (LV) structure (FIG. 14(b)). Specifically, an ellipsoid LV geometry was generated in Solidworks (Dassault Systemes) using dimensions in the range of a previously reported simplified model (specifically; base to apex 71 mm, wall thickness 10 mm, radius 42 mm). As the sub-epicardial fibres dominate the motion of the left ventricle, the simplified model includes this layer alone (FIG. 14(b)). The elastomeric actuators 20 were oriented in a left-handed helix to mimic the architecture of the fibres of the epicardial layer and were oriented, at an inclination of −60° with respect to the basal plan. Three transverse reference planes (apical, mid and basal) were created in the LV model (FIG. 14(b)) and four equally placed nodes were created on each plane coincident with the outside of the LV wall for outputting displacement data. Simulations were run as described for the 2D specimens. Boundary conditions matched that of the physical prototype with displacement of the nodes at the base fixed in all directions. Positional coordinates of each displacement tracking node were measured for actuation of elastomeric actuators 20 at different pressures. Guided by this numerical simulation, a physical prototype was fabricated with identical dimensions (FIG. 14(b), top) using the aforementioned multi-step molding process described in relation to FIG. 10. Motion was tracked using electromagnetic trackers (3D Guidance 8 system, Ascension Technology Corporation) placed in the LV model at locations corresponding to the displacement tracking nodes in the FE model (Figure S8 of the appended Supporting Information). 2D rotation of each node in the basal and apical plane for incremental pressures was calculated from these co-ordinates using the equation below.

$$\theta_z = \tan^{-1}\left(\frac{y_2}{x_2}\right) - \tan^{-1}\left(\frac{y_1}{x_1}\right)$$

The FE model predicted an apical rotation of 7.78°±0.55° (average of rotations for four nodes corresponding to EM trackers) when the LV is rigidly supported at the base, corresponding to the experimental boundary condition. Experimental measurements on the physical prototype closely matched that of the FE model with an agreement of 98.5%. The average experimental rotation was 7.89°±0.59° (see, e.g., FIG. 14(c)). Differences between numerical and experimental results are likely due to slight discrepancies in sensor positioning in the physical prototype. Discrepancies are lower than the 2D test specimens because the electromagnetic trackers are smaller and more accurate than optical marker tracking Both numerical and experimental values for rotation fall within the ranges of clinical values of 6.8°±2.5°. Furthermore, when the physical model was supported by a flexible band rather than a rigid clamp at the base to allow apical and basal rotation, apical rotation of 6.25°±1.73° (counterclockwise when viewed from apex) and basal rotation of 2.78°±0.45° (clockwise) could be achieved, again falling within the range of clinical values for apical and basal rotation respectively (6.8°±2.5° and 4.4°±1.6°) (FIG. 14(c)). The validation of the FE model with experimental testing, and the close correlation of both with clinical data is a key result that demonstrates the applicability of this class of materials.

Left ventricular twist is a useful index of cardiac performance and myocardial mechanics, and can be affected by a range of diseases. For example, if muscles are injured by ischemia, they can be rendered non-contractile, leading to local akinesia (no motion) or dyskinesia where there is local movement that opposes that of the viable myocardium. The three-dimensional simulation and physical prototype developed were also used to explore how damage to individual contractile elements can result in akinetic motion. This could be accomplished by selective deactivation of the elastomer actuators 20, representing a transmural infarct where all sup-epicardial and sub-endocardial fibres are injured by ischemia, and rendered non-contractile.

Figures 15A, 15B, 15C:
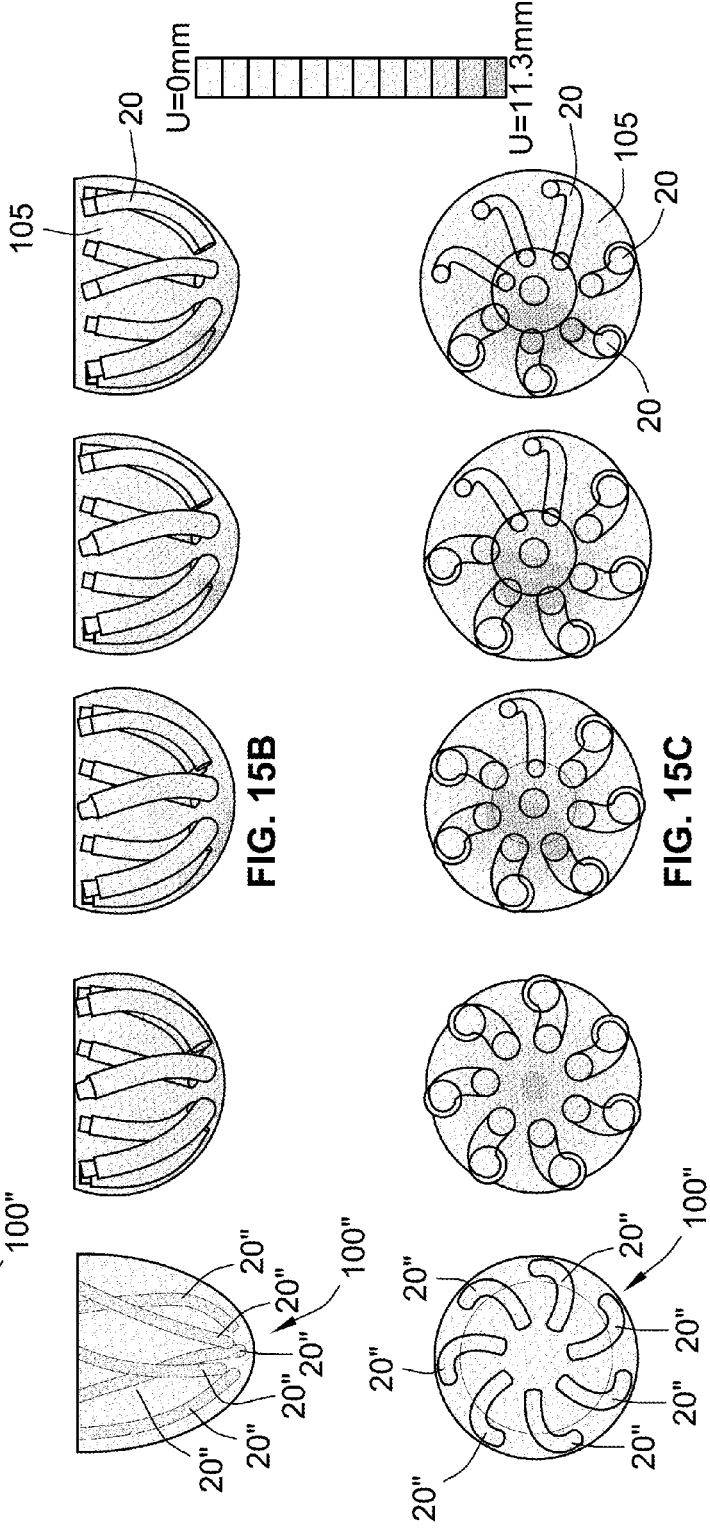
FIGS. 15(a)-15(e) show, in accord with at least some aspects of the present concepts, (a) FE model showing sequential deactivation of elastomeric actuators (all at 20 psi), (b) displacement contour plot for each case at 20 psi viewed from anterior view, (c) displacement contour plot for each case at 20 psi viewed from apex view, (d) physical prototype at 20 psi with 0, 1, 2 and 3 muscles deactivated, and (e) total rotation for FE model and experimental showing a decrease in rotation of markers 1 and 2 that lie in the "akinetic region".
Figure 15D:
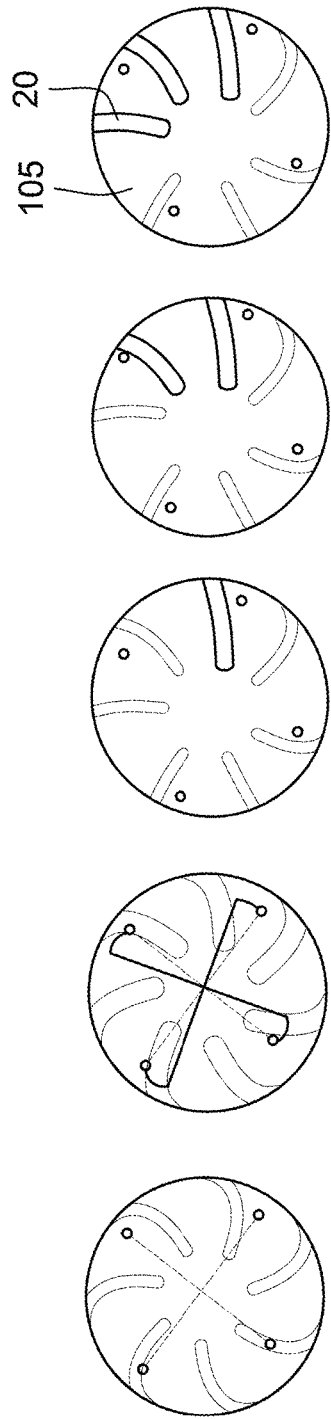

FIGS. 15(a)-15(e) highlight the ability of a left ventricle simulator in accord with at least some aspects of the present concepts to selectively activate and deactivate individual soft actuators 20 in both numerical simulation (see, e.g., FIGS. 15(a)-(c)) and the experimental model (e.g., FIG. 15(d)). From left to right, the first column (leftmost images in FIGS. 15(a)-15(d)) shows a static representation of the left ventricle simulator soft actuators 20 (FIG. 15(a)), left ventricle simulator simulation (FIGS. 15(b)-15(c)) and the left ventricle simulator model 100 (FIG. 15(d)), where the pressure to each of the soft actuators 20 is zero. In the second column, all soft actuators 20 are active responsive to a pressure of 20 psi. As shown particularly in FIG. 15(d), second column, an angular displacement is caused by actuation of the soft actuators 20 and resultant torsional forces. In the third column, six soft actuators 20 are active responsive to a pressure of 20 psi, while one soft actuator 20' is inactive. In the fourth column, five soft actuators 20 are active responsive to a pressure of 20 psi, while two soft actuators 20' are inactive. In the fifth column, four soft actuators 20 are active responsive to a pressure of 20 psi, while three soft actuators 20' are inactive.

Figure 15E:
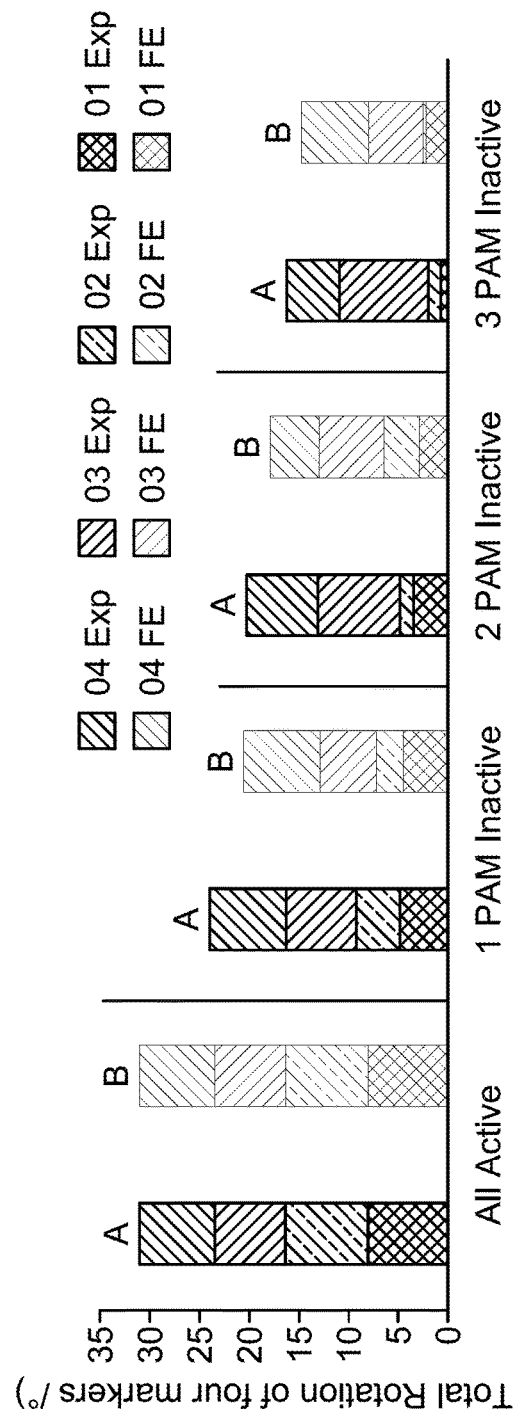

Pathological motion was simulated by setting isotropic thermal coefficients of selected elastomer actuators 20 to zero in FE model and by disconnecting the air supply for the deactivated muscles in the physical prototype. The plot in FIG. 15(e) shows the total rotation from each of the four markers in the apical plane (FE simulation and experimental measurements) as the elastomer actuators 20 are sequentially deactivated. As shown, overall rotation decreases as elastomer actuators 20 are deactivated sequentially. The discrepancy between simulation and experiment is likely due to slight movement of the marker positions when deactivating the elastomer actuators 20in the physical prototype. As the results demonstrate, the contribution to rotation from markers 1 and 2, (positioned in the region where elastomer actuators 20 were deactivated) decreases with each elastomer actuator deactivation. Although this trend is evident for markers 1 and 2, it is more significant for marker 2 (positioned between 2 muscles that are ultimately deactivated) than marker 1 (positioned beside activated and deactivated elastomer actuators 20). This is analagous to a higher reduction in rotation in an infarcted region (akinetic motion) compared to a lower reduction in a peri-infarct or border zone region (dyskinetic motion) of an ischemic heart.

Described above are the simulation, fabrication and experimental characterization of a soft active material concept comprising linear contractile elements borne by (e.g., embedded in) a substrate (e.g., an elastomeric substrate). A finite element based methodology was developed and validated for simulating such composite materials. A case study was presented that was inspired by the structure and dominant muscle layer of the myocardial architecture of the left ventricle. The present inventors demonstrated that, by mimicking the orientation of the contractile elements in a soft material in shape similar to the left ventricle, an accurate representation of apical twist could be achieved. Furthermore, it was showed that the approach could be used to predict the effect of damage to a select number of contractile elements on cardiac motion by selectively disengaging a number of actuators 20. Due to the fact that physiological or pathological twist has a critical impact on the performance of implantable cardiac devices such as prosthetic valves and tissue defect repair devices, an ideal bench-top cardiac simulator would mimic the soft and active contractile motion of the natural heart tissue and be capable of replicating physiological and pathological motions. Here, the inventors demonstrate a soft cardiac simulator with an actively twisting component whose motion agrees well with numerical simulation and physiological clinical ranges. Given that the majority of therapy delivered to treat cardiac disease is associated with pathological motion, the ability to generate pathological-like motion with the simulations and experiments disclosed herein was also demonstrated by deactivating select actuators 20 (e.g., PAMs), a key feature not present in other silicone models.

Looking beyond the exemplification of the left ventricle simulator, the possible applications for this tunable platform of soft actuated materials are vast. The method of fabrication is simple, low cost and flexible. It was demonstrated that, by varying the matrix material, the number of actuators, actuator spacing and degree of actuation, the motion can be tuned to match both physiological and pathological motion. In addition to increasing understanding of these motions, this material platform can function as a test-bed for therapeutics and education. Additionally, as the elastomer actuators 20 can be further actuated, the platform could have potential as a device for the mechanical assist or replacement of organs. The elastomeric materials used in the creation of these soft active materials has a modulus on the order of 125 kPa which is closely matched to that of biological tissue and is thus inherently safe compared to other robotic approaches. Further tuning of the material platform could involve using an inhomogeneous or graded modulus matrix to program the compliance of the material, or using other actuator types to achieve additional degrees of freedom.

Experimental Section

Experimental Characterization of Actuators: In order to characterize longitudinal shortening and radial expansion of the actuator, one end was fixed as it was inflated to a given pressure. Length and diameter of the actuator were measured at each pressure increment. Young's modulus of the elastomer actuators 20 was determined at a range of pressure increments on a mechanical tensile tester (Instron 5566, 2 kN load cell) at a grip-to-grip spacing of 50 mm gauge. The crosshead was manually lowered to zero force, and then returned to the original gauge length at a speed of 200 mm/min while measuring force (Figure S2 of the appended Supporting Information).

Experimental Characterization of Test Specimens: Specimens were gripped by rigid ends in a mechanical tensile tester (Instron 5566, 2 kN load cell). Pressure used to actuate elastomer actuators 20 was varied with a regulator (Campbell Hausfeld) and measured with a sensor (Balluff BSP000W). A photo was taken at each pressure with a remote-controlled camera positioned at a fixed distance from the test specimen. Optical trackers were then tracked with a camera and a customized Matlab script in order to output axial and radial strain at each pressure (Figure S4 of the appended Supporting Information).

FE Model of Test Specimens and Left Ventricle: Quadratic tetrahedral solid hybrid elements (ABAQUS standard element type C3D10H) were used. Under large strains, Ecoflex 00-30 behaves as a hyperelastic material but strains encountered in the experiments presented are within the linear elastic range (<10%) so it was modeled as a linear elastic material with properties from supplier material data sheets (density of $1.07 \times 10-9$ g/cm3 and Young's modulus of 68.9 kPa, the tensile strength at 100% strain) and a Poisson's ratio of 0.499. A linear elastic model was also used for the PAMs. Young's modulus of the elastomer actuators 20 was experimentally determined by measuring force length slope of inflated elastomer actuator at various pressure increments (Figure S2 of the appended Supporting Information). The composite density of the actuator was derived by the volumetric percentage of its components (elastomer, mesh, and air) and calculated at $0.45 \times 10^{-9}$ g/cm3. Air supply tube geometry and inactive ends were incorporated into the model and assigned appropriate material properties and a coefficient of thermal expansion. For the test specimens, the accuracy of the mesh was ascertained through a mesh refinement study, resulting in a mesh seeding size of 1.5 mm in the matrix and elastomer actuators 20, and 4.9 mm throughout clamped ends. For the left ventricle seeding size was 3.2 mm. Displacement of the nodes on the clamped ends of the samples was fixed for test specimens, and nodes at the base of the left ventricle were fixed. Orientation assignment for the PAMs in the left ventricle model is described in Supporting Information.

Experimental Characterization of Motion: Motion tracking of the physical prototype was achieved with the 3D Guidance trakSTAR (Ascension Technology Corporation) and Model 90 6DOF freedom sensors (0.9 mm). The transmitter and base of heart were fixed in one plane using a customized plastic holder so that the apex was free to move. One sensor was placed at the center of the base plane, and assigned as the origin. Each of eleven additional trackers were then placed at molded alignment features on the LV and finely, symmetrically positioned with Cubes software (Ascension Technology Corporation). Insertion into the elastomer was achieved by piercing a hole with a 22 gauge needle then inserting the 0.9 mm trackers so that elastomer would self-seal around the trackers, enabling them to be secured to the elastomer. The LV was actuated in discrete pressure steps and positional data was acquired 5 times at each pressure.

Described herein are DCC devices 100 that replicate heart motion, but do not invert the normal curvature of the heart, thereby holding promise to minimize friction, assist myofibril shortening and promote "reverse remodeling" from prolonged ventricular unloading. The disclosed DCC devices 100, utilizing one or more soft actuators 20 integrated with or attached to a substrate (e.g., fabric, elastomeric structure, sheet material, tissue (e.g., granulation tissue), or other biocompatible flexible substrate), can actively assist both systolic and diastolic function, which can be particularly advantageous in the treatment of heart failure.

FIG. 16(*a*) shows a DCC device 100 having three circumferentially arranged soft actuators 20'. Although the soft actuators 20' may be arranged to advantageously extend around the entire DCC device 100 (e.g., about 360° coverage), the soft actuators 20' may be arranged to extend around a lesser circumferential portion of the DCC device 100 (e.g., less than 360° such as, but not limited to, 345°, 330°, 315°, 300°, etc.). In yet other aspects, the soft actuators 20' may be configured to wrap around the DCC device 100 at a slight angle. For example, a single soft actuator 20' can circumscribe an angle of 540°, with a distal portion of the soft actuator 20' being displaced above, below, or at a greater radius than, a proximal portion of the soft actuator. In still other aspects of the present concepts, a plurality of soft actuators 20' may be serially provided to form, in combination, a generally toroidal actuator set, such as is shown by way of example in FIG. 24.

FIG. 16(*b*) shows another DCC device 100 in accord with at least some aspects of the present concepts, wherein a plurality of soft actuators 20 (i.e., more than one) are disposed curvilinearly along the DCC device an apex 101 of the DCC device toward a base 102 of the DCC device. Although the soft actuators 20 are shown to extend to the base 102, the soft actuators are not required to extend to the base 102 and one or more, or all, of the soft actuators may optionally extend to a point between the apex and base (e.g., a midpoint, etc.). As previously noted, in this configuration of DCC device 100, the soft actuators are configured to deliver torsional forces to an object (e.g., a heart) about which the DCC device 100 is disposed. In at least some aspects of the present concepts, the soft actuators 20 are disposed generally helically along the DCC device 100 from the apex 101 of the DCC device to the base 102 of the DCC device.

Although each of the soft actuators 20 in FIG. 16(*b*) are shown to follow substantially the same curvilinear path from the apex 101 to the base 102, such uniformity is not necessary required and one or more soft actuators may be disposed along a different curvilinear path than others of the soft actuators. By way of example, a first set of soft actuators 20, the set comprising one or more soft actuators, may be disposed to follow a first curvilinear path from the apex 101 to the base 102 and a second set of soft actuators 20, the set comprising one or more soft actuators, may be disposed to follow a second curvilinear path from the apex to the base. In yet another variant, one or more of the soft actuators 20 following a curvilinear path from the apex 101 to the base 102 may instead a combination of two or more serially-disposed actuators that are independently actuatable relative to one another.

It is to be noted that the soft actuators 20' shown in FIG. 16(*a*) may be fully embedded within the substrate 105', partially embedded within the substrate, or attached to the substrate (e.g., adhesively, mechanically, etc.). Likewise, the soft actuators 20 shown in FIG. 16(*b*) may be fully embedded within the substrate 105, partially embedded within the substrate, or attached to the substrate (e.g., adhesively, mechanically, etc.).

For example, where the soft actuators 20' attach to a substrate 105', as opposed to being formed within or disposed within a substrate, the substrate 105' may comprise a plurality of uniformly spaced-apart loops (e.g., a grid of webbing, such as a PALS structure) through which the soft actuators 20' pass. Likewise, where the soft actuators 20 attach to a substrate 105, as opposed to being formed within or disposed within a substrate, the substrate 105 may comprise a plurality of spaced-apart loops, which may be non-uniform owing to the curvilinear paths traversed by the soft actuators 20, through which the soft actuators 20 pass.

Figures 16A, 16B:
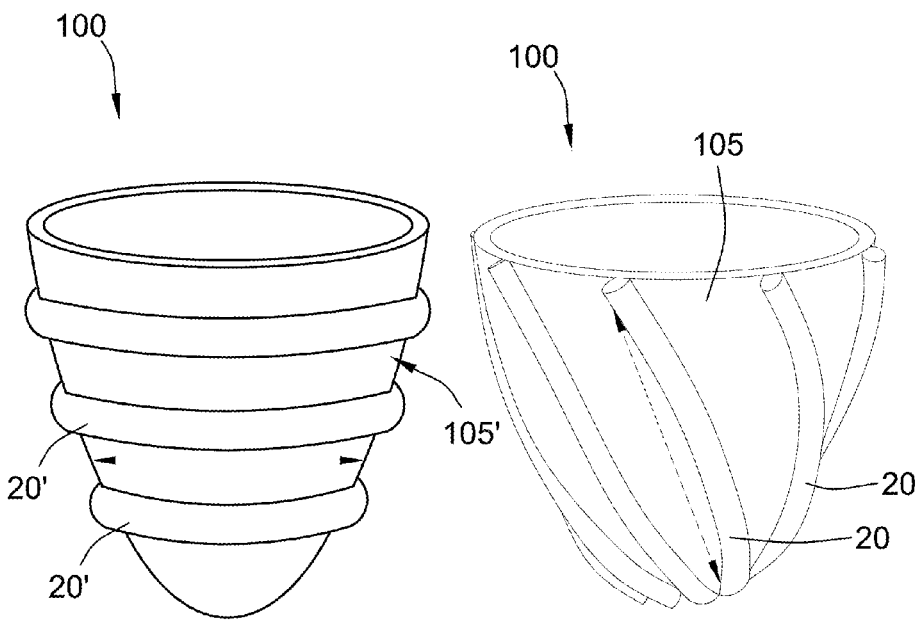
FIGS. 16(a)-16(e) show aspects of a direct cardiac compression (DCC) device in accord with at least some aspects of the present concepts, including (a) a first portion configured to apply compressive and/or extensive forces, (b) a second portion configured to apply torsional (twisting/untwisting) forces, (c) a combination of the first and second portions (a), (b) to enable application of, compressive, extensive and/or torsional forces on a heart when positioned on ventricles of a heart, as depicted in FIGS. 16(d)-16(e).

In yet other aspects, the soft actuators 20, 20' shown in FIGS. 16(a)-16(b) may be both disposed in a space defined between opposing substrates 105, 105' (i.e., disposed between an inner substrate and an outer substrate), with spatial retention of the soft actuators 20, 20' accomplished by physical connections between the soft actuators 20, 20' and one of, or both of, the opposing substrates 105, 105'. Such physical connection may comprise any biomedically-suitable physical connection (e.g., spacers, loops, stitching, adhesive, vacuum seal of the soft actuators between opposing substrates, compressive forces applied by a connected mesh 130, such as is shown in FIG. 16(e), etc.). In still another aspect, the substrates (e.g., 105, 105') may be dispensed with entirely in favor of proximal and distal anchor points (e.g., an apex stabilizer clamp, such as a Medtronic Starfish heart positioner, and a basal band) and a soft lattice of spacers that maintain spatial alignment of the soft actuators 20, 20' relative to one another.

Figures 16C, 16D:
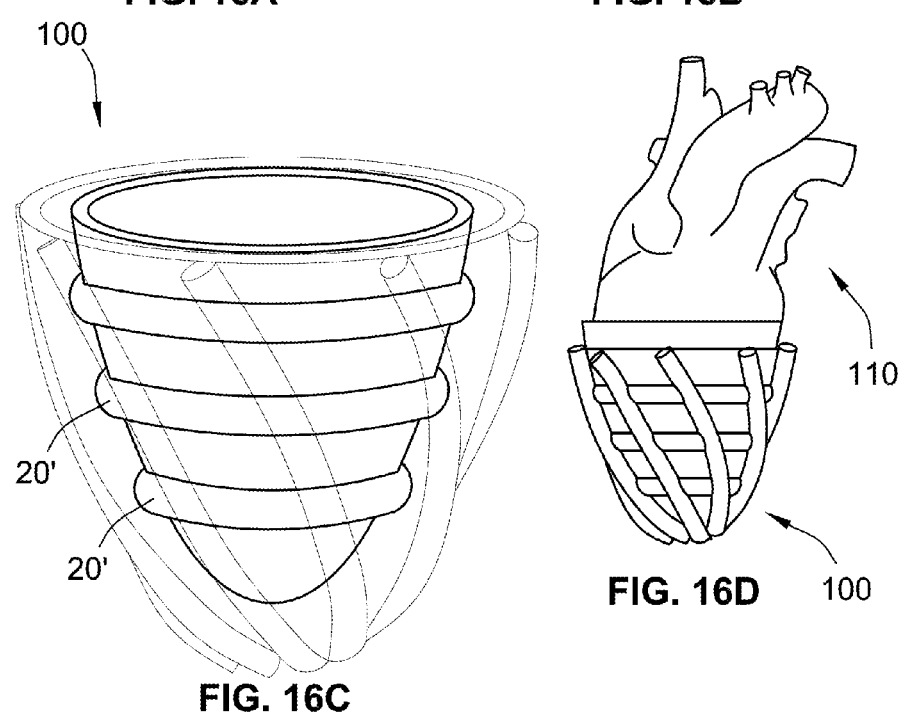
Figure 16E:
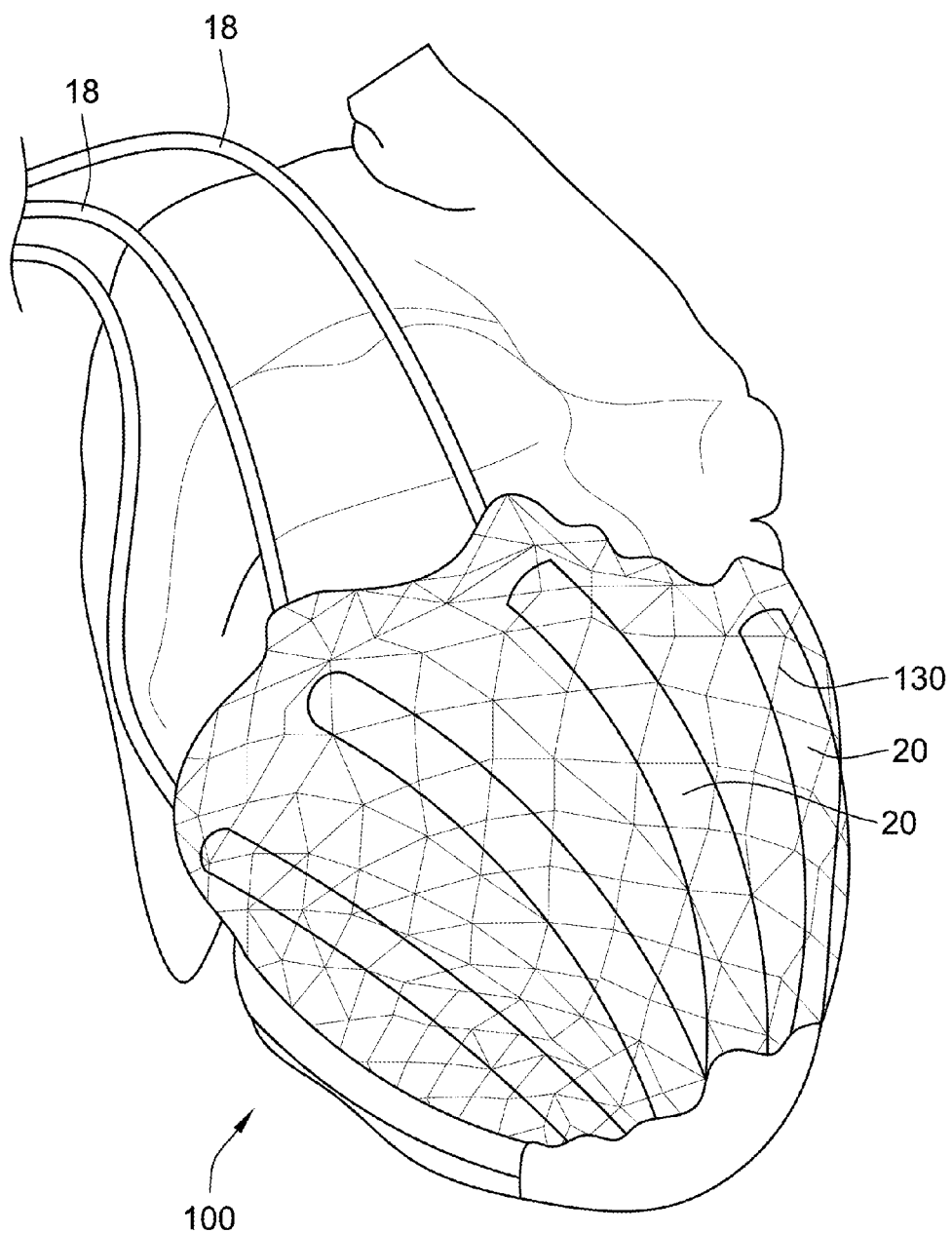

FIG. 16(c) shows a combination of the DCC devices 100 of FIGS. 16(a)-16(b), wherein a first DCC device of FIG. 16(a) is inserted into a second DCC device of FIG. 16(b) to yield a composite DCC device 100, as shown. Alternatively, in another embodiment, a first DCC device of FIG. 16(b) is inserted into a second DCC device of FIG. 16(a) to yield another composite DCC device 100 (not shown). In at least some aspects of the present concepts, each of the first and second DCC devices 100 are independent actuatable and, further, each of the soft actuators 20, 20' are independently actuatable. In still additional aspects of the present concepts, selected soft actuators 20, 20' are ganged together for simultaneous actuation to yield a desired biomimetic effect.

FIG. 16(d) shows the composite DCC device 100 of FIG. 16(c) disposed about a lower portion of a heart 110. FIG. 16(e) shows a composite DCC device 100, such as that depicted in FIGS. 16(c)-16(d) disposed about a lower portion of a model heart 110. As shown, the DCC device 100 comprises a biocompatible or bioinert fabric or mesh 130 (e.g., medical grade of polyethylene, polypropylene, polyurethane, etc.) disposed around the curvilinearly disposed soft actuators 20. In at least some aspects, the mesh 130 is disposed to apply compressive forces to the underlying soft actuators 20 to bias the soft actuators against an underlying substrate (e.g., substrate 105' in FIG. 16(a)), which may optionally have guides or alignment features provided thereon. In another aspect, the mesh 130 is mechanically connected to the soft actuators 20 by biocompatible or bioinert connection members (e.g., sutures, bands, ties, or the like). FIG. 16(e) also shows air tubes 18 extending from each of the soft actuators 20. It is to be noted that the tubes 18 (which could convey air, helium, liquid, etc.) can be disposed to enter the actuators 20 (or actuators 20', 20" described herein) at any point (e.g., a proximal end, a distal end, or a point intermediate thereto) and are not limited to the illustrated examples.

Figure 17A:
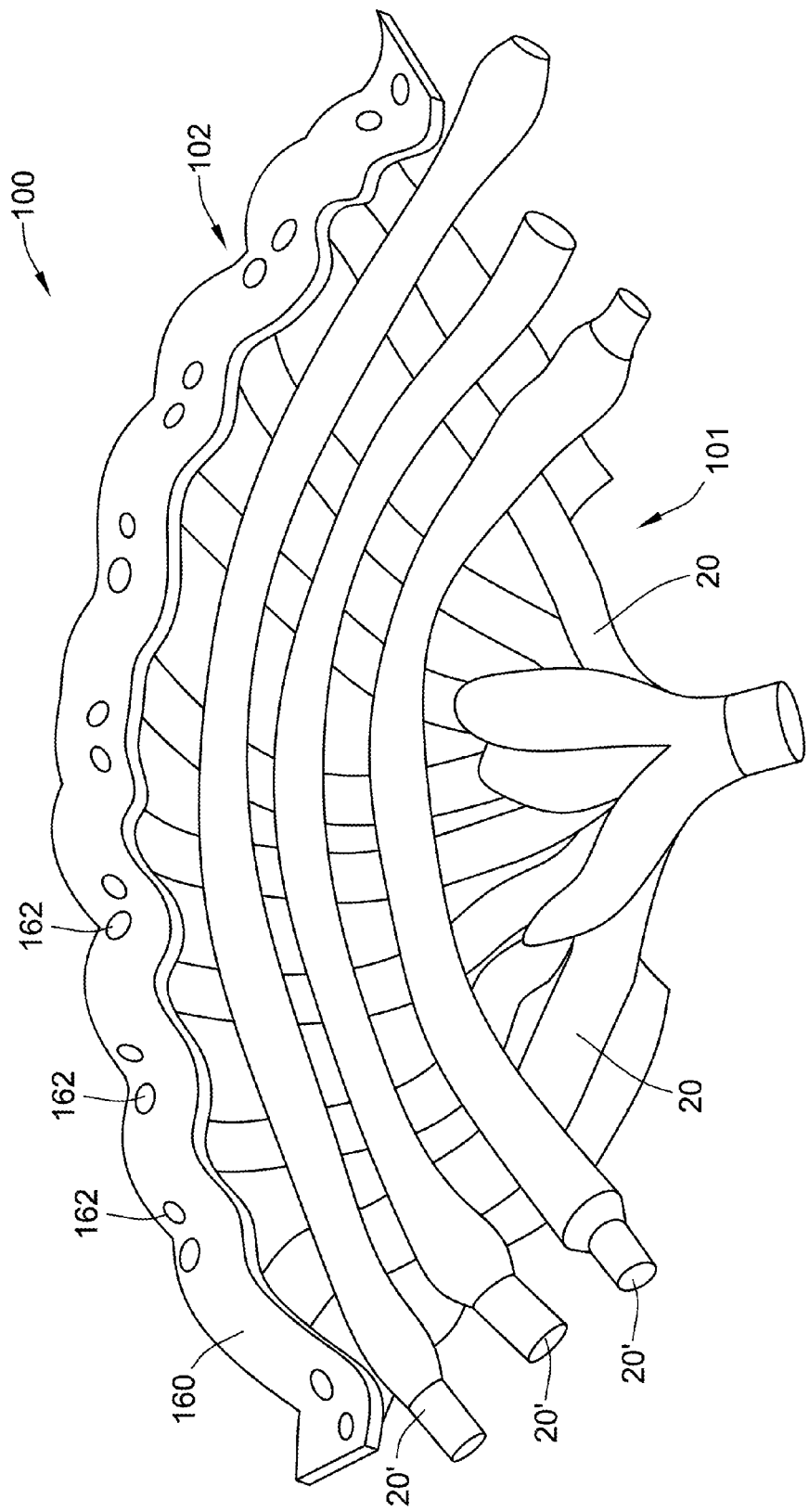
FIGS. 17(a)-17(c) show aspects of another embodiment of a direct cardiac compression (DCC) device in accord with at least some aspects of the present concepts, including (a) a DCC device, configured to provide compressive, extensive and/or torsional forces on a heart, having a substantially planar profile adaptable to be fitted about various sizes and configures of hearts, (b) a side view of the DCC device of (a) wrapped in a configuration to fit over a lower portion of a heart and (c) a top view of the DCC device of (b).
Figure 17B:
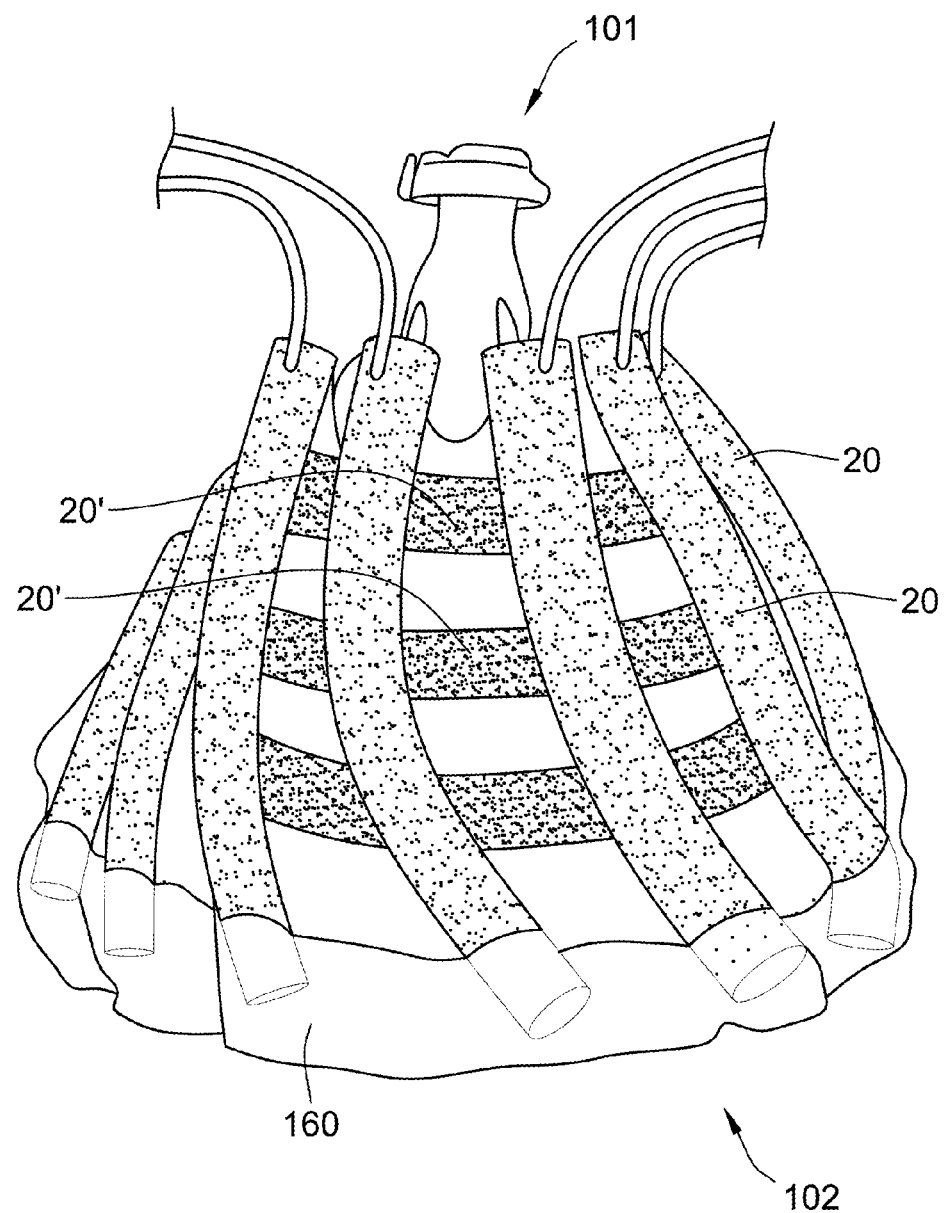
Figure 17C:
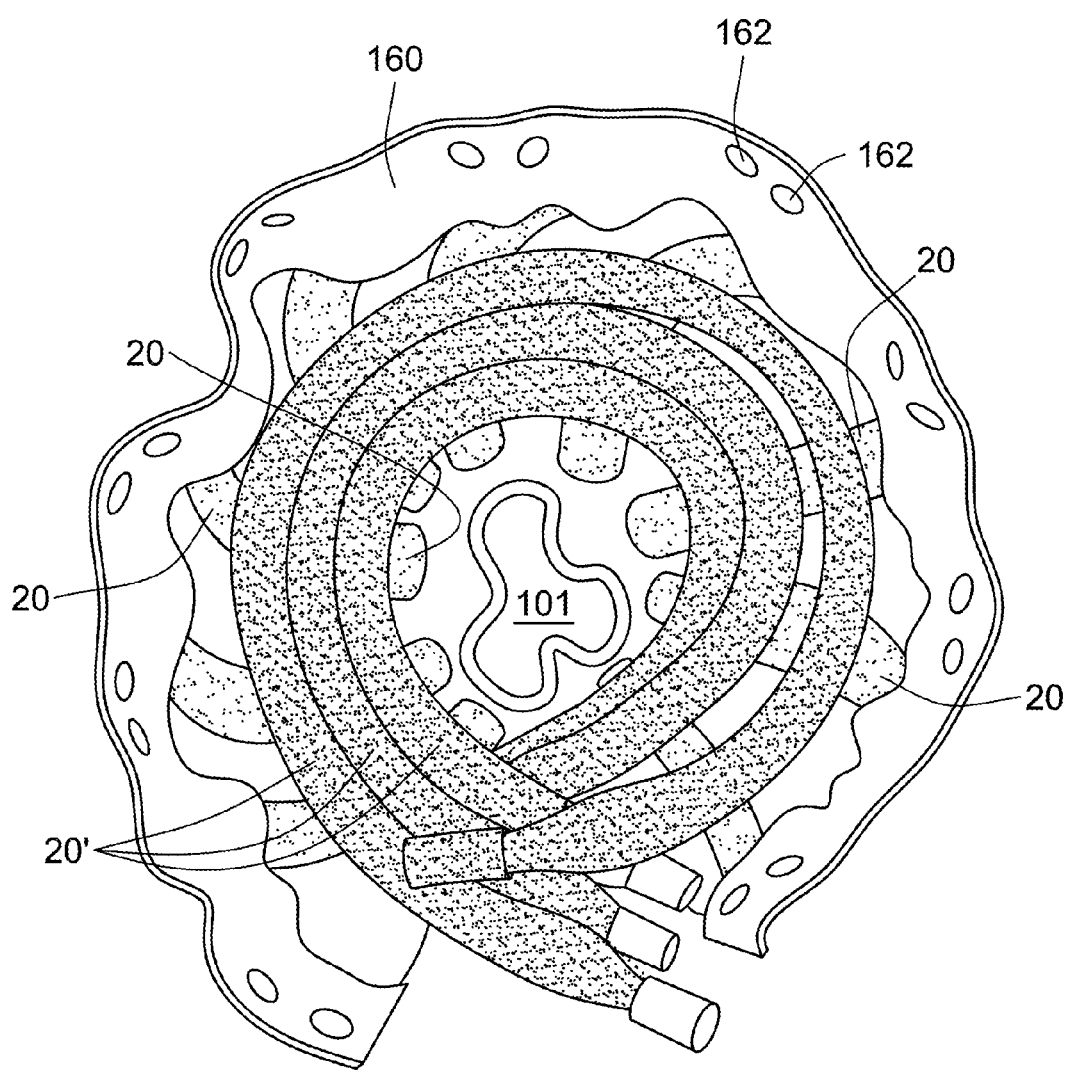

FIGS. 17(a)-17(c) show an example of a DCC device 100, in accord with at least some aspects of the present concepts, wherein the form factor is that of a band or wrap. In the embodiment shown in FIGS. 17(a)-17(c), the band-shaped DCC device 100 is discontinuous, having a first end 150 and a second end 152, such configuration permitting the DCC device to be disposed about an object (e.g., wrapped around the object, such as a heart).

As with the DCC device 100 FIGS. 16(c)-16(e), the DCC device of FIGS. 17(a)-17(c) comprises a plurality of soft actuators 20 disposed curvilinearly (e.g., a helix, involute, spiral, etc.) along the DCC device, from an apex 101 to a base 102 thereof, to deliver torsional forces to an object about which the substrate is disposed, as well as a plurality of soft actuators 20' spaced apart and arranged along the band-shaped DCC device to at least substantially circumscribe an object (e.g., a heart, a generally conical object, a generally semi-circular object, etc.) when the band-shaped DCC device is disposed about the object, to contract to impart compressive forces to the object.

The DCC device 100 further comprises one or more fastening elements to permit securement of at least a first portion of the band-shaped DCC device to another portion of the band-shaped DCC device. In one aspect, connection may be effected between the first end 150 and the second end 152, wherein the first end and the second end each comprise at least one fastening element (e.g., male/female connection elements, eyelets facilitating connection via a connection member disposed through the eyelets, suturable sections in a substrate material facilitating connection via sutures, etc.).

Figure 26B:
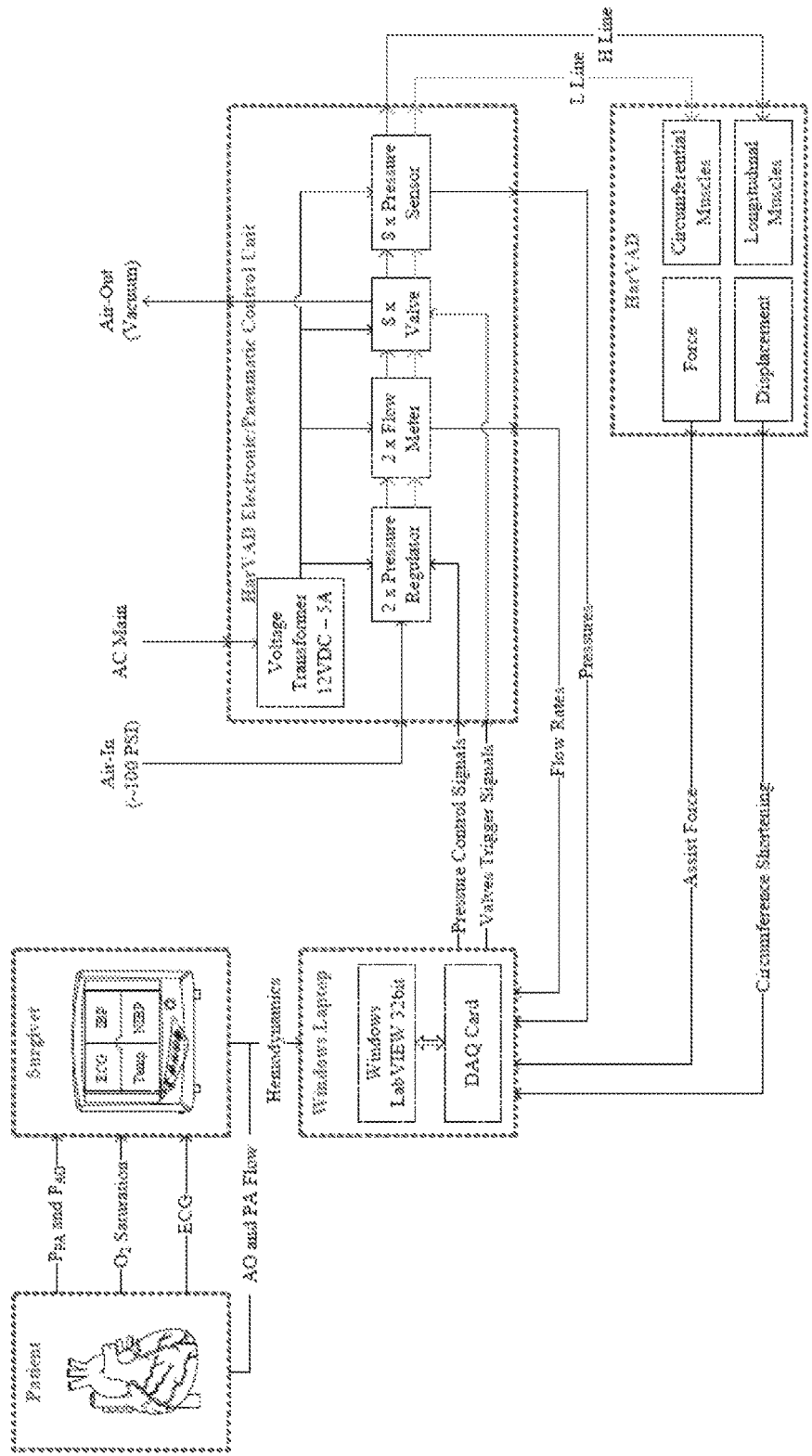
Figure 26C:
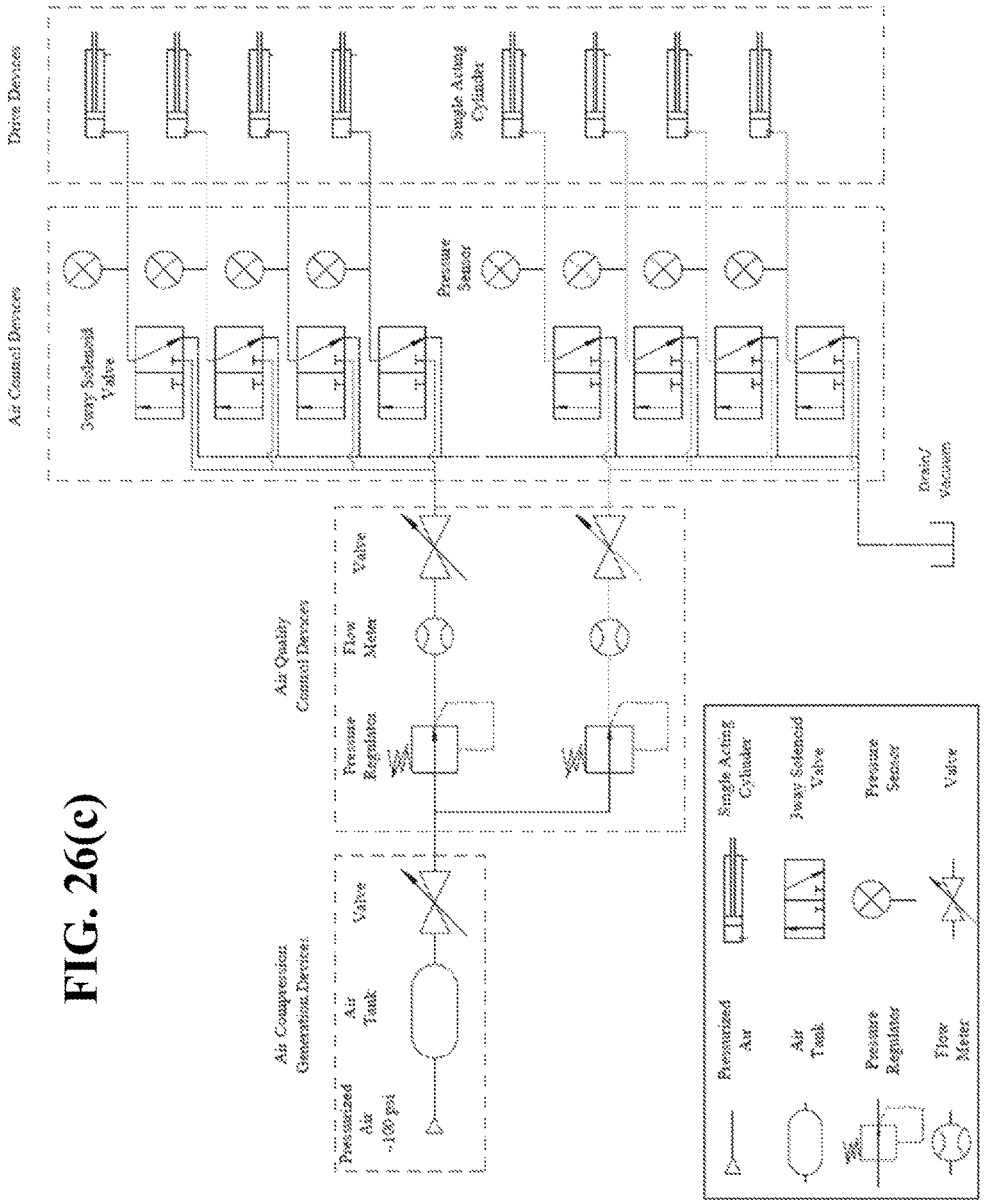

In another aspect, connection may be effected between a first portion of a basal band 160 and a second portion of the basal band. By way of example, the basal band 160, as depicted in FIGS. 17(a)-17(c) comprises a plurality of reinforced openings 162, such as eyelets. As shown in FIG. 26, one or more connection members 164 (e.g., a cord, wire, ribbon, filament, band, etc.) can be passed through two or more of the reinforced openings 162 to connect the reinforced openings. In one example, a suitable bioinert or biocompatible cord 164 is passed through a plurality of reinforced openings about the basal band 160 such that it may be pulled and secured to draw together and bias the basal band against the object (e.g., a heart) about which the DCC device 100 is disposed.

In another example, a plurality of suitable bioinert or biocompatible cords 164 are passed through a plurality of reinforced openings about the basal band 160 and each cord being pulled and secured to draw together the respective segments of the basal band and thereby bias the basal band against the object (e.g., a heart) about which the DCC device 100 is disposed. In yet another example, one or more connection members 164 may be attached at a first end to a first reinforced opening (e.g., at an anterior end of the DCC device), drawn up and over the object (e.g., a heart), and attached a second end to a second reinforced opening (e.g., at a posterior end of the DCC device). In all respects, the connection members and attachment members described herein are adaptable for selectively controlling a tension between the attached components. In still other aspects, the DCC device 100 may be provided with alternative fixation methods, such as members adapted for attachment to (or acceptance of members adapted for attachment to) the ribs or sternum, adhesives, or Hydrogel.

In FIG. 17(b), the first end 150 (not shown) and the second end 152 (not shown) of the band-like DCC device 100 are connected together to form a generally conical or frustoconical shape. The DCC device 100 in FIG. 17(b) is shown to be resting in an inverted position with the basal band 160 at the bottom and apex 101 at the top. In FIG.

17(b), the soft actuators 20 are shown to have a first end (e.g., a proximal end) 181 at the apex of the DCC device 100 and a second end (e.g., a distal end) 182 terminating at connection members 166 at the basal band 160. The connection members 166, as shown, comprise openings or loops into which the second end of the soft actuators 20 are retained.

In yet another alternative, retention of the band-shaped DCC device 100 in an appropriate shape and/or position may be facilitated by one or more connection elements disposed around, or attached to, proximal and distal ends of the soft actuators 20'. For example, with reference to FIG. 17(c), following positioning of the DCC device 100 around a heart, a proximal end 171 of soft actuator 20' may be secured to a distal end 172 of the same soft actuator 20' by a bioinert or biocompatible connection member (e.g., a band, tie, clamp, etc.). As another example, each of the proximal ends 171 and distal ends 172 of soft actuators 20' are formed with or otherwise comprise one or more attachment points or members enabling use of a single bioinert or biocompatible connection member (e.g., a band, tie, clamp, etc.) to connect (e.g., lock together) all of the soft actuators 20' following suitable positioning of the DCC device 100 around a heart.

FIG. 17(b) shows a DCC device 100 comprising soft actuators 20 formed within a substrate 105 (e.g., a medical grade urethane, nylon, polyethylene, etc.). Similar to the arrangement of FIGS. 16(c)-16(e), another DCC device comprising a substrate 105' and soft actuators 20' is disposed therewithin. FIGS. 17(b)-17(c) further shows, at the apex 101, an apex stabilizer 180 comprising a three-lobed Medtronic Starfish heart positioner.

Figure 18A:
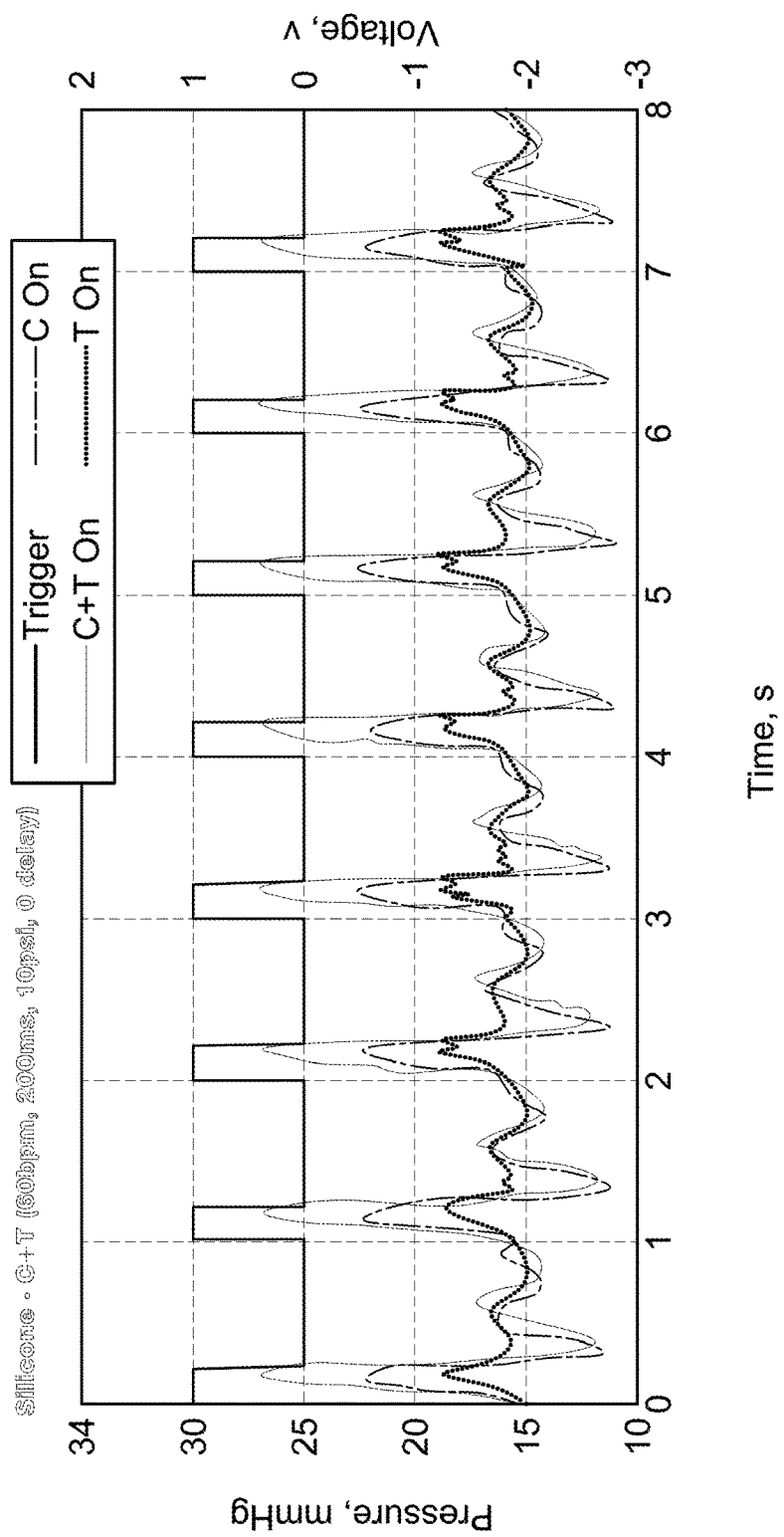
FIGS. 18(a)-18(b) are in vitro testing results for an embodiment of a DCC device according to some aspects of the present concepts, respectively showing a pressure vs. time plot and a flow rate vs. time plot for torsion, compression, and combined torsion and compression.
Figure 18B:
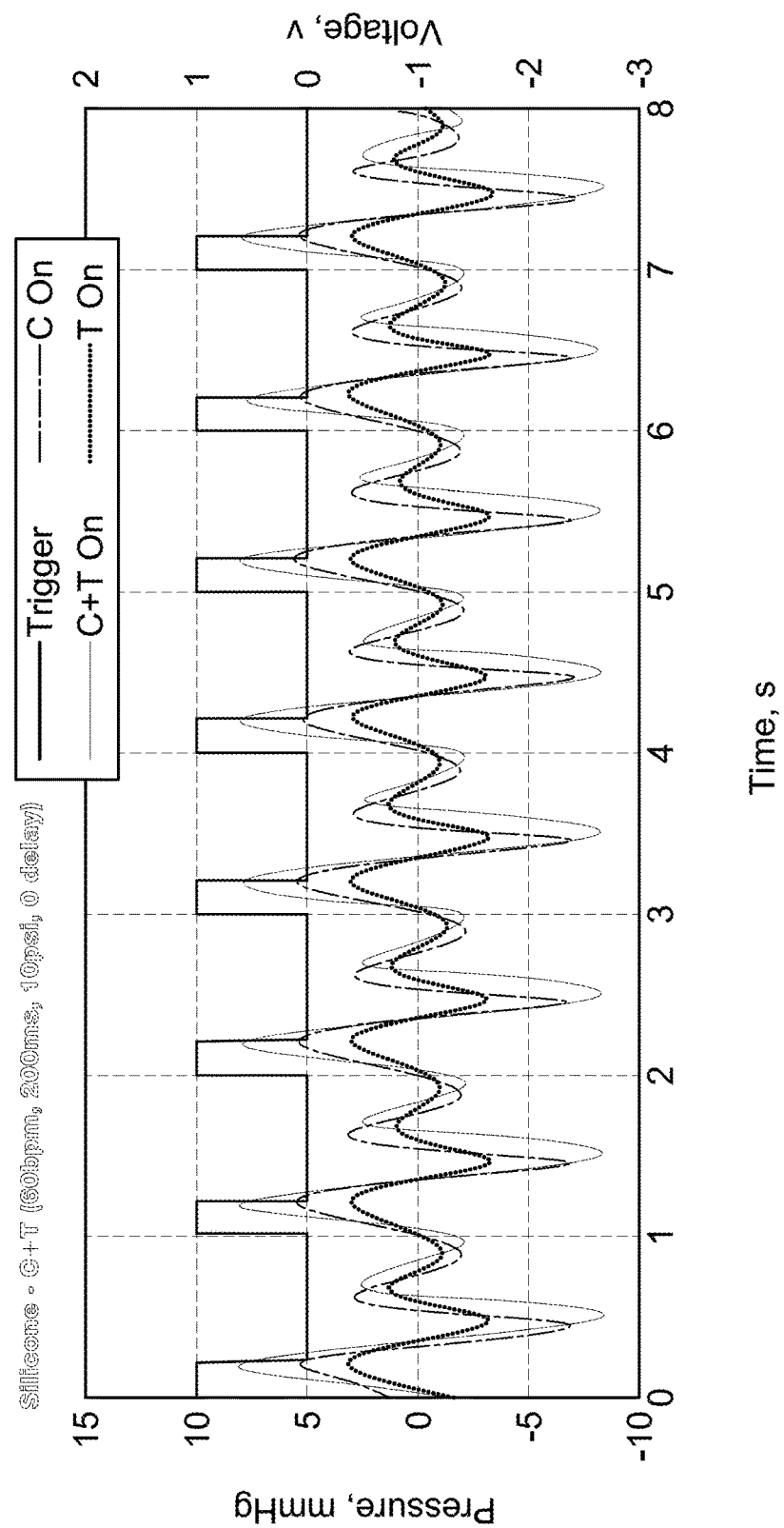

FIGS. 18(a)-18(b) show data for in vitro prototype testing with a synthetic cardiac model. The synthetic cardiac model was sectioned at the atrioventricular groove and the septum was removed. The synthetic cardiac model was mounted on a custom test rig and sealed to an acrylic plate with an outflow tube and the set-up was instrumented with a flow probe (Transonics) on the outflow and a pressure gauge in the ventricle. Values for pressure and flow were taken for a variety of tests in which the effects of different actuation modes were compared, some of the test result being represented in FIGS. 18(a)-18(b). In each of FIGS. 18(a)-18(b), tests were conducted under conditions where only circumferential actuators 20' were actuated, where only torsional actuators 20 were actuated, and where both circumferential actuators 20' and torsional actuators 20 were actuated, following receipt of the trigger signal. For these tests, FIG. 18(a) shows the resulting ventricle pressure (mm Hg) over time, whereas FIG. 18(b) shows the resulting outflow flow rate (L/min) over time. As predicted, the combination of torsional and circumferential actuation, via actuators 20, 20', generated superior pressure (waveform 201) and flow output (waveform 202), as compared to the actuation of the circumferential actuators 20' or the torsional actuators 20 in isolation.

Figure 19:
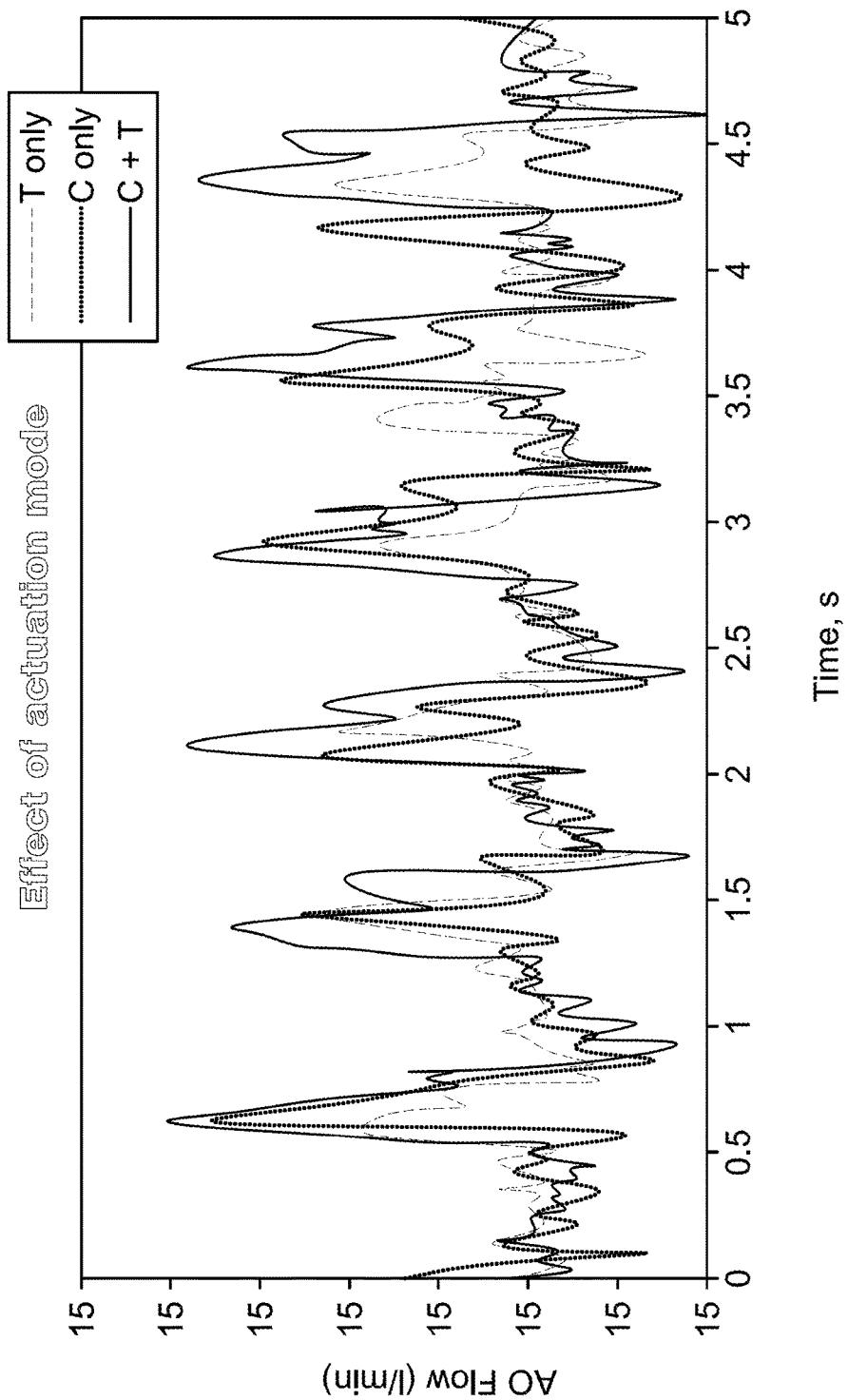
FIG. 19 shows in vivo test results for an embodiment of the DCC device for an embodiment of a DCC device according to some aspects of the present concepts, respectively showing a pressure vs. time plot and a flow rate vs. time plot for torsion, compression, and combined torsion and compression on a healthy functioning porcine heart.
Figure 20B:
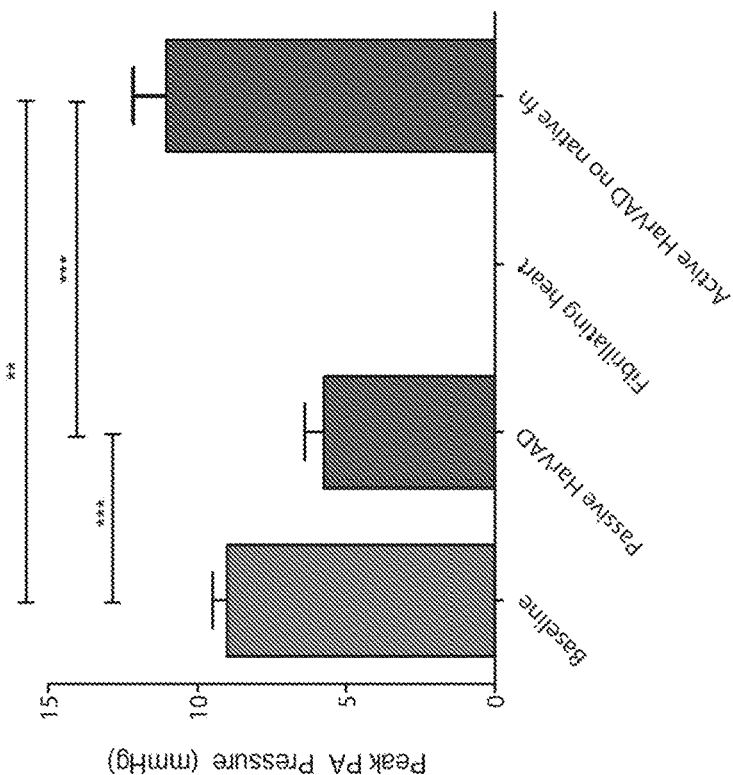
FIGS. 20(a)-20(b) respectively show an effect of mechanical assistance on stroke volume and pressure using a DCC device according to some aspects of the present concepts on a heart without native function.
Figure 20A:
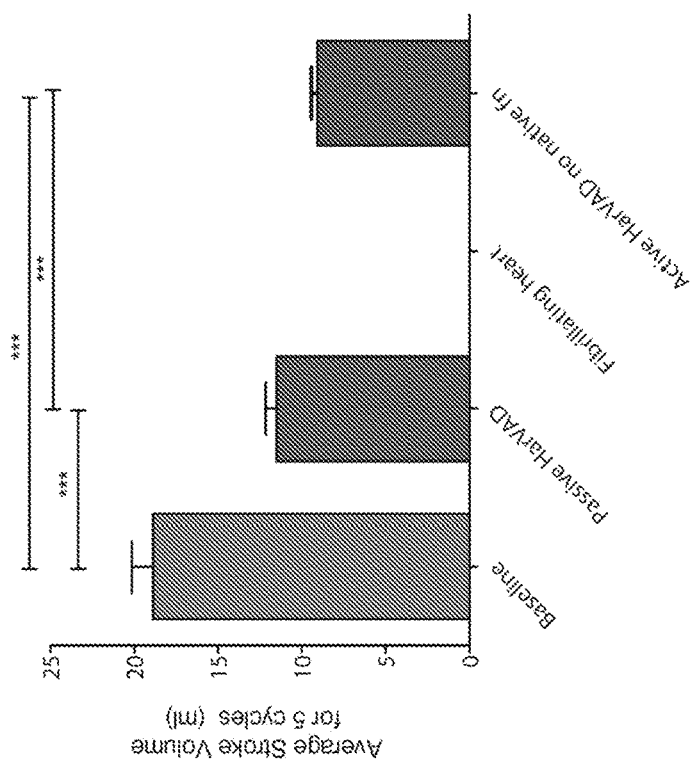
Figure 21A:
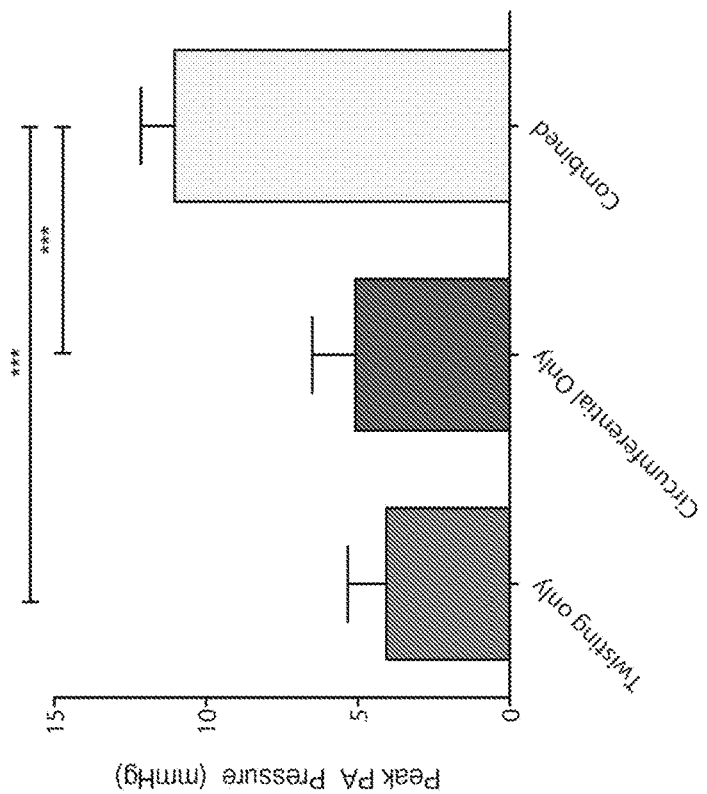
FIGS. 21(a)-21(b) respectively show an effect of actuation mode (twisting only, circumferential only, and combined twisting and circumferential) on stroke volume and pressure using a DCC device according to some aspects of the present concepts on a porcine heart without native function.
Figure 21B:
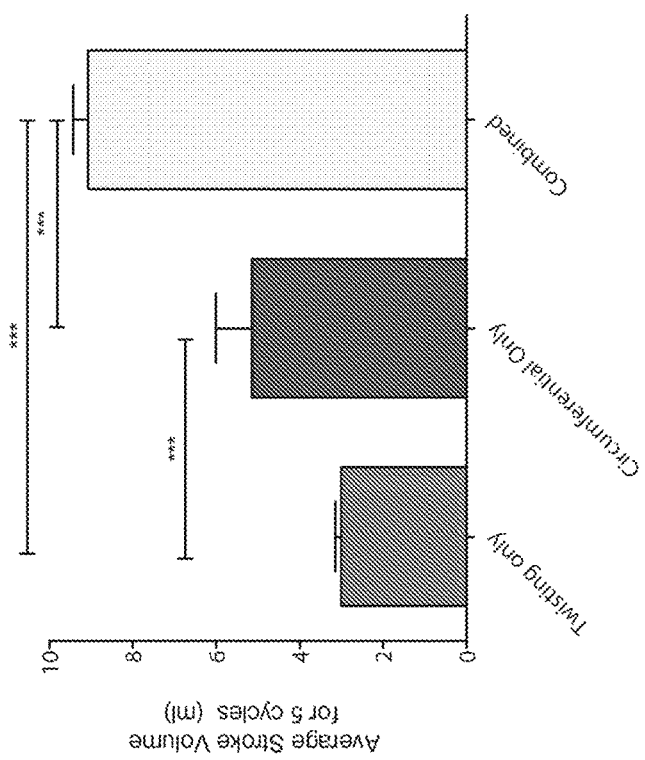

As represented in FIG. 19, Simulated ex vivo porcine testing was completed on DCC devices 100 placed on the hearts of recently deceased animals (n=4) and actuation at a pressure of 10 psi at a rate of 60 beats per minute yielded a pulmonary artery flow rate (aortic flow rate) of up to 4 L/minute were recorded, as recorded with a Transonics® flow probe.

Prototype testing in an in vivo porcine model included two proof of concept tests: (i) using the DCC device 100 as an assist device for a healthy heart under different actuation conditions and (ii) using the DCC device as an acute cardiac resuscitation device. As to the first test, the effect of combined actuation on cardiac output was found to be superior to either actuation mode independently.

Figure 22A:
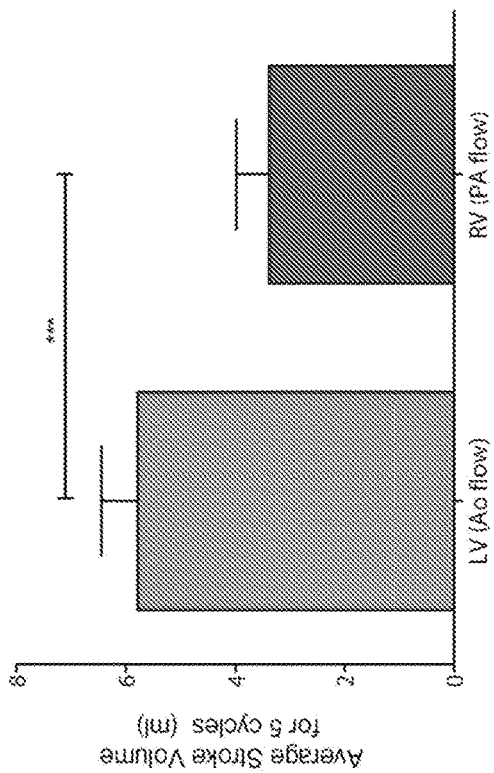
FIGS. 22(a)-22(b) are a demonstration of univentricular or biventricular actuation on a porcine heart without native function, using a DCC device according to some aspects of the present concepts.
Figure 22B:
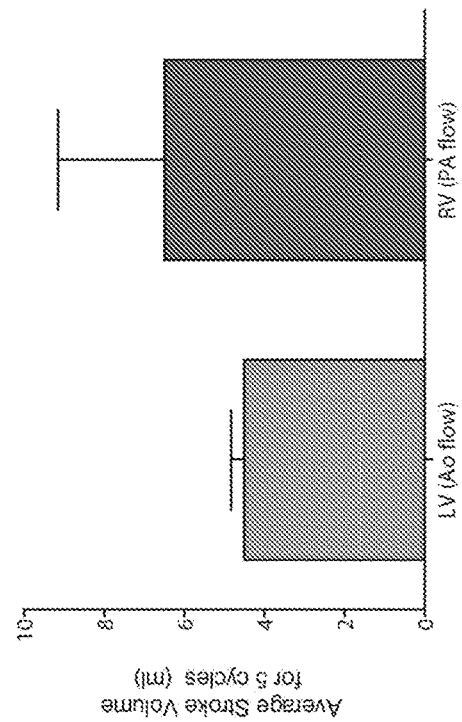

As to the second test, represented in FIGS. 20(a)-20(b) and FIGS. 21(a)-21(b), a baseline was measured on a healthy heart, and then the DCC device 100 was placed on the heart. Without actuation, the stroke volume and pulmonary artery pressure were reduced and the DCC device 100 was removed from the heart. Following fibrillation and confirmation that cardiac output was measurable, the DCC device 100 was placed back on the heart and actuated using the signal from a pacemaker at 100 bpm. With combined circumferential and twisting actuation, via actuators 20, 20', stroke volume was restored to approximately 50% of baseline (FIG. 20(a)), and pressure in the pulmonary artery was restored to greater than baseline (FIG. 20(b)). The effect of combined actuation modes is shown for stroke volume ((FIG. 21(a)) and pressure (FIG. 21(b)). Additionally, the effect of actuating one side of the device only is shown in FIG. 22(a)(left actuation) and FIG. 22(b) (right actuation). In FIGS. 20(a)-21(b), the term HarVAD (i.e., "Passive HarVAD" and "Active HarVAD with no native fn") refers to the DCC device 100.

Figure 23:
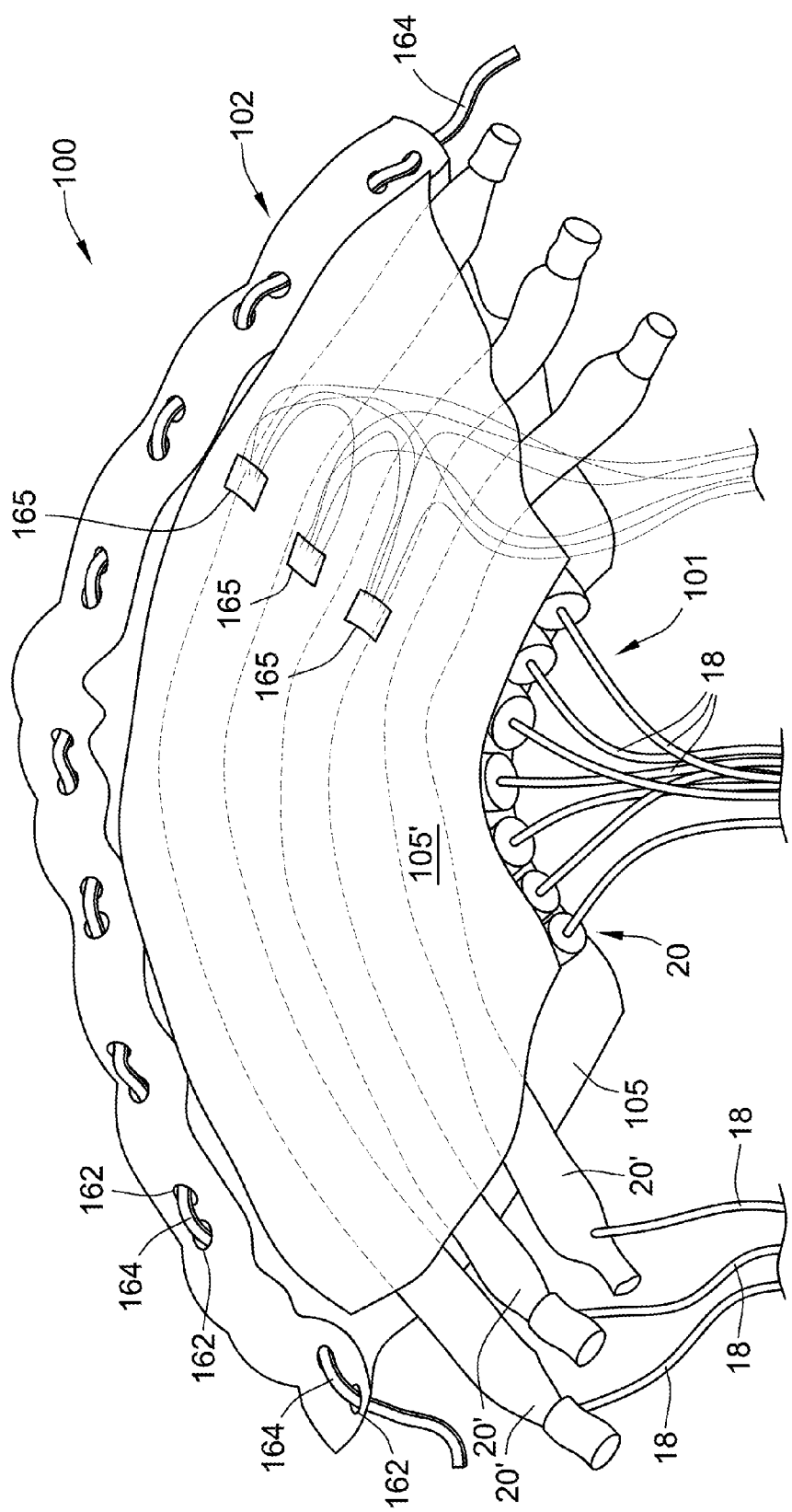
FIG. 23 shows an example of a DCC device in accord with at least some aspects of the present concepts.

FIG. 23 shows a variant of the DCC device 100 of FIG. 17(a) wherein, on an inner surface of the inner substrate 105', a plurality of (e.g., an array of) pressure sensors 165 (e.g., barometers, capacitance sensors or other sensors) embedded in a thin flexible layer that is at the interface of the device and the heart that can output a plurality of localized pressures of the heart or, still more advantageously, a pressure map of the heart. Although FIG. 23 shows three pressure sensors 165 (e.g., a small array) for illustrative purposes, it is envisioned that, in at least some aspects, the substrate 105' would bear an array of sensors substantially covering the entirety of the exposed surface of the substrate.

Figure 24:
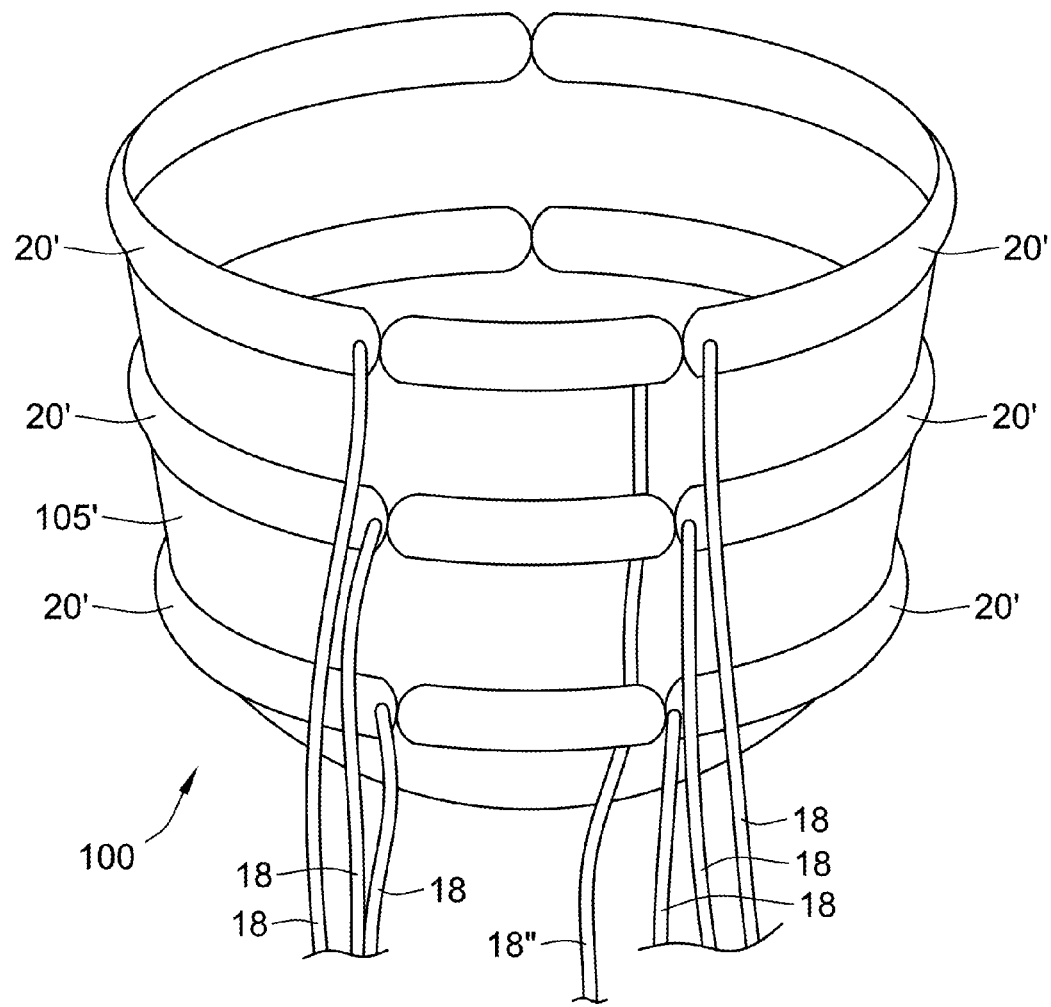
FIG. 24 shows another example of a DCC device, in accord with at least some aspects of the present concepts, wherein static pressurized actuators are provided along the anterior portion for sizing and adjustability.

An advantage of such sensors 165 is that the feedback from the device as to the real-time physiological conditions can permit on-the-fly adjustment of the DCC device 100 in selected portions of the device. For example, if a pressure map indicates that a particular region of the interface between the heart and the DCC device 100 is at a higher pressure or a lower pressure that expected (or desired) at a particular point in a cardiac cycle, adjustments can be automatically or manually implemented to adjust, by way of example and without limitation, any of the actuator 20, 20' actuation sequence, action pressure, or actuation timing. Moreover, in accord with at least some embodiments of the present concepts, the DCC devices 100 may comprise elements (e.g., soft actuators 20") that enable on-the-fly adjustment of the looseness or tightness of various portions of the device. FIG. 24, for example, shows a DCC device 100 having a first set of circumferential dynamic soft actuators 20', as previously described, that are used to impart compressive forces to the heart at desired times (i.e., at desired portions of the cardiac cycle) and a second set of circumferential dynamic soft actuators 20" that are, via the air tubes 18", maintained at a set static pressure selected to provide an appropriate local baseline pressure at an interface between the DCC device 100 and the heart. The static pressure in the circumferential dynamic soft actuators 20" can thus be increased, via the air tubes 18", for tightening (e.g., if the dilated heart started to reverse remodel) or decreased for loosening (e.g., growing pediatric heart). In at least some aspects, as shown in FIG. 24, a plurality of the circumferential dynamic soft actuators 20" are ganged together and are maintained at a common static pressure via a common air tube 18". In at least some other aspects, each of the circumferential dynamic soft actuators 20" is individually controlled via a dedicated air tube 18".

Further to permitting enabling on-the-fly adjustment of the looseness or tightness of various portions of the device, the elements 20" (e.g., actuators, etc.) are manually adjustable, or may be set to self-adjust in accord with one or more programs or modes. For example, in a follow-up visit post-implantation, a medical care provider images the device in situ (e.g., by taking a radiograph) to determine a position and orientation of the device and, based on such information, may adjust one or more of the elements 20" responsive thereto to tighten or loosen one or more actuators (e.g., a circumferential basal actuator 20, 'a circumferential apical actuator 20', etc.). In another example, a pediatric DCC device may require periodic adjustments in fitting, via the elements 20", to accommodate growth over time. In at least some aspects, one or more of the substrate(s) (e.g., 105, 105') and/or one or more of the actuators (e.g., 20, 20', 20") may comprise radiographic markers or other imaging features adapted to facilitate accurate localization of one or more parts of the device.

Yet further, the adjustability of the elements 20" may be set to correspond, in one or more programs or modes, to an activity level of the wearer. For example, a first mode of static pressures may correspond to a sedentary state of the wearer, whereas a second mode of static pressures may correspond to an active state of the wearer. Likewise, the control system for the actuators 20, 20' may similarly advantageously adapt as between a plurality of modes to provide actuation times, pressures, and/or sequences that relate particularly to a wearer's age and/or determined state of activity (e.g., heart rate between 75-100 bpm, heart rate between 100-125 bpm, heart rate between 125-150 bpm, etc.), such modes being manually adjustable (e.g., by a medical care provider) or adjusted by the control system responsive to sensor data.

Figure 25:
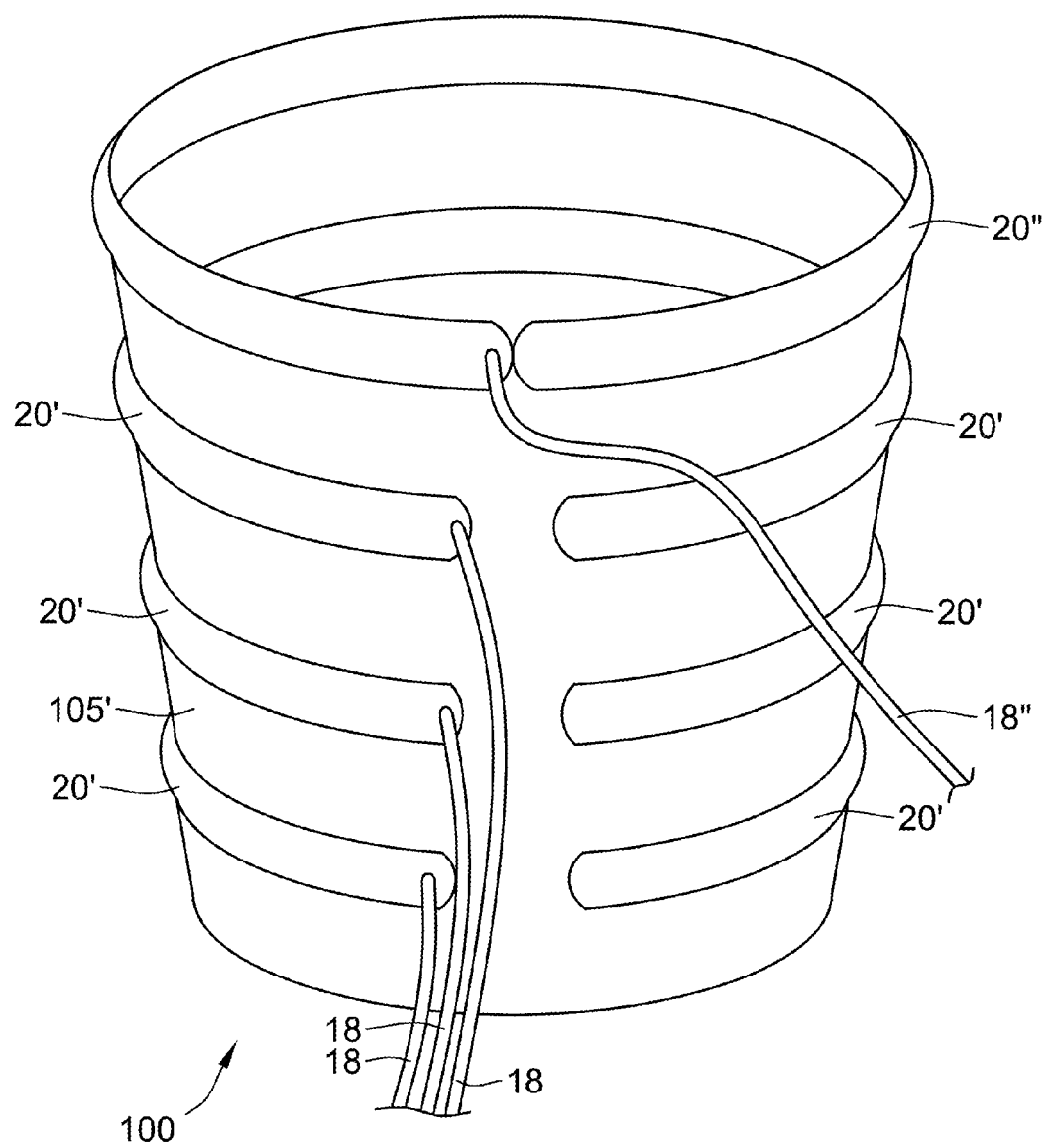
FIG. 25 shows yet another example of a DCC device, in accord with at least some aspects of the present concepts, wherein a static pressurized actuator is provided for to facilitate sizing and adjustability.

FIG. 25 shows another variant of DCC device 100 comprising a first set of circumferential dynamic soft actuators 20', as previously described, that are used to impart compressive forces to the heart at desired times (i.e., at desired portions of the cardiac cycle) and a second set (n=1 in the example shown) of circumferential dynamic soft actuators 20" that are, via the air tubes 18", maintained at a set static pressure selected to provide an appropriate local baseline pressure at an interface between the DCC device 100 and the heart. The static pressure in the circumferential dynamic soft actuator(s) 20" can thus be increased, via the air tubes 18", for tightening (e.g., if the dilated heart started to reverse remodel) or decreased for loosening (e.g., growing pediatric heart). In the particular configuration shown in FIG. 25, the basal circumferential dynamic soft actuator(s) 20" is configured to facilitate or enhance fixation of the DCC device 100 and provide chronic adjustability.

FIGS. 26(*a*)-26(*c*) shows a representation of control systems used for testing and validation of various actuator devices (e.g., DCC devices) disclosed herein as well as for control thereof. A portable air compressor (DeWALT Heavy-Duty 4.5 Gallon, 200 PSI) was used to supply air pressure. The compressor advantageously comprises an accumulator to help smooth output pressure. A pressure regulator, set to 60-100 kPa, was used to down regulate the supply pressure. The 3-way solenoid valve allows the device to be alternatively pressurized and vented to the atmosphere. The solenoid valve was controlled by a microcontroller, which was configured to send a square wave between low (0 V) and high (5 V) at an average frequency of about 70 Hz (30% duty cycle) to a power MOSFET, which connects the power supply to the solenoid on the high signal. The duty cycle was set so that 30% of the cycle was spent in contraction and 70% in expansion, similar to a natural heart. The signal from the pressure gauge microcontroller was recorded by the microcontroller on a memory device (e.g., solid state memory device, hard drive, etc.).

In at least some aspects, a control system suitable for use with a DCC device 100 as disclosed herein comprises a computer (e.g., a laptop computer, tablet computer, desktop computer, etc.), a user interface (e.g., a GUI, a keyboard, etc.), a data acquisition (DAQ) card (e.g., an X-Series DAQ card) and corresponding data logging system installed on the computer, an electrical/pneumatic control unit, and associated tubing connecting the electrical/pneumatic control unit to the DCC device 100. The control and monitoring system is adapted to, via the electrical/pneumatic control unit, control and adjust the DCC device 100 in real-time, while simultaneously monitoring and recording defined physiological variables (e.g., heart rate, pulmonary artery pressure, pulmonary artery flow rate, ascending aortic pressure, ascending aortic flow rate, etc.) and DCC device parameters (e.g., instantaneous pressure of each soft actuator 20, 20', etc.). Advantageously, the control system establishes synchronization to the native cardiac cycle, thus allowing assessment of device assistance control variables to ventricular performance. In one embodiment, the GUI comprises a "virtual instrument" developed within LabVIEW 2013 software. Simultaneous data acquisition and device control is conducted, in some aspects, at 200 Hz, which provides adequate resolution over the cardiac cycle and provides real-time information on cardiac parameters and performance of the DCC device 100.

The control system converts the raw analogue input signals into appropriate units (e.g. 1/min, mmHg), and simultaneously visually displays on the GUI desired information (e.g., profiles of the native ECG, vessel pressures, flow rate, etc.) in waveform charts. The data and/or waveforms is saved/logged on an electronic storage device (e.g., solid state data storage device, hard drive, etc.) and/or printed on a printing device to allow a physiologic profile review at a later point in time. Additionally, the control system advantageously calculates, and displays on the GUI, heart-rate (calculated from the previous cardiac cycle period) and cardiac output (mean flow rate of the previous five cardiac cycles) to provide further real-time cardiac parameter visualization.

FIGS. 26(*b*)-26(*c*) show extension of the generalized control scheme of FIG. 26(*a*) to a plurality of channels (e.g., 8 channels as shown) for an in-situ DCC device. The system is scalable and can be applied to any number of channels.

Two exemplary control schemes are shown in FIGS. 27(*a*)-27(*b*). These control schemes can be modified, for example, to adapt to monitor particular disease conditions (e.g., right side actuation only for right heart failure, etc.). In FIG. 27(*a*), an actuation scheme for the DCC device 100 uses a trigger from the R-peak (R peak amplitude of R wave) on ECG wave, and sequential actuation and relaxation from the apex to the base of the DCC device. At time T2 the apical soft actuator 20' is actuated (pressurized). At time T3, the middle soft actuator 20' is actuated, while the apical soft actuator remains in an actuated state. At time T4, the basal soft actuator 20' is actuated, while both the middle and the apical soft actuators remain in an actuated state. At time T5, the basal soft actuator 20' and the middle soft actuator remain in an actuated state, but the apical soft actuator is deactivated (depressurized). At time T6, the basal soft actuator 20' remains in an actuated state, but the middle and apical soft actuators are deactivated (depressurized). Lastly, at time T7, all of the soft actuators 20' are deactivated. The time points T1-T7, inclusive of the selected triggering event, are user-modifiable and are merely provided as an illustration of the control system's ability to sequentially actuate and deactivate the soft actuators 20, 20' in any desired order or combination. Of course, if a greater number of soft actuators 20' are used (e.g., 4, 5 or 6, or more soft actuators 20'), the potential permutations of actuation increase. In other variants, of course, multiple soft actuators 20' can be simultaneously actuated.

In the example of FIG. 27(a), a delay in the sequential actuation of the soft actuators 20' from apex to base (e.g., between T2-T3, between T3-T4, etc.) was 25 milliseconds between the apical actuator, middle actuator and basal actuator. This particular timing provides effective ejection of the blood from the heart and mimics the natural conduction of electrical potential from apex to base. The DCC device 100 control system is not limited to this timing, which is merely presenting one example and rationale for timing; other timings could alternatively be selected. Further, the delay between each of the actuations need not be uniform and the timing between any particular actuation can be individually selected.

In FIG. 27(b), an actuation scheme for the DCC device 100 uses a flow rate trigger, keyed off of a start of increase of aortic flow, to actuate the soft actuators 20 (i.e., the twisting actuators). At time T1, the start of increase of aortic flow serves as the trigger to initiate an actuation cycle, where, at time T2, all of the soft actuators 20 are simultaneously actuated to cause a twisting of DCC device 100 and vertical compression of the heart. This is followed at time T3 by a simultaneous actuation of all of the soft actuators 20' to cause an inward lateral compression of the DCC device 100. At time T4, all of the soft actuators 20 are simultaneously deactivated, while all of the soft actuators 20' remain actuated, permitting rotation of the DCC device 100 back to its original position and apical descent. At time T5, all of the soft actuators 20' are deactivated.

As discussed above, the DCC device 100 is triggered, in some aspects, from the QRS complex of the ECG wave (e.g., the R peak, etc.). The DCC device 100 can alternatively be triggered by an external control system (e.g., a pacemaker) or other control input(s), such as a measured blood pressure and/or a hemodynamic parameter, such as flow.

Variations of the aforementioned control schemes can be advantageously implemented for different conditions. For example, an actuation mode of the DCC device 100 may be selected as between twisting only, circumferential only, or both twisting and circumferential actuation depending upon a level of assist that is required, which may vary from time to time. In combination, or alternatively, an applied pressure to one or more of the soft actuators 20, 20', 20" may be adjusted, on-the-fly, as may be required by any particular physiological condition. As shown in FIG. 24, the circumferential soft actuators 20' may be bifurcated along a sagittal plane to provide independent left/right actuation and, so configured, the DCC device 100 control system can selectively actuate circumferential actuators 20' only on the right side or left side (e.g., responsive to heart failure on one side).

In other aspects, local actuation of the soft actuators 20, 20' may be controlled responsive to conditions such as, but not limited to, local dyskinesia (impairment in the movement of the heart wall), akinesia (loss of movement of a portion of the heart wall), other antereolateral wall motion abnormality, or an arrhythmia (irregular heart rhythm, which would require resynchronization).

Further, although two layers of actuators 20, 20' are described herein, the present concepts lend themselves to yet additional layers of actuators, which may be provided at angles to the other layers of actuators 20, 20' to provide still additional independent lines of action.

As noted above with respect to FIG. 23, the DCC device 100 can comprise a plurality or, or an array of, pressure sensors 165 providing feedback, thereby enabling dynamic alteration of the DCC device 100 state (e.g., static pressure in soft actuators 20") or actuation states (e.g., control of soft actuator 20, 20' actuation pressure and/or timing). Further, the DCC device, or more particularly an innermost substrate 105', may comprise or define one or more of, or an array of, chambers (i.e., suction cups) connected by at least one of a passage formed in the inner substrate and a tube to a vacuum source configured to selectively form a negative fluid pressure in the chamber(s), thereby causing a differential pressure across the one or more chambers to enhance adhesion of the inner substrate to the object. Thus, if the control system determines that the DCC device 100 is too loose in a particular area, the control system may increase a negative pressure in a plurality of the chambers to enhance securement of the DCC device 100 to the heart. In yet other aspects, the development of the negative pressure in the chambers may be synchronized with the actuation of the soft actuators 20, 20' so at to minimize the potential for relative movement between the DCC device 100 and heart, followed by a release of the negative pressure so as to minimize the potential for tissue damage. In yet other aspects, the development of a negative pressure in the chambers can provide, in combination with actuation of the soft actuators 20, 20', diastolic assistance and can help the heart to fill by "pulling" the myocardium out during diastole (using extending actuators or PAMs with vacuum). In still other aspects, the basal band 160 and/or apex 101 of the DCC device 101 may comprise one or more active (i.e., actuatable) suction cups.

Although the soft actuators 20, 20', 20" described herein by way of example may comprise PAMs, or may be formed from a soft, flexible material (e.g., an elastomer or low Young's Modulus material), the soft actuators may comprise a non-compliant or semi-compliant material or component(s). Further, although the illustrated examples show and describe the actuators 20, 20', 20" as having a generally cylindrical shape, the form-factor of the actuators are not limited to such shape and may include, for example, one or more sections of different cross-sectional area (e.g., a pleated form).

Yet further, in any of the aspects disclosed herein, a first plurality of soft actuators aligned in a first general direction may be provided in opposition to a second plurality of soft actuators aligned in substantially the same first general direction, with each of the soft actuators in the first plurality and the second plurality being configured to operate in opposition to one another in a complementary fashion. For example, the first plurality of the soft actuators are configured for extension, whereas the second plurality of the soft actuators are configured for contraction. Thus, such soft actuators may complement one another and provide biomimetic inputs to the underlying object (e.g., heart).

Each of the foregoing embodiments and variations thereof are contemplated as falling within the spirit and scope of the claimed invention, some aspects of which are set forth in the following claims. Moreover, the concepts disclosed herein expressly include, without limitation, any and all combinations and subcombinations of the preceding elements and aspects.

What is claimed:

1. A biomimetic actuation device comprising:
a flexible substrate made from an elastomeric material and defining an apex and a base, the flexible substrate being conformable for disposition about an underlying object, the flexible substrate having an internal surface that is in direct contact with the underlying object; and
a plurality of soft actuators embedded within the flexible substrate to form a flexible, elastomeric matrix, each soft actuator of the plurality of soft actuators being configured to change state from a first state to a second state upon introduction of a pressurized fluid to an internal volume of the soft actuator, the plurality of soft actuators including
a first group of soft actuators disposed curvilinearly within the substrate from the apex of the substrate toward the base of the substrate, each soft actuator of the first group of actuators being arranged to deliver torsional forces to the underlying object, the torsional forces being delivered via the internal surface of the flexible substrate, and
a second group of soft actuators disposed laterally or circumferentially within the substrate, each soft actuator of the second group of actuators being arranged to deliver compressive or extensive forces to the underlying object, the compressive or extensive forces being delivered via the internal surface of the flexible substrate.

2. The biomimetic actuation device according to claim 1, wherein the substrate is generally planar and is conformable to at least substantially circumscribe a generally frustoconical, cylindrical, or semi-circular object.

3. The biomimetic actuation device according to claim 2, wherein the substrate is in the form of a sleeve or band.

4. The biomimetic actuation device according to claim 3, further comprising one or more fastening elements, the substrate being discontinuous and having a first lateral end and a second lateral end, a positional relation between the first lateral end and the second lateral end being maintained by the one or more fastening elements.

5. The biomimetic actuation device according to claim 1, wherein the substrate defines a generally spheroidal, ellipsoidal, or elliptic parabolic shape, the substrate being conformable to an object having a similarly curved spheroidal, ellipsoidal, or elliptic parabolic shape.

6. The biomimetic actuation device according to claim 1, wherein the substrate includes a composite of at least an inner substrate and an outer substrate.

7. The biomimetic actuation device according to claim 1, wherein the substrate defines one or more chambers on an inner surface of the substrate disposed proximally to an object about which the inner substrate is disposed, and wherein the one or more chambers are connected by at least one of a vacuum passage or vacuum tube configured to permit selective development of a negative fluid pressure within the one or more chambers to cause a differential pressure across the one or more chambers and enhance adhesion of the inner substrate to the object.

8. The biomimetic actuation device according to claim 1, further comprising at least one sensor configured to output a signal relating to a device-variable, a device state, or a biological state, the at least one sensor being disposed (a) on or within at least one of the plurality of soft actuators or (b) on or within the substrate.

9. The biomimetic actuation device according to claim 1, further comprising at least one adjustment actuator disposed to act on at least one of the plurality of soft actuators disposed laterally or circumferentially along the substrate to adjust a baseline level of tension in the at least one of the plurality of soft actuators.

10. A biomimetic actuation system comprising:
a biomimetic actuation device including
a flexible substrate defining an apex and a base, the flexible substrate being conformation for disposition about an underlying object; and
a plurality of soft actuators attached to the flexible substrate, each soft actuator of the plurality of soft actuators being configured to change state from a first state to a second state upon introduction of a pressurized fluid to an internal volume of the respective soft actuator, the plurality of soft actuators including
a first soft actuator disposed curvilinearly along the substrate from the apex of the substrate toward the base of the substrate and arranged to deliver a torsional force to the underlying object, and
a second soft actuator disposed laterally or circumferentially along the substrate and arranged to deliver a compressive or extensive force to the underlying object;
a pressurized fluid source with the pressurized fluid; and
a control system configured to
selectively introduce the pressurized fluid from the pressurized fluid source to the internal volume of each soft actuator to cause the respective soft actuator to change state from the first state to the second state, and
selectively exhaust the pressurized fluid from the internal volume of the respective soft actuator to cause the respective soft actuator to change state from the second state to the first state.

11. The biomimetic actuation system according to claim 10, wherein the substrate is generally planar and is conformable to at least substantially circumscribe a generally frustoconical, cylindrical, or semi-circular object.

12. The biomimetic actuation system according to claim 11, wherein the substrate is in the form of a sleeve or band.

13. The biomimetic actuation system according to claim 11, further comprising one or more fastening elements, the substrate being discontinuous and having a first lateral end and a second lateral end, a positional relation between the first lateral end and the second lateral end being maintained by the one or more fastening elements.

14. The biomimetic actuation system according to claim 10, wherein the substrate simulates a ventricular structure and the biomimetic actuation device is a direct cardiac compression device.

15. The biomimetic actuation system according to claim 10, wherein the substrate includes a composite of at least an inner substrate and an outer substrate.

16. The biomimetic actuation system according to claim 10, wherein the substrate defines one or more chambers on an inner surface of the substrate disposed proximally to the underlying object about which the inner substrate is disposed, the one or more chambers being connected by at least one of a vacuum passage or a vacuum tube configured to permit selective development of a negative fluid pressure within the one or more chambers to cause a differential pressure across the one or more chambers and enhance adhesion of the inner substrate to the underlying object.

17. A biomimetic actuation device comprising:
a matrix of a first plurality of soft actuators disposed on a flexible substrate along a first direction and a second plurality of soft actuators disposed on the flexible substrate along a plurality of second directions, each soft actuator of the first plurality of soft actuators and the second plurality of soft actuators being configured to change state from a first state to a second state upon introduction of a pressurized fluid to an internal volume of the respective soft actuator, wherein the first direction and at least some of the plurality of second directions form one of an acute or oblique angle with respect to one another, wherein the matrix is conformable for disposition about a curved-object such that the first plurality of soft actuators are disposed to deliver compressive forces or extensive forces to the curved-object upon actuation and the second plurality of soft actuators are disposed to deliver at least torsional forces to the curved-object upon actuation.

\* \* \* \* \*

UNITED STATES PATENT AND TRADEMARK OFFICE
CERTIFICATE OF CORRECTION

PATENT NO. : 10,058,647 B2
APPLICATION NO. : 15/027246
DATED : August 28, 2018
INVENTOR(S) : Roche et al.

Page 1 of 1

It is certified that error appears in the above-identified patent and that said Letters Patent is hereby corrected as shown below:

In the Specification

At Column 1, Lines 15-24:
"STATEMENT REGARDING FEDERALLY SPONSORED RESEARCH
Some aspects of the present disclosure were made with government support, under Grant No. 5RO1HL069957 awarded by the National Institutes of Health (NIH), and the government shares rights to such aspects of the present disclosure."

Should be replaced with:
— GOVERNMENT SUPPORT
This invention was made with government support under HL069957 awarded by the National Institutes of Health. The government has certain rights in the invention. —

Signed and Sealed this
Twelfth Day of May, 2020

Andrei Iancu
*Director of the United States Patent and Trademark Office*